US010913728B2

(12) United States Patent
Toscano et al.

(10) Patent No.: US 10,913,728 B2
(45) Date of Patent: Feb. 9, 2021

(54) O-SUBSTITUTED HYDROXAMIC ACIDS

(71) Applicants: The Johns Hopkins University, Baltimore, MD (US); John P. Toscano, Glen Arm, MD (US); Saghar Nourian, Columbia, MD (US); Daryl A. Guthrie, Baltimore, MD (US)

(72) Inventors: John P. Toscano, Glen Arm, MD (US); Saghar Nourian, Columbia, MD (US); Daryl A. Guthrie, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 17 days.

(21) Appl. No.: 16/321,378

(22) PCT Filed: Jul. 27, 2017

(86) PCT No.: PCT/US2017/044197
§ 371 (c)(1),
(2) Date: Jan. 28, 2019

(87) PCT Pub. No.: WO2018/022899
PCT Pub. Date: Feb. 1, 2018

(65) Prior Publication Data
US 2019/0161464 A1 May 30, 2019

Related U.S. Application Data

(60) Provisional application No. 62/367,917, filed on Jul. 28, 2016.

(51) Int. Cl.
*C07D 311/56* (2006.01)
*C07D 239/62* (2006.01)
*C07D 231/28* (2006.01)
*A61P 9/10* (2006.01)

(52) U.S. Cl.
CPC ........... *C07D 311/56* (2013.01); *A61P 9/10* (2018.01); *C07D 231/28* (2013.01); *C07D 239/62* (2013.01)

(58) Field of Classification Search
CPC ....... A61P 9/10; C07D 311/56; C07D 231/28; C07D 239/62
See application file for complete search history.

(56) References Cited

U.S. PATENT DOCUMENTS

| | | |
|---|---|---|
| 6,936,639 B2 | 8/2005 | Wink et al. |
| 7,696,373 B2 | 4/2010 | King |
| 7,863,262 B2 | 1/2011 | Wink et al. |
| 7,989,652 B2 | 8/2011 | King |
| 8,227,639 B2 | 7/2012 | Toscano et al. |
| 8,268,890 B2 | 9/2012 | Wink et al. |
| 8,269,034 B2 | 9/2012 | King |
| 8,318,705 B2 | 11/2012 | Frost et al. |
| 8,569,536 B2 | 10/2013 | King |
| 8,674,132 B2 | 3/2014 | Toscano et al. |
| 8,791,134 B2 | 7/2014 | Frost et al. |
| RE45,314 E | 12/2014 | Toscano et al. |
| 8,987,326 B2 | 3/2015 | Kalish et al. |
| 9,018,411 B2 | 4/2015 | Toscano et al. |
| 9,115,064 B2 | 8/2015 | Toscano et al. |
| 9,156,804 B2 | 10/2015 | Kalish et al. |
| 9,221,780 B2 | 12/2015 | Toscano et al. |
| 9,458,127 B2 | 10/2016 | Toscano et al. |
| 9,464,061 B2 | 10/2016 | Toscano et al. |
| 9,487,498 B2 | 11/2016 | Toscano et al. |
| 9,499,511 B2 | 11/2016 | Toscano et al. |
| 9,586,896 B2 | 3/2017 | Kalish et al. |
| 9,617,208 B2 | 4/2017 | Toscano et al. |
| 9,676,708 B2 | 6/2017 | Toscano et al. |
| 9,682,938 B2 | 6/2017 | Kalish et al. |
| 9,725,402 B2 | 8/2017 | Frost et al. |
| 9,725,410 B2 | 8/2017 | Toscano et al. |
| 9,732,029 B2 | 8/2017 | Frost et al. |
| 9,862,699 B2 | 1/2018 | Toscano et al. |
| 9,932,303 B2 | 4/2018 | Kalish et al. |
| 9,968,584 B2 | 5/2018 | Kalish et al. |
| 9,969,684 B2 | 5/2018 | Toscano et al. |
| 1,017,976 A1 | 1/2019 | Toscano et al. |
| 1,021,340 A1 | 2/2019 | Kalish et al. |
| 2015/0141378 A1 | 5/2015 | Toscano et al. |
| 2015/0366977 A1 | 12/2015 | Kalish et al. |
| 2016/0228460 A1 | 8/2016 | Wink et al. |
| 2018/0185367 A1 | 7/2018 | Toscano et al. |
| 2018/0305304 A1 | 10/2018 | Kalish et al. |
| 2018/0318308 A1 | 11/2018 | Toscano et al. |

FOREIGN PATENT DOCUMENTS

| | | |
|---|---|---|
| WO | WO 2007002444 | 1/2007 |
| WO | WO 2011063400 | 11/2010 |
| WO | WO 2011071951 | 12/2010 |

(Continued)

OTHER PUBLICATIONS

International Preliminary Report on Patentability dated Jan. 29, 2019 in International Patent Application No. PCT/US2017/044197.
International Search Report and Written Opinion dated Oct. 11, 2017 in International Patent Application No. PCT/US2017/044197.
Miao, Z. and King, S.B., "Recent advances in the chemical biology of nitroxy (HNO) detection and generation", In Nitric Oxide: Biology and Chemistry, vol. 57, Apr. 20, 2016, pp. 1-14.
Nourian, S. et al., "Nitrosocarbonyl release from O-substituted hydroxamic acids with pyrazolone leaving groups", In Tetrahedron, vol. 72, No. 40, Aug. 5, 2016, pp. 6037-6042.

(Continued)

*Primary Examiner* — Rebecca L Anderson

(74) *Attorney, Agent, or Firm* — Byrne Poh LLP; Nina R. Horan

(57) ABSTRACT

O-substituted hydroxamic acids with carbon-based leaving groups as HNO donors are disclosed. Pharmaceutical compositions and kits comprising such compounds, and methods of using such compounds or pharmaceutical compositions also are disclosed.

20 Claims, 3 Drawing Sheets

(56) References Cited

FOREIGN PATENT DOCUMENTS

| WO | WO 2013059194 | 4/2013 |
|---|---|---|
| WO | WO 2016210392 | 12/2016 |

OTHER PUBLICATIONS

Xu, C. et al., "Catalytic Asymmetric Oxidative [alpha]-C—H N,O-Ketalization of Ketones by Chiral Primary Amine", In Organic Letters, vol. 17, No. 17, Sep. 4, 2015, pp. 4392-4395.

O-SUBSTITUTED HYDROXAMIC ACIDS

FEDERALLY SPONSORED RESEARCH OR DEVELOPMENT

This invention was made with government support under CHE-1213438 awarded by the National Science Foundation. The government may have certain rights in the invention.

BACKGROUND

Nitroxyl (HNO), a potential heart failure therapeutic (Paolocci N., Saavedra W. F., Miranda K. M., Martignani C., Isoda T., Espey M. G., Hare J. M., Fukuto J. M., Feelisch M., Wink D. A., Kass D. A. Proc. Natl. Acad. Sci. U.S.A. 2001, 98, 10463-10468; and Feelisch, M. Proc. Natl. Acad. Sci. U.S.A. 2003, 100, 4978-4980), is known for its high reactivity. It spontaneously dimerizes to yield hyponitrous acid, which subsequently dehydrates to form, nitrous oxide ($N_2O$) (Shafirovich, V.; Lymar, S. V. Proc. Natl. Acad. Sci. U.S.A. 2002, 99, 7340-7345; Fukuto, J. M.; Bartberger, M. D.; Dutton, A. S.; and Paolocci, N.; Wink, D. A.; Houk, K. N. Chem. Res. Toxicol. 2005, 18, 790-801). Due to HNO's inherent chemical reactivity, it cannot be used directly, and therefore, donors are needed for its in situ generation. Beyond Angeli's salt (AS), Piloty's acid (PA), acyloxy nitroso (AcON) compounds, (hydroxylamino)pyrazolone (HAPY), and (hydroxylamino)barbituric acid (HABA) derivatives, only a limited number of physiologically compatible HNO donors have been reported (Nakagawa, H. J. Inorg. Biochem. 2013, 118, 187-190; Nakagawa, H. Nitric oxide 2011, 25, 195-200; Guthrie, D. A.; Ho, A.; Takahashi, C. G.; Collins, A.; Morris, M.; Toscano, J. P. J. Org. Chem. 2015, 80, 1338-1348; and Guthrie, D. A.; Nourian, S.; Takahashi, C. G.; Toscano, J. P. J. Org. Chem. 2015, 80, 1349-1356).

One of the primary strategies for HNO generation is based on hydrolysis of nitrosocarbonyl intermediates. In 1992, N,O-bis-acylated derivatives of N-hydroxycyanamide were reported by Nagasawa et al., as HNO donors, but only under enzymatic or basic conditions (Nagasawa, H. T.; Lee, M. C.; Kwon, C. H.; Shirota, F. N.; DeMaster, E. G.; Alcohol 1992, 9, 349-353). Along with HNO, toxic cyanide is one of the hydrolysis byproducts. Other non-toxic leaving groups are desired for physiologically compatible HNO applications. O-acylated hydroxamic acids with arenesulfonyl leaving groups as HNO donors also have been reported (Lee, M. J. C.; Nagasawa, H. T.; Elberling, J. A.; DeMaster, E. G. J. Med. Chem. 1992, 35, 3648-3652; and Fukuto, J. M.; Hszieh, R.; Gulati, P.; Chiang, K. T.; Nagasawa, H. T. Biochem. Biophys. Res. Commun. 1992, 187, 1367-1373). These compounds generate HNO upon hydrolysis of the nitrosocarbonyl intermediate under basic conditions. Since these reported donors generated less than 5% HNO at neutral pH, more reactive donors are needed for efficient HNO generation. In 2012, modified N,O-bis-acylated hydroxylamine derivatives with arenesulfonyl leaving groups were reported (Sutton, A. D.; Williamson, M.; Weismiller, H.; Toscano, J. P. Org. Lett. 2012, 14, 472-475). Mechanistic studies revealed that the decomposition chemistry of these donors is more complicated than preliminarily expected. These compounds generate nitrosocarbonyl species under physiological conditions, and upon further hydrolysis release HNO without enzymatic activation; but amide hydrolysis and acyl migration were two other pathways that compete with HNO generation. Recently, N-substituted hydroxamic acids with leaving groups have been reported to generate HNO under physiological conditions (Nourian, S.; Zilber, Z. A.; Toscano, J. P. "Development of N-Substituted Hydroxamic Acids with Pyrazolone Leaving Groups as Nitrosocarbonyl Precursors", manuscript under review; and Nourian, S.; and Toscano, J. P. Development of Novel Precursors to Nitrosocarbonyl Intermediates. Poster session presented at: 36th Reaction Mechanisms Conference: 2016 Jun. 26-29; St. Louis, Mo.). Therefore, a need remains for compounds that generate HNO in excellent yield, under non-enzymatic, physiologically relevant conditions, without producing toxic byproducts.

Citation of any reference in the background of this application is not to be construed as an admission that such reference is prior art to the present application.

SUMMARY

The present disclosure relates to O-substituted hydroxamic acids, pharmaceutical compositions comprising such compounds, kits comprising such compounds, and methods of using such compounds or pharmaceutical compositions.

The compounds of the disclosure generate nitrosocarbonyl intermediates under physiological conditions. See Scheme 1. Following deprotonation and loss of HX (e.g., a pyrazolone), the nitrosocarbonyl intermediate is subsequently hydrolyzed to HNO. A competition between hydrolysis to HNO and trapping by the byproduct HX to the corresponding N-substituted hydroxamic acid (NHPY) can exist, depending on the relative concentration of HX.

Scheme 1. Reactivity of O-substituted Hydroxamic Acids with Good Leaving Groups X

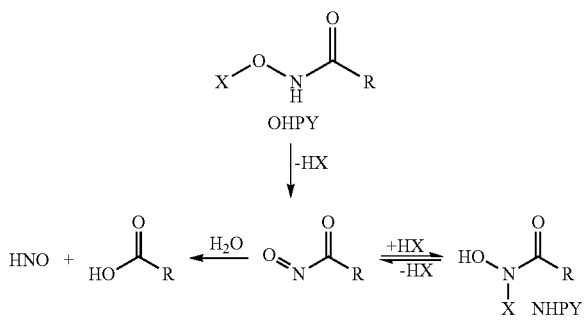

In a particular embodiment, the present disclosure provides compounds of formula (I), formula (II) or formula (III):

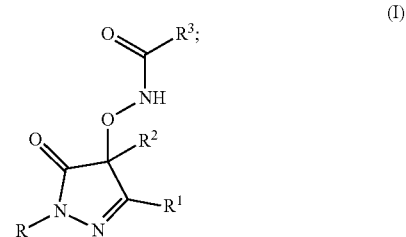

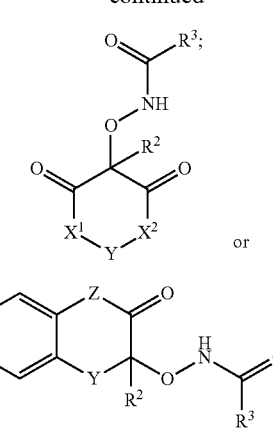

or a pharmaceutically acceptable salt thereof, wherein:

R and $R^1$ are independently selected from the group consisting of hydrogen, $(C_1\text{-}C_6)$alkyl, $(C_1\text{-}C_4)$haloalkyl, $(C_1\text{-}C_4)$perhaloalkyl, $(C_6\text{-}C_{10})$aryl, $(C_1\text{-}C_6)$heteroalkyl, $(C_5\text{-}C_7)$heterocycloalkyl, (5- or 6-membered)heteroaryl, phenylsulfanyl, phenylsulfonyl, phenylsulfinyl and $(C_3\text{-}C_6)$cycloalkyl;

$R^2$ is selected from the group consisting of hydrogen, $(C_1\text{-}C_6)$alkyl, —C(=O)$R^4$, —C(=S)$R^4$, C(=N$R^4$)$R^5$, —C(=NO$R^4$)$R^5$, (5- or 6-membered)heteroaryl and $(C_6\text{-}C_{10})$aryl;

$R^3$ is selected from the group consisting of hydrogen, $(C_1\text{-}C_6)$alkyl, $(C_6\text{-}C_{10})$aryl, —N$R^6R^7$, and —O$R^8$;

$R^4$, $R^5$, $R^6$, $R^7$, and $R^8$ are each independently selected from the group consisting of hydrogen, $(C_1\text{-}C_6)$alkyl, phenyl and benzyl;

$X^1$ and $X^2$ are each independently selected from the group consisting of O, N$R^9$, S, C$R^{10}$, and C$R^{10}R^{11}$;

Y is selected from the group consisting of C(=O), C(=S), C(=N$R^9$), and C$R^{10}R^{11}$;

Z is selected from the group consisting of O and S;

$R^9$, $R^{10}$ and $R^{11}$ are each independently selected from the group consisting of hydrogen and $(C_1\text{-}C_6)$alkyl, wherein said alkyl, aryl, phenyl, benzyl, heteroalkyl, heterocycloalkyl and heteroaryl are unsubstituted or substituted with 1, 2, 3, 4 or 5 substituent(s) selected from halo, $(C_1\text{-}C_6)$alkyl, $(C_1\text{-}C_4)$haloalkyl, $(C_1\text{-}C_4)$perhaloalkyl, $(C_1\text{-}C_6)$alkoxy, $(C_1\text{-}C_4)$haloalkoxy, $(C_1\text{-}C_4)$perhaloalkoxy, —C(=O)OH, —C(=O)O$(C_1\text{-}C_6)$alkyl, —C(=O)N$R^4R^5$, —C(=O)—$(C_1\text{-}C_7)$heterocycloalkyl, $(C_5\text{-}C_7)$heterocycloalkyl, $(C_1\text{-}C_6)$alkylsulfanyl, $(C_1\text{-}C_4)$haloalkylsulfanyl, $(C_1\text{-}C_4)$perhaloalkylsulfanyl, $(C_1\text{-}C_6)$alkylsulfinyl, $(C_1\text{-}C_6)$alkylsulfonyl, $(C_3\text{-}C_6)$cycloalkylsulfonyl, $(C_1\text{-}C_4)$haloalkylsulfinyl, $(C_1\text{-}C_4)$haloalkylsulfonyl, $(C_1\text{-}C_4)$perhaloalkylsulfinyl, $(C_1\text{-}C_4)$perhaloalkylsulfonyl, —S(O)$_2$—NH$_2$, —S(O)$_2$—N$R^6R^7$, —S(O)$_2$-phenyl, —S(O)$_2$—$(C_5\text{-}C_7)$heterocycloalkyl, —S(=O)(=N$R^8$)$(C_1\text{-}C_6)$alkyl, —N$R^4R^5$, N—$(C_1\text{-}C_6)$alkylaminosulfonyl, and N,N-di$(C_1\text{-}C_6)$alkylaminosulfonyl.

Compounds and/or compositions of the disclosure can be used to treat a variety of conditions that are responsive to nitroxyl therapy. For instance, the compounds and/or compositions of the disclosure can be used to treat or prevent the occurrence of cardiovascular diseases, alcoholism, vascular dysfunction and cancer. In certain embodiments, the compounds and/or compositions of the disclosure can be used to treat cardiovascular disease, ischemia/reperfusion injury, pulmonary hypertension or another condition responsive to nitroxyl therapy. In particular embodiments, the compounds and/or compositions of the disclosure can be used to treat heart failure. In a particular embodiment, a compound and/or composition of the disclosure can be used to treat decompensated heart failure (e.g., acute decompensated heart failure). In certain embodiments, the compounds and/or compositions of the disclosure can be used to treat systolic heart failure. In particular embodiments, the compounds and/or compositions of the disclosure can be used to treat diastolic heart failure.

BRIEF DESCRIPTION OF THE FIGURES

Figure 1:
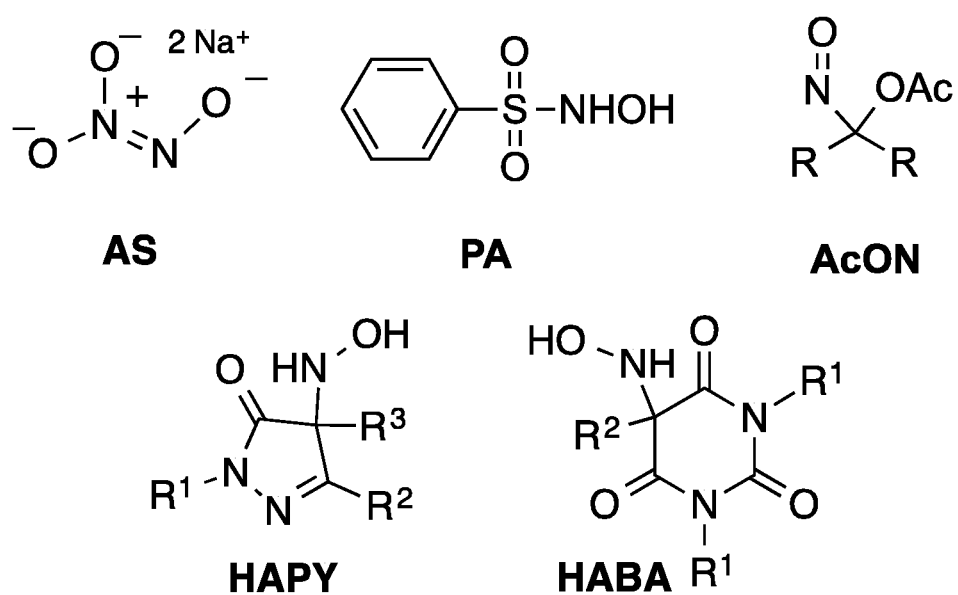

Having thus described the presently disclosed subject matter in general terms, reference will now be made to the accompanying Figures, which are not necessarily drawn to scale, and wherein:

FIG. 1 shows known HNO precursors: Angeli's salt (AS), Piloty's acid (PA), acyloxy nitroso (AcON) compounds, (hydroxylamino)pyrazolone (HAPY), and (hydroxylamino) barbituric acid (HABA) derivatives.

Figure 2:
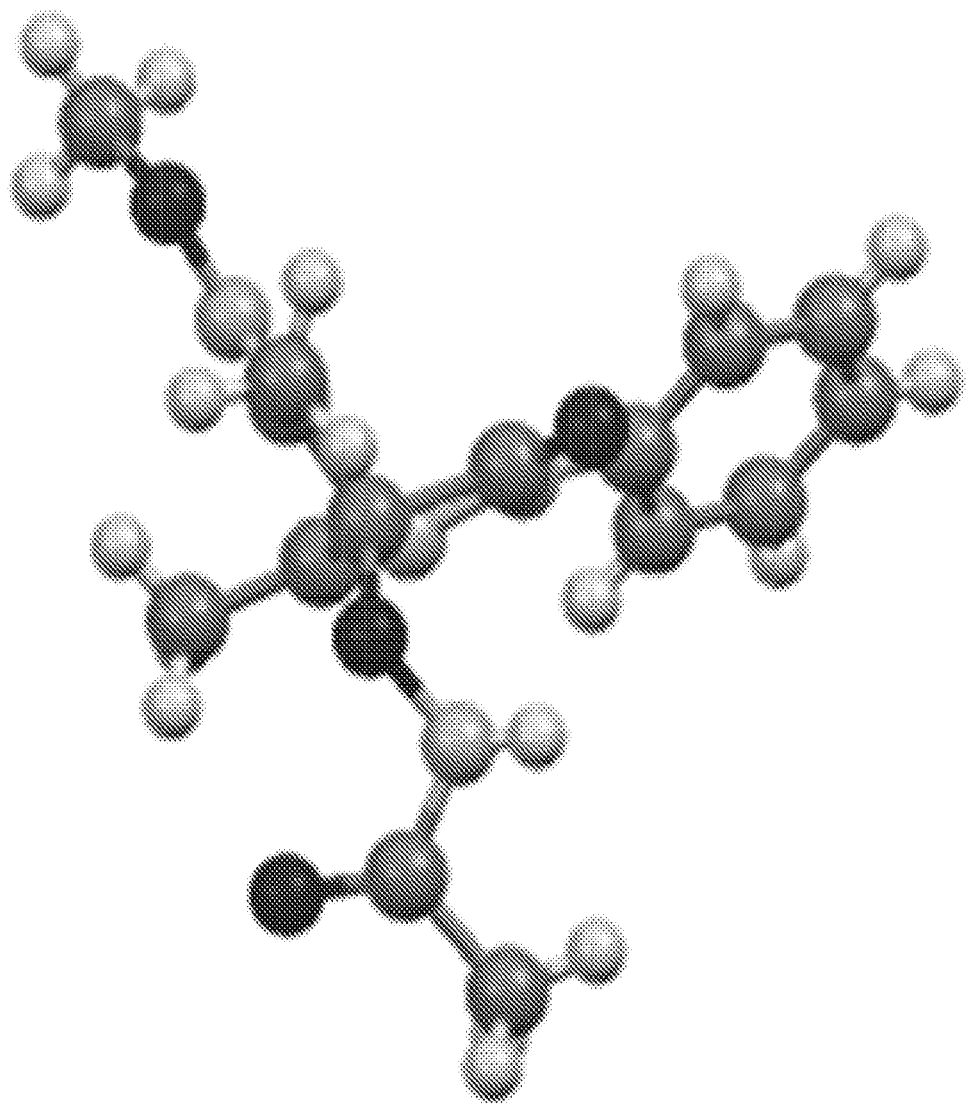

FIG. 2 shows the X-ray crystallographic structure of Compound 1; the white, black and grey spheres represent atoms of carbon (C), oxygen (O), and nitrogen (N), respectively.

Figure 3:
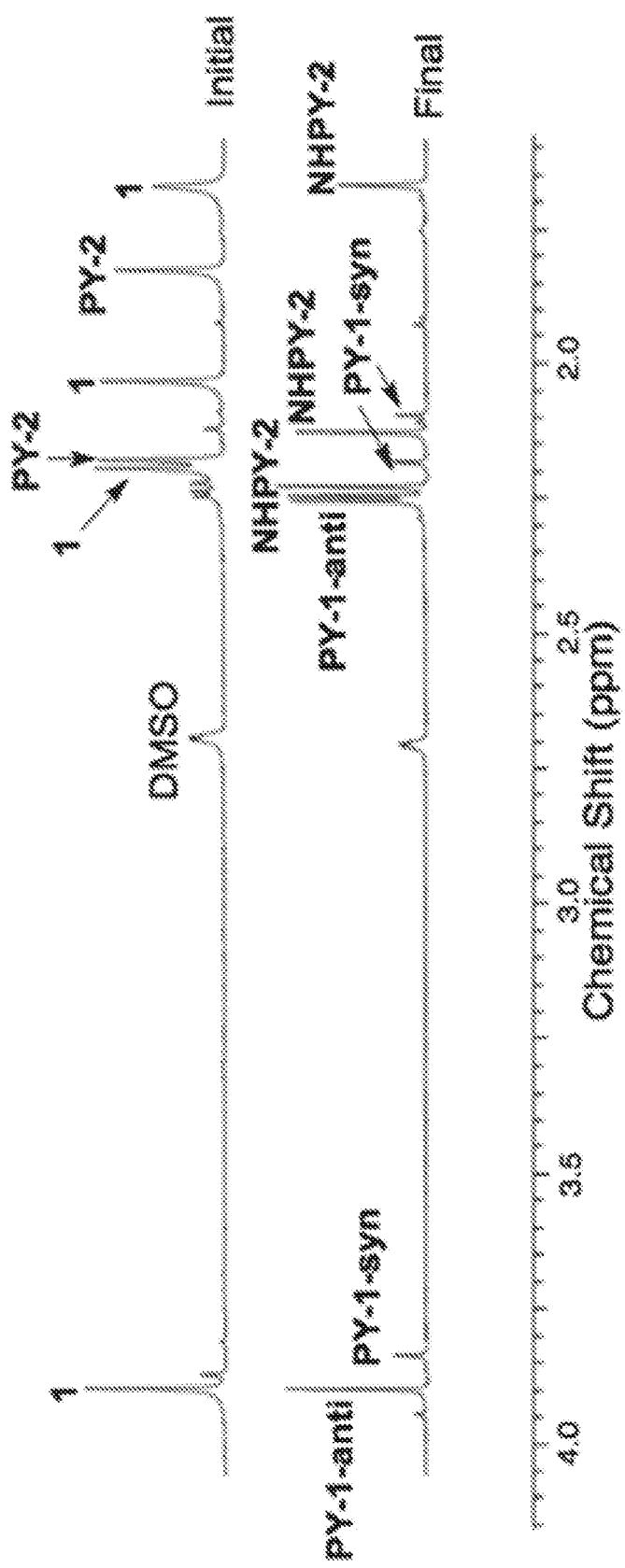

FIG. 3 shows $^1$H NMR analysis of the decomposition of Compound 1 in presence of 0.5 mM of 3,4-dimethyl-1-phenylpyrazolone in 0.25 M phosphate buffer containing 0.2 mM of the metal chelator, diethylenetriaminepentaacetic acid (DTPA), at pH 7.4, 80% H$_2$O, 10% D$_2$O, and 10% DMSO-d$_6$ at 37° C. under argon; spectra were collected at the start of the experiment and after complete decomposition.

DETAILED DESCRIPTION

The invention includes the following:
(1.) A compound of formula (I), formula (II) or formula (III):

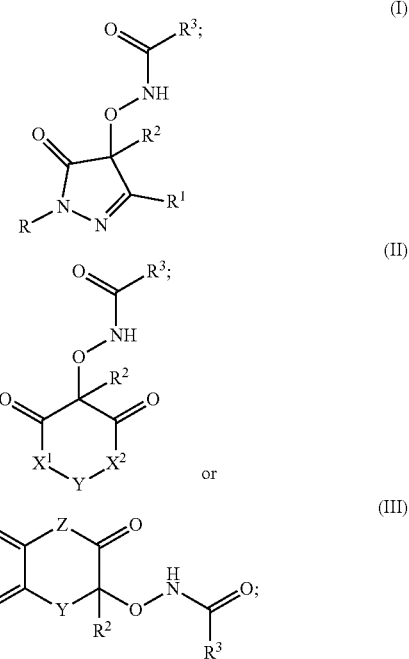

or a pharmaceutically acceptable salt thereof, wherein:

R and $R^1$ are independently selected from the group consisting of hydrogen, $(C_1-C_6)$alkyl, $(C_1-C_4)$haloalkyl, $(C_1-C_4)$perhaloalkyl, $(C_6-C_{10})$aryl, $(C_1-C_6)$heteroalkyl, $(C_5-C_7)$heterocycloalkyl, (5- or 6-membered) heteroaryl, phenylsulfanyl, phenylsulfonyl, phenylsulfinyl and $(C_3-C_6)$cycloalkyl;

$R^2$ is selected from the group consisting of hydrogen, $(C_1-C_6)$alkyl, —C(=O)$R^4$, —C(=S)$R^4$, C(=N$R^4$)$R^5$, —C(=NO$R^4$)$R^5$, (5- or 6-membered)heteroaryl and $(C_6-C_{10})$aryl;

$R^3$ is selected from the group consisting of hydrogen, $(C_1-C_6)$alkyl, $(C_6-C_{10})$aryl, —N$R^6R^7$, and —O$R^8$;

$R^4$, $R^5$, $R^6$, $R^7$, and $R^8$ are each independently selected from the group consisting of hydrogen, $(C_1-C_6)$alkyl, phenyl and benzyl;

$X^1$ and $X^2$ are each independently selected from the group consisting of O, N$R^9$, S, C$R^{10}$, and C$R^{10}R^{11}$;

Y is selected from the group consisting of C(=O), C(=S), C(=N$R^9$), and C$R^{10}R^{11}$;

Z is selected from the group consisting of O and S;

$R^9$, $R^{10}$ and $R^{11}$ are each independently selected from the group consisting of hydrogen and $(C_1-C_6)$alkyl, wherein said alkyl, aryl, phenyl, benzyl, heteroalkyl, heterocycloalkyl and heteroaryl are unsubstituted or substituted with 1, 2, 3, 4 or 5 substituent(s) selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)N$R^4R^5$, —C(=O)—$(C_5-C_7)$heterocycloalkyl, $(C_5-C_6)$heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—N$R^6R^7$, —S(O)$_2$-phenyl, —S(O)$_2$—$(C_5-C_7)$heterocycloalkyl, —S(=O)(=N$R^8$)$(C_1-C_6)$alkyl, —N$R^4R^5$, N—$(C_1-C_6)$alkylaminosulfonyl, and N,N-di$(C_1-C_6)$alkylaminosulfonyl.

(2.) The compound of the above (1.), wherein the compound is of formula (I), (3.) The compound of the above (1.), wherein the compound is of formula (II).

(4.) The compound of the above (1.), wherein the compound is of formula (III).

(5.) The compound of the above (2.), wherein R is selected from the group consisting of hydrogen, $(C_1-C_6)$alkyl, $(C_6-C_{10})$aryl and (5- or 6-membered)heteroaryl, wherein said alkyl, heteroaryl and aryl are unsubstituted or substituted with 1, 2 or 3 substituent(s).

(6.) The compound of the above (2.), wherein R is selected from the group consisting of hydrogen, $(C_1-C_6)$alkyl, (5- or 6-membered)heteroaryl or phenyl, wherein said alkyl, heteroaryl and phenyl are unsubstituted or substituted with 1, 2 or 3 substituent(s).

(7.) The compound of the above (2.), wherein R is selected from the group consisting of hydrogen, methyl and phenyl.

(8.) The compound of the above (2.), wherein R is methyl or phenyl.

(9.) The compound of any one of the above (2.), and (5.) to (8.), wherein $R^1$ is selected from the group consisting of $(C_1-C_6)$alkyl, $(C_1-C_4)$perhaloalkyl, $(C_1-C_6)$alkoxy, $(C_6-C_{10})$aryl, (5- or 6-membered)heteroaryl, phenylsulfanyl, phenylsulfonyl, phenylsulfinyl and $(C_3-C_6)$cycloalkyl, wherein said alkyl, perhaloalkyl, alkoxy, aryl, heteroaryl, phenylsulfanyl, phenylsulfonyl, phenylsulfinyl and cycloalkyl are unsubstituted or substituted with 1, 2 or 3 substituent(s).

(10.) The compound of any one of the above (2.), and (5.) to (8.), wherein $R^1$ is selected from the group consisting of $(C_1-C_6)$alkyl, $(C_1-C_4)$perhaloalkyl, $(C_1-C_6)$alkoxy, phenyl, (5- or 6-membered)heteroaryl, phenylsulfanyl, phenylsulfonyl, phenylsulfinyl and $(C_3-C_6)$cycloalkyl, wherein said alkyl, perhaloalkyl, alkoxy, phenyl, heteroaryl, phenylsulfanyl, phenylsulfonyl, phenylsulfinyl and cycloalkyl are unsubstituted or substituted with 1, 2 or 3 substituent(s).

(11.) The compound of any one of the above (2.), and (5.) to (8.), wherein $R^1$ is methyl or phenyl, wherein said phenyl is unsubstituted or substituted with 1, 2 or 3 substituent(s).

(12.) The compound of the above (3.), wherein $X^1$ and $X^2$ are independently O or N$R^9$.

(13.) The compound of the above (3.), wherein $X^1$ and $X^2$ are O.

(14.) The compound of the above (3.), wherein $X^1$ and $X^2$ are N$R^9$.

(15.) The compound of the above (4.), wherein, Z is O or S.

(16.) The compound of the above (4.), wherein, Z is O.

(17.) The compound of the above (4.), wherein, Z is S.

(18.) The compound of any one of the above (3.), (4.), and (11.) to (17.), wherein Y is C(=O) or C$R^{10}R^{11}$.

(19.) The compound of any one of the above (3.), (4.), and (11.) to (17.), wherein Y is C(=O).

(20.) The compound of any one of the above (3.), (4.), and (11.) to (17.), wherein Y is C$R^{10}R^{11}$.

(21.) The compound of any one of the above (1.) to (20.), wherein $R^2$ is selected from the group consisting of $(C_1-C_6)$alkyl, —C(=O)$R^4$, —C(=S)$R^4$, —C(=N$R^4$)$R^5$, —C(=NO$R^4$)$R^5$, (5- or 6-membered)heteroaryl and $(C_6-C_{10})$aryl, wherein said aryl is unsubstituted or substituted with 1, 2 or 3 substituent(s).

(22.) The compound of any one of the above (1.) to (20.), wherein $R^2$ is selected from the group consisting of $(C_1-C_6)$alkyl, —C(=NO$R^4$)$R^5$, (5- or 6-membered)heteroaryl and phenyl, wherein said alkyl, heteroaryl and phenyl are unsubstituted or substituted with 1, 2 or 3 substituent(s).

(23.) The compound of any one of the above (1.) to (20.), wherein $R^2$ is methyl, —C(=NO$R^4$)$R^5$, or phenyl; and $R^4$ and $R^5$ are independently selected from $(C_1-C_6)$alkyl.

(24.) The compound of any one of the above (1.) to (20.), wherein $R^2$ is methyl or —C(=NO$R^4$)$R^5$; and $R^4$ and $R^5$ are each methyl.

(25.) The compound of any one of the above (1.) to (24.), wherein $R^3$ is selected from the group consisting of $(C_1-C_6)$alkyl, phenyl, —N$R^6R^7$, and $(C_1-C_6)$alkoxy, wherein $R^6$ and $R^7$ are independently selected from hydrogen and $(C_1-C_6)$alkyl.

(26.) The compound of any one of the above (1.) to (24.), wherein $R^3$ is $(C_1-C_6)$alkyl, —N$R^6R^7$ or $(C_1-C_6)$alkoxy.

(27.) The compound of the above (2.), wherein the compound of formula (I) is:
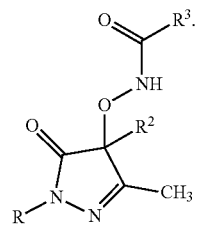
(I')
(28.) The compound of the above (3.), wherein the compound of formula (II) is:
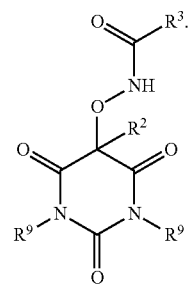
(II')
(29.) The compound of the above (4.), wherein the compound of formula (III) is:
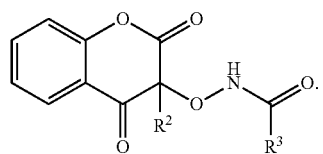
(III')
(30.) The compound of the above (1.), wherein the compound of formula (I) is selected from the group consisting of:
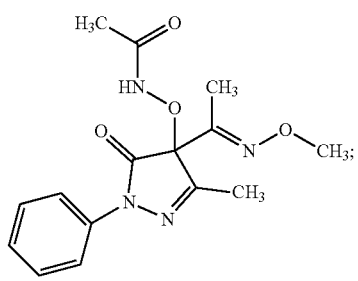
-continued
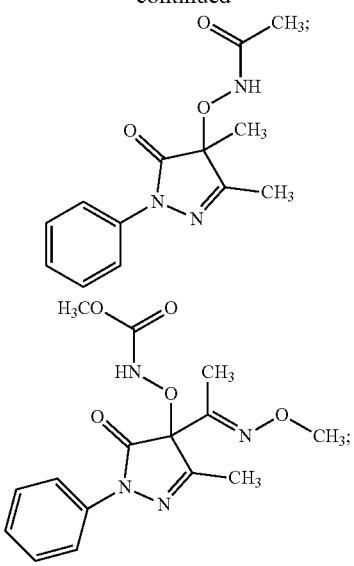
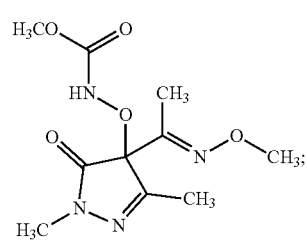
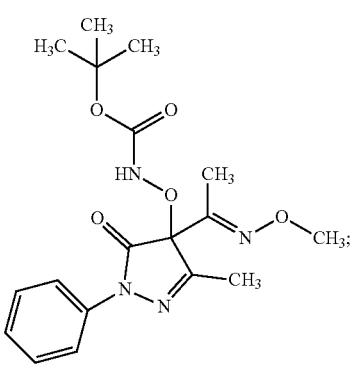
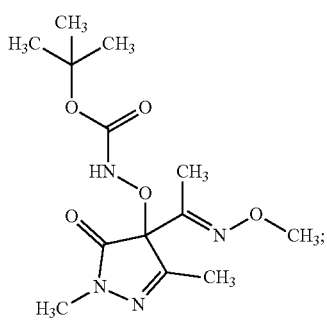

-continued
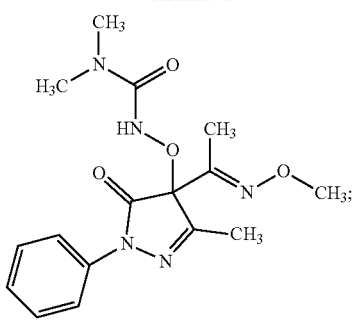
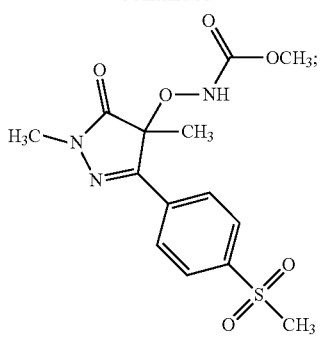
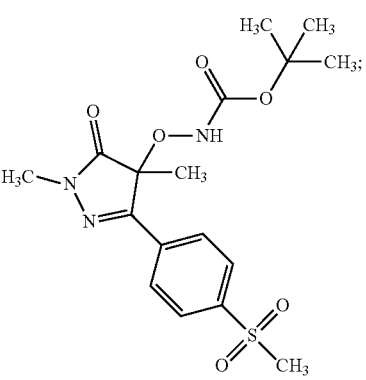
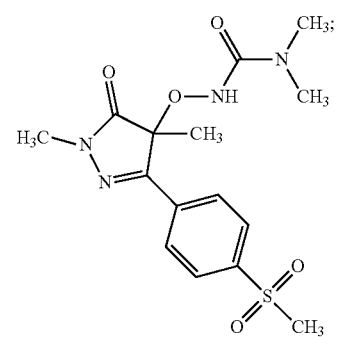
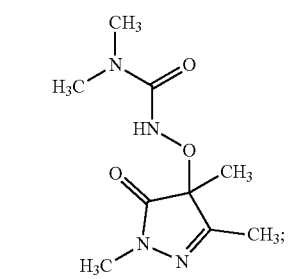
and pharmaceutically acceptable salts thereof.
(31.) The compound of the above (1.), wherein the compound of formula (II) is selected from the group consisting of:
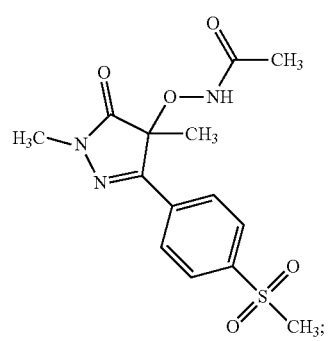
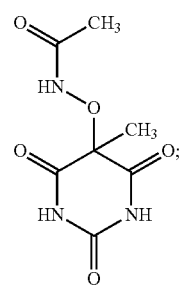

-continued
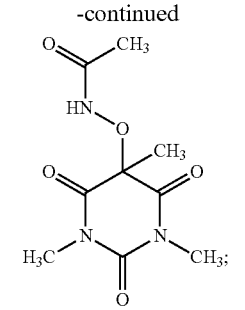
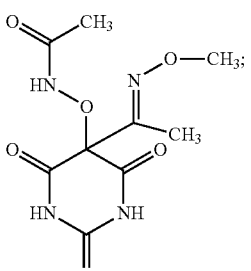
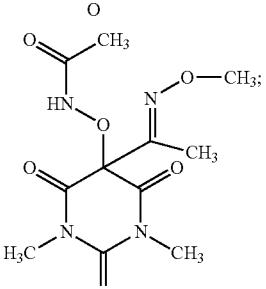
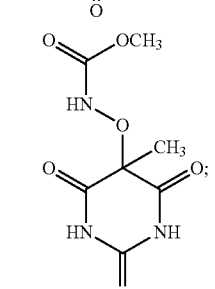
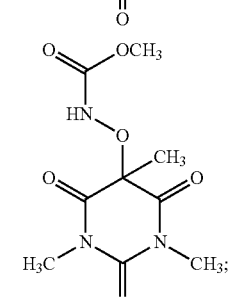
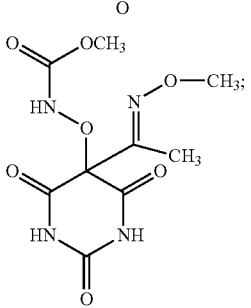
-continued
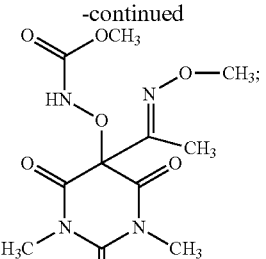
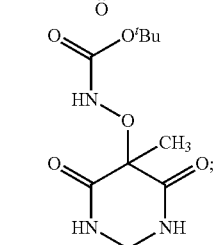
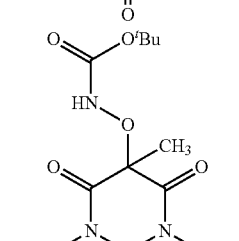
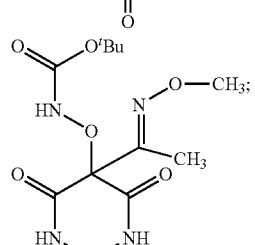
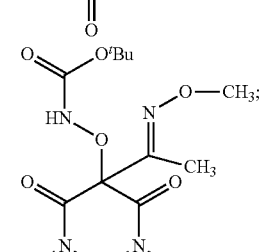
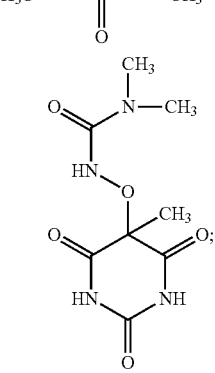

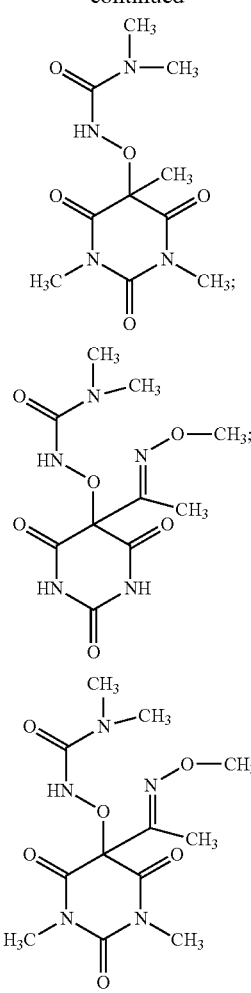

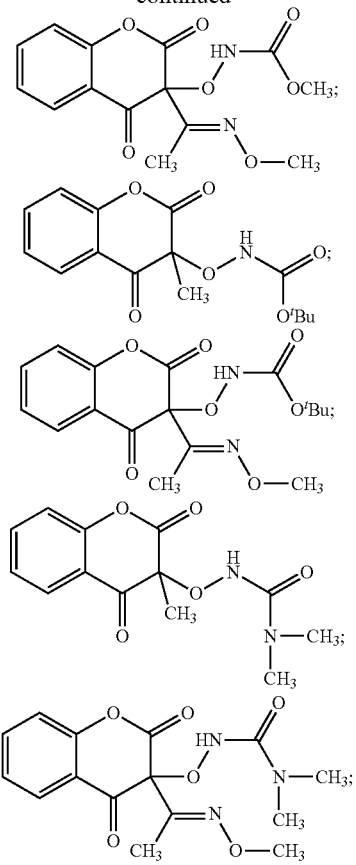

and pharmaceutically acceptable salts thereof.

(32.) The compound of the above (1.), wherein the compound of formula (III) is selected from the group consisting of:

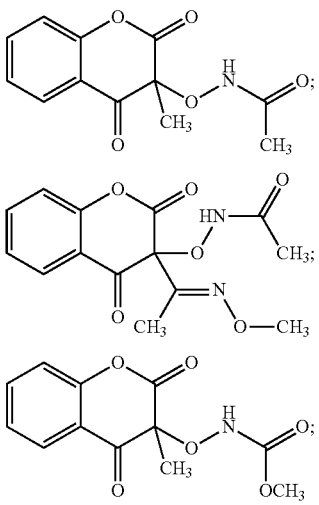

and pharmaceutically acceptable salts thereof.

(33.) A pharmaceutical composition comprising a compound of any of the above (1.) to (32.), and a pharmaceutically acceptable excipient.

(34.) The pharmaceutical composition of the above (33.), wherein the pharmaceutical composition is suitable for oral administration.

(35.) The pharmaceutical composition of the above (33.) or (34.), wherein the pharmaceutical composition is formulated for administration in solid form.

(36.) The pharmaceutical composition of any one of the above (33.) to (35.), wherein the pharmaceutically acceptable excipient is selected from lactose, microcrystalline cellulose, croscarmellose, or any mixture thereof.

(37.) A method for treating and/or preventing a disease or condition responsive to nitroxyl therapy, the method comprising administering to a subject in need of treatment, a compound of any one of the above (1.) to (32.), or a pharmaceutical composition of any one of the above (33.) to (36.), in an amount effective to treat or prevent the disease or condition.

(38.) The method of the above (37.), wherein the disease or condition is selected from cardiovascular diseases, ischemia/reperfusion injury, cancerous disease, and pulmonary-hypertension.

(39.) A method for modulating in vivo nitroxyl levels, the method comprising administering a compound of any one of above (1.) to (32.), or a pharmaceutical composition of any one of the above (33.) to (36.), to a subject in need thereof.

(40.) A method of treating a cardiovascular disease, the method comprising administering an effective amount of the compound of any one of above (1.) to (32.) or the pharmaceutical composition of any one of the above (33.) to (36.) to a patient in need thereof.
(41.) The method of claim (40.), wherein the cardiovascular disease is heart failure.
(42.) The method of claim (41.), wherein the cardiovascular disease is acute decompensated heart failure.
(43.) The method of any one of the above (37.) to (42.), wherein the compound or the pharmaceutical composition is administered orally.
(44.) Use of the compound of any one of above (1.) to (32.) or the pharmaceutical composition of any one of the above (33.) to (36.) for the manufacture of a medicament useful for treating a cardiovascular disease.
(45.) Use of the compound of any one of above (1.) to (32.) or the pharmaceutical composition of any one of the above (33.) to (36.) for the manufacture of a medicament useful for treating heart failure.
(46.) Use of the compound of any one of above (1.) to (32.) or the pharmaceutical composition of any one of the above (33.) to (36.) for the manufacture of a medicament useful for treating acute decompensated heart failure.
(47.) The use of any one of the above (44.) to (46.), wherein the compound or the pharmaceutical composition is administered orally.
(48.) The compound of any one of above (1.) to (32.) or the pharmaceutical composition of any one of the above (33.) to (36.) for use in the treatment of a cardiovascular disease.
(49.) The compound of any one of claims above (1.) to (32.) or the pharmaceutical composition of any one of the above (33.) to (36.) for use in the treatment of heart failure.
(50.) The compound of any one of above (1.) to (32.) or the pharmaceutical composition of any one of the above (33.) to (36.) for use in the treatment of acute decompensated heart failure.
(51.) A kit for treating and/or preventing a disease or condition responsive to nitroxyl therapy comprising a compound of any one of above (1.) to (32.), or a pharmaceutical composition of any one of the above (33.) to (36.); and instructions for use of the kit.
(52.) The kit of the above (51.), wherein the disease or condition is selected from cardiovascular diseases, ischemia/reperfusion injury, cancerous disease, and pulmonary hypertension.
(53.) The kit of the above (52.), wherein the cardiovascular disease is heart failure.

Definitions

Unless clearly indicated otherwise, the following terms as used herein have the meanings indicated below.

A "pharmaceutically acceptable salt" refers to a salt of any therapeutic agent disclosed herein, which salt can include any of a variety of organic and inorganic counter ions known in the art and which salt is pharmaceutically acceptable. When the therapeutic agent contains an acidic functionality, various exemplary embodiments of counter ions are sodium, potassium, calcium, magnesium, ammonium, tetraalkylammonium, and the like. When the therapeutic agent contains a basic functionality, a pharmaceutically acceptable salt can include as a counter ion, by way of example, an organic or inorganic acid, such as hydrochloride, hydrobromide, tartrate, mesylate, acetate, maleate, oxalate, and the like. Illustrative salts include, but are not limited to, sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. Accordingly, a salt can be prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower-alkyl amines), such as mono-, bis-, or tris-(2-hydroxyethyl)amine, 2-hydroxy-tert-butylamine, or tris-(hydroxymethyl)methylamine, N,N-di-lower-alkyl-N-(hydroxy-lower-alkyl)-amines, such as N,N-dimethyl-N-(2-hydroxyethyl) amine, or tri-(2-hydroxyethyl)amine; N-methyl-D-glucamine; and amino acids such as arginine, lysine, and the like. A salt can also be prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

"Pharmaceutically acceptable excipient" refers to any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in Gennaro, Ed., *Remington: The Science and Practice of Pharmacy*, 20$^{th}$ Ed. (Lippincott Williams & Wilkins, Baltimore, Md., 2000) and *Handbook of Pharmaceutical Excipients*, American Pharmaceutical Association, Washington, D.C., (e.g., 1$^{st}$, 2$^{nd}$ and 3$^{rd}$ Eds., 1986, 1994 and 2000, respectively). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose, (2) starches, such as corn starch and potato starch, (3) cellulose and its derivatives, such as sodium carboxymethyl cellulose, ethyl cellulose, cellulose acetate, hydroxypropylmethylcellulose, hydroxypropylcellulose, microcrystalline cellulose, and croscarmellose, such as or croscarmellose sodium, (4) powdered tragacanth, (5) malt, (6) gelatin, (7) talc, (8) excipients, such as cocoa butter and suppository waxes, (9) oils, such as peanut oil, cottonseed oil, safflower oil, sesame oil, olive oil, corn oil and soybean oil, (10) glycols, such as propylene glycol, (11) polyols, such as glycerin, sorbitol, mannitol and polyethylene glycol, (12) esters, such as ethyl oleate and ethyl laurate, (13) agar, (14) buffering agents, such as magnesium hydroxide and aluminum hydroxide, (15) alginic acid, (16) pyrogen-free water, (17) isotonic saline, (18) Ringer's solution, (19) ethyl alcohol, (20) pH buffered solutions, (21) polyesters, polycarbonates and/or polyanhydrides, and (22) other non-toxic compatible substances employed in pharmaceutical formulations.

"Unit dosage form" refers to a physically discrete unit suitable as a unitary dosage for a human or an animal. Each unit dosage form can contain a predetermined amount of a therapeutic agent calculated to produce a desired effect.

Unless clearly indicated otherwise, a "patient" refers to an animal, such as a mammal, including but not limited to a human. Hence, the methods disclosed herein can be useful in human therapy and veterinary applications. In particular embodiments, the patient is a mammal. In certain embodiments, the patient is a human.

"Effective amount" refers to such amount of a therapeutic agent or a pharmaceutically acceptable salt thereof, which in combination with its parameters of efficacy and potential for toxicity, as well as based on the knowledge of the practicing specialist, should be effective in a given therapeutic form. As is understood in the art, an effective amount can be administered in one or more doses.

"Treatment", "treating" and the like is an approach for obtaining a beneficial or desired result, including clinical results. For purposes of this disclosure, beneficial or desired results include but are not limited to inhibiting and/or suppressing the onset and/or development of a condition or reducing the severity of such condition, such as reducing the number and/or severity of symptoms associated with the condition, increasing the quality of life of those suffering from the condition, decreasing the dose of other medications required to treat the condition, enhancing the effect of another medication a patient is taking for the condition, and/or prolonging survival of patients having the condition.

"Prevent", "preventing" and the like refers to reducing the probability of developing a condition in a patient who does not have, but is at risk of developing a condition. A patient "at risk" may or may not have a detectable condition, and may or may not have displayed a detectable condition prior to the treatment methods disclosed herein. "At risk" denotes that a patient has one or more so-called risk factors, which are measurable parameters that correlate with development of a condition and are known in the art. A patient having one or more of these risk factors has a higher probability of developing the condition than a patient without such risk factor(s).

"Positive inotrope" refers to an agent that causes an increase in myocardial contractile function. Exemplary positive inotropes are a beta-adrenergic receptor agonist, an inhibitor of phosphodiesterase activity, and calcium-sensitizers. Beta-adrenergic receptor agonists include, among others, dopamine, dobutamine, terbutaline, and isoproterenol. Analogs and derivatives of such compounds are also included within positive inotropes. For example, U.S. Pat. No. 4,663,351 discloses a dobutamine prodrug that can be administered orally.

A condition that is "responsive to nitroxyl therapy" includes any condition in which administration of a compound that donates an effective amount of nitroxyl under physiological conditions treats and/or prevents the condition, as those terms are defined herein. A condition whose symptoms are suppressed or diminished upon administration of nitroxyl donor is a condition responsive to nitroxyl therapy.

"Pulmonary hypertension" or "PH" refers to a condition in which the pulmonary arterial pressure is elevated. The current hemodynamic definition of PH is a mean pulmonary arterial pressure ("MPAP") at rest of greater than or equal to 25 mmHg. Badesch et al., J. Amer. Coll. Cardiol. 54(Suppl.): S55-S66 (2009).

"N/A" means not assessed.

"$(C_1-C_6)$alkyl" refers to saturated linear and branched hydrocarbon structures having 1, 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_6)$alkyl groups include methyl, ethyl, n-propyl, iso-propyl, n-butyl, tert-butyl, n-hexyl, and the like.

"$(C_2-C_6)$alkenyl" refers to a straight-chain or branched unsaturated hydrocarbon radical having 2, 3, 4, 5 or 6 carbon atoms and a double bond in any position, e.g., ethenyl, 1-propenyl, 2-propenyl (allyl), 1-butenyl, 2-butenyl, 3-butenyl, 1-methylethenyl, 1-methyl-1-propenyl, 2-methyl-2-propenyl, 2-methyl-1-propenyl, 1-methyl-2-propenyl, and the like.

"$(C_2-C_6)$alkynyl" refers to a straight-chain or branched unsaturated hydrocarbon radical having 2, 3, 4, 5 or 6 carbon atoms and a triple bond in any position, e.g., ethynyl, 2-propynyl (propargyl), 1-propynyl, pentynyl, hexynyl, and the like.

"$(C_1-C_4)$perhaloalkyl" refers to a $(C_1-C_4)$alkyl group wherein every hydrogen atom is replaced by halo, each halo being independently selected. Examples of $(C_1-C_4)$perhaloalkyl groups include —$CF_3$, —$CCl_3$, —$CF_2CF_3$, —$CCl_2CF_3$, —$CClFCClF_2$, —$CF(CF_3)_2$, —$CBr(CF_3)$ ($CFCl_2$), and the like.

"$(C_1-C_4)$haloalkyl" refers to a $(C_1-C_4)$alkyl group wherein at least one hydrogen atom is replaced by halo but wherein the $(C_1-C_4)$haloalkyl contains few halos than a $(C_1-C_4)$perhaloalkyl having the same number of carbon atoms as the $(C_1-C_4)$haloalkyl. Each halo of a $(C_1-C_4)$ haloalkyl is independently selected. Examples of $(C_1-C_4)$ haloalkyl groups include —$CHF_2$, —$CH_2F$, —$CHFCl$, —$CH_2CF_3$, —$CHClCHF_2$, —$CHFCHClF$, —$CH(CF_3)_2$, —$CH(CF_3)(CH_3)$, —$CBr(CHF_2)(CHCl_2)$, and the like.

"$(C_1-C_6)$heteroalkyl" refers to a straight or branched hydrocarbon radical having 1, 2, 3, 4, 5 or 6 carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{2 5}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

"$(C_1-C_6)$alkoxy" refers to —O—$(C_1-C_6)$alkyl. Examples of $(C_1-C_6)$alkoxy groups include methoxy, ethoxy, propoxy, n-propoxy, iso-propoxy, butoxy, n-butoxy, sec-butoxy, tert-butoxy, pentoxy, hexyloxy, and the like.

"(C$_3$-C$_6$)cycloalkyl" refers to a saturated cyclic hydrocarbon containing 3, 4, 5, or 6 ring carbon atoms. Examples of (C$_3$-C$_6$)cycloalkyl groups include cyclopropyl, cyclobutyl, cyclopentyl, cyclohexyl, and the like.

"(C$_5$-C$_7$)heterocycloalkyl" refers to a 5-, 6-, or 7-membered, saturated or partially unsaturated, monocyclic-heterocycle containing 1, 2, 3, or 4 ring heteroatoms each independently selected from nitrogen, oxygen, and sulfur, wherein said nitrogen and sulfur heteroatoms may optionally be oxidized and the nitrogen heteroatom may optionally be quaternized. A heterocycloalkyl group can be attached to the parent structure through a carbon or a heteroatom. Examples of (C$_5$-C$_7$)heterocycloalkyl groups include pyrrolidinyl, piperidinyl, piperazinyl, tetrahydro-oxazinyl, tetrahydrofuranyl, thiolanyl, dithiolanyl, pyrrolinyl, pyrazolinyl, pyrazolidinyl, imidazolinyl, imidazolidinyl, tetrahydrofuranone, γ-butyrolactone, 2H-pyranyl, 4H-pyranyl, dioxolanyl, tetrahydropyranyl, dioxanyl, dihydrothiophenyl, morpholinyl, thiomorpholinyl, oxazinyl, tetrahydro-oxazinyl, 1,2,3-triazinanyl, and the like.

"(5- or 6-membered)heteroaryl" refers to a monocyclic aromatic heterocycle ring of 5 or 6 members, i.e., a monocyclic aromatic ring comprising at least one ring heteroatom, e.g., 1, 2, 3, or 4 ring heteroatoms, each independently selected from nitrogen, oxygen, and sulfur. When the (5- or 6-membered)heteroaryl comprises a nitrogen or sulfur atom(s), the nitrogen atom or sulfur atom(s) are optionally oxidized to form the N-oxide or S-oxide(s). A (5- or 6-membered)heteroaryl group can be attached to the parent structure through a carbon or heteroatom. Examples of (5- or 6-membered)heteroaryls include pyridyl, pyrrolyl, pyrazolyl, furyl, imidazolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, thiophenyl, and the like.

"(C$_6$-C$_{10}$)aryl" refers to a monovalent aromatic hydrocarbon group which may be monocyclic, bicyclic or tricyclic, wherein at least one ring in the system is aromatic and wherein each ring in the system contains 3, 4, 5, 6 or 7 ring members. Examples of (C$_6$-C$_{10}$)aryl groups include without limitation phenyl, naphthyl, indanyl, indenyl and tetralinyl. In some embodiments, the aryl is phenyl.

"Halo" or "halogen" refers to fluoro (—F), chloro (—Cl), bromo (—Br) and iodo (—I).

"Oxo" refers to an oxygen atom that is double bonded to a carbon atom.

A compound of the disclosure can contain one, two, or more asymmetric centers and thus can give rise to enantiomers, diastereomers, and other stereoisomeric forms. The disclosure encompasses compounds with all such possible forms, as well as their racemic and resolved forms or any mixture thereof, unless specifically otherwise indicated. When a compound of the disclosure contains an olefinic double bond, a C=N double bond, or any other center of geometric asymmetry, it is intended to include all "geometric isomers", e.g., both Z and E geometric isomers, unless specifically otherwise indicated. All "tautomers", e.g., amine-imine, enamine-enimine, enamine-imine, urea-isourea, ketone-enol, amide-imidic acid, lactam-lactim, are intended to be encompassed by the disclosure as well unless specifically otherwise indicated.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

Compounds of the Disclosure

One aspect of the disclosure provides a compound of formula (I):

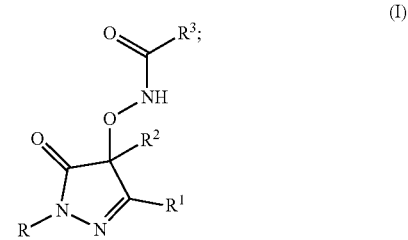

or a pharmaceutically acceptable salt thereof, wherein:

R and R$^1$ are independently selected from the group consisting of hydrogen, (C$_1$-C$_6$)alkyl, (C$_1$-C$_4$)haloalkl, (C$_1$-C$_4$)perhaloalkyl, (C$_6$-C$_{10}$)aryl, (C$_1$-C$_6$)heteroalkyl, (C$_5$-C$_7$)heterocycloalkyl, (5- or 6-membered)heteroaryl, phenylsulfanyl, phenylsulfonyl, phenylsulfinyl and (C$_3$-C$_6$)cycloalkyl;

R$^2$ is selected from the group consisting of hydrogen, (C$_1$-C$_6$)alkyl, —C(=O)R$^4$, —C(=S)R$^4$, C(=NR$^4$)R$^5$, —C(=NOR$^4$)R$^5$, (5- or 6-membered)heteroaryl and (C$_6$-C$_{10}$)aryl;

R$^3$ is selected from the group consisting of hydrogen, (C$_1$-C$_6$)alkyl, (C$_6$-C$_{10}$)aryl, —NR$^6$R$^7$, and —OR$^8$;

R$^4$, R$^5$, R$^6$, R$^7$, and R$^8$ are each independently selected from the group consisting of hydrogen, (C$_1$-C$_6$)alkyl, (C$_1$-C$_6$)alkoxy, phenyl and benzyl;

wherein said alkyl, aryl, phenyl, benzyl, heteroalkyl, heterocycloalkyl and heteroaryl are unsubstituted or substituted with 1, 2, 3, 4 or 5 substituent(s) selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, (C$_5$-C$_7$)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl.

In one embodiment, R is hydrogen, (C$_1$-C$_6$)alkyl, (C$_6$-C$_{10}$)aryl or (5- or 6-membered)heteroaryl, wherein said alkyl, heteroaryl and aryl are unsubstituted or substituted with 1, 2 or 3 substituent(s) independently selected from among the substituents disclosed above in connection with the compounds of formula (I). In another embodiment, R is hydrogen, (C$_1$-C$_6$)alkyl, (5- or 6-membered)heteroaryl or phenyl, wherein said alkyl, heteroaryl and phenyl are unsubstituted or substituted with 1, 2 or 3 substituent(s) independently selected from among the substituents disclosed above in connection with the compounds of formula (I). In another embodiment, R is hydrogen, methyl or unsubstituted phenyl. In another embodiment, R is methyl or unsubstituted phenyl.

In another embodiment, R is H. In another embodiment, R is unsubstituted $(C_1-C_6)$alkyl. In another embodiment, R is $(C_1-C_6)$alkyl substituted with 1, 2 or 3 substituent(s) independently selected from among the substituents disclosed above in connection with the compounds of formula (I). In another embodiment, R is methylcarboxylic acid. In one embodiment, R is methyl, ethyl, iso-propyl, or Serf-butyl. In another embodiment, R is methyl, ethyl, or iso-propyl. In another embodiment, R is methyl, ethyl, or tert-butyl. In another embodiment, R is methyl, iso-propyl, or tert-butyl. In another embodiment, R is ethyl, iso-propyl, or tert-butyl. In another embodiment, R is methyl or ethyl. In another embodiment, R is methyl or iso-propyl. In another embodiment, R is methyl or tert-butyl. In another embodiment, R is ethyl or iso-propyl. In another embodiment, R is ethyl or tert-butyl. In another embodiment, R is iso-propyl or tert-butyl. In another embodiment, R is methyl. In another embodiment, R is ethyl. In another embodiment, R is iso-propyl. In another embodiment, R is tert-butyl. In another embodiment, R is unsubstituted (5- or 6-membered) heteroaryl. In another embodiment, R is (5- or 6-membered) heteroaryl substituted with 1, 2 or 3 substituent(s) independently selected from among the substituents disclosed above in connection with the compounds of formula (I). In another embodiment, R is unsubstituted (5-membered)heteroaryl. In another embodiment, R is (5-membered)heteroaryl substituted with 1, 2 or 3 substituent(s) independently selected from among the substituents disclosed above in connection with the compounds of formula (I). In another embodiment, R is unsubstituted (6-membered)heteroaryl. In another embodiment, R is (6-membered)heteroaryl substituted with 1, 2 or 3 substituent(s) independently selected from among the substituents disclosed above in connection with the compounds of formula (I).

In another embodiment, R is unsubstituted phenyl. In another embodiment, R is phenyl substituted with 1, 2 or 3 substituent(s) independently selected from among the substituents disclosed above in connection with the compounds of formula (I). In another embodiment, R is phenyl, wherein the phenyl is unsubstituted or substituted with 1, 2, or 3 substituent(s) independently selected from halo and methylsulfonyl. In another embodiment, R is phenyl, wherein the phenyl is unsubstituted or substituted with 1 or 2 substituent(s), each substituent being independently selected from halo and methylsulfonyl. In another embodiment, R is phenyl, wherein the phenyl is unsubstituted or monosubstituted or disubstituted with halo. In another embodiment, R is phenyl, wherein the phenyl is unsubstituted or monosubstituted or disubstituted with fluoro. In another embodiment, R is phenyl, wherein the phenyl is unsubstituted or monosubstituted or disubstituted with chloro. In another embodiment, R is or phenyl, wherein the phenyl is unsubstituted or monosubstituted or disubstituted with bromo. In another embodiment, R is phenyl monosubstituted with halo. In another embodiment, R is fluorophenyl. In another embodiment, R is 4-fluorophenyl. In another embodiment, R is 2-fluorophenyl. In another embodiment, R is chlorophenyl. In another embodiment, R is 4-chlorophenyl. In another embodiment, R is 2-chlorophenyl. In another embodiment, R is bromophenyl. In another embodiment, R is 4-bromophenyl. In another embodiment, R is 2-bromophenyl. In another embodiment, R is phenyl, wherein the phenyl is unsubstituted or monosubstituted or disubstituted with methylsulfonyl. In another embodiment, R is phenyl monosubstituted with methylsulfonyl. In another embodiment, R is 4-methylsulfonyl phenyl.

In one embodiment, $R^1$ is $(C_1-C_6)$alkyl, $(C_1-C_4)$perhaloalkyl, $(C_1-C_6)$alkoxy, $(C_6-C_{10})$aryl, (5- or 6-membered)heteroaryl, phenylsulfanyl, phenylsulfonyl, phenylsulfinyl or $(C_3-C_6)$cycloalkyl, wherein said alkyl, perhaloalkyl, alkoxy, aryl, heteroaryl, phenylsulfanyl, phenylsulfonyl, phenylsulfinyl and cycloalkyl are unsubstituted or substituted with 1, 2 or 3 substituent(s) independently selected from among the substituents disclosed above in connection with the compounds of formula (I). In another embodiment, $R^1$ is $(C_1-C_6)$alkyl, $(C_1-C_4)$perhaloalkyl, $(C_1-C_6)$alkoxy, phenyl, (5- or 6-membered)heteroaryl, phenylsulfanyl, phenylsulfonyl, phenylsulfinyl or $(C_3-C_6)$cycloalkyl, wherein said alkyl, perhaloalkyl, alkoxy, phenyl, heteroaryl, phenylsulfanyl, phenylsulfonyl, phenylsulfinyl and cycloalkyl are unsubstituted or substituted with 1, 2 or 3 substituent(s) independently selected from among the substituents disclosed above in connection with the compounds of formula (I). In another embodiment, $R^1$ is $(C_1-C_6)$alkyl, $(C_1-C_6)$alkoxy, $(C_6-C_{10})$aryl, phenylsulfanyl, phenylsulfonyl, phenylsulfinyl or $(C_3-C_6)$cycloalkyl, wherein said alkyl, alkoxy, aryl, phenylsulfanyl, phenylsulfonyl, phenylsulfinyl and cycloalkyl are unsubstituted or substituted with 1, 2 or 3 substituent(s) independently selected from among the substituents disclosed above in connection with the compounds of formula (I).

In another embodiment, $R^1$ is $(C_1-C_6)$alkyl. In one embodiment, $R^1$ is methyl, ethyl, iso-propyl, or tert-butyl. In another embodiment, $R^1$ is methyl, ethyl, or iso-propyl. In another embodiment, $R^1$ is methyl, ethyl, or tert-butyl. In another embodiment, $R^1$ is methyl, iso-propyl, or tert-butyl. In another embodiment, $R^1$ is ethyl, iso-propyl, or tert-butyl. In another embodiment, $R^1$ is methyl or ethyl. In another embodiment, $R^1$ is methyl or iso-propyl. In another embodiment, $R^1$ is methyl or tert-butyl. In another embodiment, $R^1$ is ethyl or iso-propyl. In another embodiment, $R^1$ is ethyl or tert-butyl. In another embodiment, $R^1$ is iso-propyl or tert-butyl. In another embodiment, $R^1$ is methyl. In another embodiment, $R^1$ is ethyl. In another embodiment, $R^1$ is iso-propyl. In another embodiment, $R^1$ is tert-butyl.

In one embodiment, $R^1$ is methyl, trifluoromethyl, ethyl, iso-propyl, or tert-butyl. In another embodiment, $R^1$ is methyl, trifluoromethyl, ethyl, or iso-propyl. In another embodiment, $R^1$ is methyl, trifluoromethyl, ethyl, or tert-butyl. In another embodiment, $R^1$ is methyl, trifluoromethyl, iso-propyl, or tert-butyl. In another embodiment, $R^1$ is trifluoromethyl, ethyl, iso-propyl, or tert-butyl. In another embodiment, $R^1$ is methyl, trifluoromethyl, or ethyl. In another embodiment, $R^1$ is methyl, trifluoromethyl, or iso-propyl. In another embodiment, $R^1$ is methyl, trifluoromethyl, or tert-butyl. In another embodiment, $R^1$ is trifluoromethyl, ethyl or iso-propyl. In another embodiment, $R^1$ is trifluoromethyl, ethyl or tert-butyl. In another embodiment, $R^1$ is trifluoromethyl, iso-propyl or tert-butyl. In another embodiment, $R^1$ is trifluoromethyl or ethyl. In another embodiment, $R^1$ is trifluoromethyl or isopropyl. In another embodiment, $R^1$ is trifluoromethyl or tert-butyl. In another embodiment, $R^1$ is trifluoromethyl.

In another embodiment, $R^1$ is $(C_1-C_6)$alkoxy. In another embodiment, $R^1$ is methoxy, ethoxy or propoxy. In another embodiment, $R^1$ is methoxy or ethoxy. In another embodiment, $R^1$ is methoxy. In another embodiment, $R^1$ is ethoxy.

In another embodiment, $R^1$ is unsubstituted phenyl. In another embodiment, $R^1$ is phenyl substituted with 1, 2 or 3 substituent(s) independently selected from among the substituents disclosed above in connection with the compounds of formula (I). In another embodiment, $R^1$ is phenyl substituted with 1, 2 or 3 substituent(s) independently selected from halo, $(C_1-C_6)$alkyl, $(C_1-C_6)$alkoxy, $(C_1-C_4)$perhaloalkyl, $(C_1-C_4)$perhaloalkoxy, —$NR^4R^5$, $(C_5-C_7)$heterocycloalkyl, $(C_1-C_6)$alkylsulfinyl, $(C_1-C_6)$alkylsulfonyl, $(C_1-C_4)$perhaloalkylsulfonyl, $(C_1-C_4)$perhaloalkylsulfanyl, $(C_1-C_6)$alkylsulfonyl, —$S(O)_2$—$NR^6R^7$, —$S(O)_2$-phenyl, —$C(=O)OH$, —$C(=O)O(C_1-C_6)$alkyl, —$C(=O)$—$(C_5-C_7)$heterocycloalkyl, —$C(=O)NR^4R^5$, —$C(=O)NH$—$S(O)_2(C_1-C_6)$, —$S(=O)(=NR^8)(C_1-C_6)$alkyl, or —$S(O)_2$—$(C_5-C_7)$heterocycloalkyl.

In another embodiment, $R^1$ is phenyl substituted with 1, 2 or 3 substituent(s) independently selected from chloro, fluoro, bromo, trifluoromethyl, methyl, tert-butyl, methylsulfinyl, methylsulfonyl, ethylsulfonyl, methoxy, ethoxy, trifluoromethoxy, trifluoromethylsulfonyl, methylthio, N,N-dimethylsulfonamide, trifluoromethylthio, methoxyformyl, (methyl)oxo-$\lambda^6$-sulfanylidene-2,2,2-trifluoroacetamide, imino(methyl)oxo-$\lambda^6$-sulfanyl, carboxyl, propane-2-sulfonyl, morpholine-4-sulfonyl, morpholine-4-carbonyl, morpholinyl, (2-methoxyethyl)(methyl)amino, N,N-dimethylcarboxamide, 4,4-difluoropiperidine-1-carbonyl, 4-methylpiperazin-1-yl, pyridinyl, benzenesulfonyl, carboxamide, (formamido)propanoic acid, N-methanesulfonylcarboxamide, imino(oxo)propan-2-yl-$\lambda^6$-sulfanyl, N,N-dimethyl-1-sulfonamide, or N-methoxy-N-methyl-1-sulfonamide.

In another embodiment, $R^1$ is phenyl unsubstituted or substituted with 2-chloro, 3-chloro, 4-chloro, 2,3-dichloro, 2,4-dichloro, 3,5-dichloro, 2-chloro-4-fluoro, 2-fluoro, 3-fluoro, 3-chloro-4-methanesulfonyl, 4-bromo, 3-bromo-4-methoxy, 2-trifluoromethyl, 3-trifluoromethyl, 4-trifluoromethyl, 3,5-bis(trifluoromethyl), 2-methyl, 3,5-dimethyl, 4-tert-butyl, 2-methoxy, 4-methoxy, 2-ethoxy-4-fluoro, 3,4-dimethoxy, 4-methoxy-3-methyl, 2-trifluoromethoxy, 4-trifluoromethoxy, 2-methylsulfinyl, 4-methylsulfinyl, 3-methylsulfonyl, 4-methylsulfonyl, 4-ethanesulfonyl, 4-methanesulfonyl-3-methoxy, 4-methanesulfonyl-3,5-dimethyl, 3-fluoro-4-methoxy, 4-(trifluoromethyl)sulfonyl, 4-methylthio, 3-fluoro-4-(methylsulfinyl), 3-fluoro-4-methylsulfonyl, 3-methyl-4-methylsulfinyl, 3-methyl-4-methylsulfonyl, 3,5-difluoro-4-methylsulfonyl, 4-N,N-dimethylsulfonamide, 4-(trifluoromethyl)thio, 4-methoxyformyl, 4-(methyl)oxo-$\lambda^6$-sulfanylidene-2,2,2-trifluoroacetamide, 4-[imino(methyl)oxo-$\lambda^6$-sulfanyl], 4-[imino(oxo)propan-2-yl-$\lambda^6$-sulfanyl], 4-carboxyl, 4-(propane-2-sulfonyl), 4-(morpholine-4-sulfonyl), 4-(morpholine-4-carbonyl), 4-methanesulfonyl-3-(morpholin-4-yl), 4-methanesulfonyl-3-[(2-methoxyethyl)(methyl)amino], 4-N,N-dimethylcarboxamide, 4-(4,4-difluoropiperidine-1-carbonyl); 3-(dimethylamino)-4-methanesulfonyl, 4-methanesulfonyl-3-(4-methylpiperazin-1-yl), 4-benzenesulfonyl, 4-carboxamide, 4-(formamido)propanoic acid, 4-methanesulfonyl-3-(trifluoromethyl), 4-N-methanesulfonylcarboxamide, 3,4-dimethanesulfonyl, 4-N,N-dimethyl-1-sulfonamide or 4-N-methoxy-N-methyl-1-sulfonamide.

In another embodiment, $R^1$ is (5- or 6-membered)heteroaryl. The heteroaryl is unsubstituted in one embodiment, monosubstituted in another embodiment, disubstituted in an additional embodiment, or trisubstituted in a further embodiment, wherein the substituent(s) are selected from among the substituents disclosed above in connection with the compounds of formula (I). In one embodiment, $R^1$ is thienyl. In another embodiment, $R^1$ is thienyl substituted with —$S(O)_2NHOH$. In another embodiment, $R^1$ is pyridyl. In another embodiment, $R^1$ is pyridyl-N-oxide. In another embodiment, $R^1$ is furyl. In another embodiment, $R^1$ is furyl substituted with —$S(O)_2NHOH$.

In one embodiment, $R^1$ is phenylsulfanyl, phenylsulfonyl or phenylsulfinyl. In another embodiment, $R^1$ is phenylsulfanyl. In another embodiment, $R^1$ is phenylsulfonyl. In another embodiment, $R^1$ is phenylsulfinyl.

In another embodiment, $R^1$ is $(C_3-C_6)$cycloalkyl. In another embodiment, $R^1$ is cyclopropyl or cyclobutyl. In another embodiment, $R^1$ is cyclopropyl or cyclopentyl. In another embodiment, $R^1$ is cyclopropyl or cyclohexyl. In another embodiment, $R^1$ is cyclobutyl or cyclopentyl. In another embodiment, $R^1$ is cyclobutyl or cyclohexyl. In another embodiment, $R^1$ is cyclopentyl or cyclohexyl. In another embodiment, $R^1$ is cyclopropyl. In another embodiment, $R^1$ is cyclobutyl. In another embodiment, $R^1$ is cyclopentyl. In another embodiment, $R^1$ is cyclohexyl.

In another embodiment, $R^1$ is selected from methyl, ethyl, propyl, butyl, trifluoromethyl, methoxy, ethoxy, propoxy, cyclopropyl, phenylsulfanyl, phenylsulfonyl, phenylsulfinyl, phenyl or phenyl substituted with 1, 2 or 3 substituent(s) independently selected from chloro, fluoro, bromo, trifluoromethyl, methyl, tert-butyl, methylsulfinyl, methylsulfonyl, ethylsulfonyl, methoxy, ethoxy, trifluoromethoxy, trifluoromethylsulfonyl, methylthio, N,N-dimethylsulfonamide, trifluoromethylthio, methoxyformyl, (methyl)oxo-$\lambda^6$-sulfanylidene-2,2,2-trifluoroacetamide, imino(methyl)oxo-$\lambda^6$-sulfanyl, carboxyl, propane-2-sulfonyl, morpholine-4-sulfonyl, morpholine-4-carbonyl, morpholinyl, (2-methoxyethyl)(methyl)amino, N,N-dimethylcarboxamide, 4,4-difluoropiperidine-1-carbonyl, 4-methylpiperazin-1-yl, pyridinyl, benzenesulfonyl, carboxamide, (formamido)propanoic acid, N-methanesulfonylcarboxamide, imino(oxo)propan-2-yl-$\lambda^6$-sulfanyl, N,N-dimethyl-1-sulfonamide, and N-methoxy-N-methyl-1-sulfonamide. In another embodiment, $R^1$ is selected from methyl or phenyl substituted with a substituent selected from chloro, fluoro, bromo, trifluoromethyl, methyl, tert-butyl, methylsulfinyl, methylsulfonyl, ethylsulfonyl, methoxy, ethoxy, trifluoromethoxy, trifluoromethylsulfonyl, methylthio, N,N-dimethylsulfonamide, trifluoromethylthio, methoxyformyl, (methyl)oxo-$\lambda^6$-sulfanylidene-2,2,2-trifluoroacetamide, imino(methyl)oxo-$\lambda^6$-sulfanyl, carboxyl, propane-2-sulfonyl, morpholine-4-sulfonyl, morpholine-4-carbonyl, morpholinyl, (2-methoxyethyl)(methyl)amino, N,N-dimethylcarboxamide, 4,4-difluoropiperidine-1-carbonyl, 4-methylpiperazin-1-yl, pyridinyl, benzenesulfonyl, carboxamide, (formamido)propanoic acid, N-methanesulfonylcarboxamide, imino(oxo)propan-2-yl-$\lambda^6$-sulfanyl, N,N-dimethyl-1-sulfonamide, and N-methoxy-N-methyl-1-sulfonamide.

In one embodiment, $R^2$ is selected from $(C_1-C_6)$alkyl, —$C(=O)R^4$, —$C(=S)R^4$, $C(=NR^4)R^5$, —$C(=NOR^4)R^5$, (5- or 6-membered)heteroaryl or $(C_6-C_{10})$aryl, wherein said alkyl, heteroaryl and aryl are unsubstituted or substituted with 1, 2 or 3 substituent(s) independently selected from among the substituents disclosed above in connection with the compounds of formula (I). In another embodiment, $R^2$ is selected from $(C_1-C_6)$alkyl, —$C(=NOR^4)R^5$, (5- or 6-membered)heteroaryl or phenyl, wherein said alkyl, heteroaryl and phenyl are unsubstituted or substituted with 1, 2 or 3 substituent(s) independently selected from among the substituents disclosed above in connection with the compounds of formula (I). In another embodiment, $R^2$ is selected from $(C_1-C_6)$alkyl and —$C(=NOR^4)R^5$.

In another embodiment, $R^2$ is $(C_1-C_6)$alkyl. In another embodiment, $R^2$ is methyl, ethyl, iso-propyl, or tert-butyl. In another embodiment, $R^2$ is methyl, ethyl, or iso-propyl. In another embodiment, $R^2$ is methyl, ethyl, or tert-butyl. In another embodiment, $R^2$ is methyl, iso-propyl, or tert-butyl. In another embodiment, $R^2$ is ethyl, iso-propyl, or tert-butyl. In another embodiment, $R^2$ is methyl or ethyl. In another embodiment, $R^2$ is methyl or iso-propyl. In another embodiment, $R^2$ is methyl or tert-butyl. In another embodiment, $R^2$ is ethyl or iso-propyl. In another embodiment, $R^2$ is ethyl or tert-butyl. In another embodiment, $R^2$ is iso-propyl or tert-butyl. In another embodiment, $R^2$ is methyl. In another embodiment, $R^2$ is ethyl. In another embodiment, $R^2$ is iso-propyl. In another embodiment, $R^2$ is tert-butyl.

In another embodiment, $R^2$ is —C(=NOR$^4$)R$^5$. In another embodiment, $R^2$ is —C(=NOR$^4$)R$^5$ wherein at least one of $R^4$ and $R^5$ is methyl. In another embodiment, $R^2$ is —C(=NOR$^4$)R$^5$ wherein each of $R^4$ and $R^5$ is methyl. In another embodiment, $R^2$ is —C(=NOR$^4$)R$^5$ wherein at least one of $R^4$ and $R^5$ is ethyl. In another embodiment, $R^2$ is —C(=NOR$^4$)R$^5$ wherein each of $R^4$ and $R^5$ is ethyl. In another embodiment, $R^2$ is —C(=NOR$^4$)R$^5$ wherein at least one of $R^4$ and $R^5$ is propyl. In another embodiment, $R^2$ is —C(=NOR$^4$)R$^5$ wherein each of $R^4$ and $R^5$ is propyl. In another embodiment, $R^2$ is —C(=NOR$^4$)R$^5$ wherein at least one of $R^4$ and $R^5$ is butyl. In another embodiment, $R^2$ is —C(=NOR$^4$)R$^5$ wherein each of $R^4$ and $R^5$ is butyl. In another embodiment, $R^2$ is —C(=NOR$^4$)R$^5$ wherein $R^4$ is methyl and $R^5$ is ethyl. In another embodiment, $R^2$ is —C(=NOR$^4$)R$^5$ wherein $R^4$ is ethyl and $R^5$ is methyl. In another embodiment, $R^2$ is —C(=NOR$^4$)R$^5$ wherein $R^4$ is methyl and $R^5$ is propyl. In another embodiment, $R^2$ is —C(=NOR$^4$)R$^5$ wherein $R^4$ is propyl and $R^5$ is methyl. In another embodiment, $R^2$ is —C(=NOR$^4$)R$^5$ wherein $R^4$ is methyl and $R^5$ is butyl. In another embodiment, $R^2$ is —C(=NOR$^4$)R$^5$ wherein $R^4$ is butyl and $R^5$ is methyl. In another embodiment, $R^2$ is —C(=NOR$^4$)R$^5$ wherein $R^4$ is ethyl and $R^5$ is propyl. In another embodiment, $R^2$ is —C(=NOR$^4$)R$^5$ wherein $R^4$ is propyl and $R^5$ is ethyl. In another embodiment, $R^2$ is —C(=NOR$^4$)R$^5$ wherein $R^4$ is propyl and $R^5$ is butyl. In another embodiment, $R^2$ is —C(=NOR$^4$)R$^5$ wherein $R^4$ is butyl and $R^5$ is propyl. In another embodiment, $R^2$ is —C(=NOR$^4$)R$^5$ wherein at least one of $R^4$ and $R^5$ is phenyl. In another embodiment, $R^2$ is —C(=NOR$^4$)R$^5$ wherein $R^4$ is phenyl and $R^5$ is methyl. In another embodiment, $R^2$ is —C(=NOR$^4$)R$^5$ wherein $R^4$ is phenyl and $R^5$ is ethyl. In another embodiment, $R^2$ is —C(=NOR$^4$)R$^5$ wherein at least one of $R^4$ and $R^5$ is phenyl substituted with a substituent selected from among the substituents disclosed above in connection with the compounds of formula (I). In another embodiment, $R^2$ is —C(=NOR$^4$)R$^5$ wherein $R^4$ is phenyl substituted with a substituent selected from among the substituents disclosed above in connection with the compounds of formula (I) and $R^5$ is methyl. In another embodiment, $R^2$ is —C(=NOR$^4$)R$^5$ wherein $R^4$ is phenyl substituted with a substituent selected from among the substituents disclosed above in connection with the compounds of formula (I) and $R^5$ is ethyl. In another embodiment, $R^2$ is —C(=NOR$^4$)R$^5$ wherein at least one of $R^4$ and $R^5$ is benzyl. In another embodiment, $R^2$ is —C(=NOR$^4$)R$^5$ wherein $R^4$ is benzyl and $R^5$ methyl. In another embodiment, $R^2$ is —C(=NOR$^4$)R$^5$ wherein $R^4$ is benzyl and $R^5$ ethyl.

In another embodiment, $R^2$ is unsubstituted phenyl. In another embodiment, $R^2$ is phenyl substituted with 1, 2 or 3 substituent(s) independently selected from halo, $(C_1-C_6)$alkyl, $(C_1-C_6)$alkoxy, $(C_1-C_6)$alkylsulfonyl, $(C_1-C_6)$alkylsulfinyl, —C(=O)NR$^4$R$^5$ and —S(O)$_2$—NR$^6$R$^7$.

In another embodiment, $R^2$ is $(C_1-C_6)$alkyl, —C(=NOR$^4$)R$^5$, or phenyl, wherein said alkyl and phenyl are unsubstituted or substituted with 1, 2 or 3 substituent(s) independently selected from among the substituents disclosed above in connection with compounds of formula (I). In another embodiment, $R^2$ is selected from $(C_1-C_6)$alkyl and —C(=NOR$^4$)R$^5$. In another embodiment, $R^2$ is selected from methyl, ethyl, ethylpropanoate, —(C=NOCH$_3$)CH$_3$, —(C=NOphenyl)CH$_3$, —(C=NO-4-bromophenyl)CH$_3$, —(C=NObenzyl)CH$_3$, —(C=NO-(2-methylpropyl))CH$_3$, —(C=NOethyl)CH$_3$, —(C=NOtert-butyl)CH$_3$, phenyl, 3-methylphenyl, 3-chlorophenyl, 4-chlorophenyl, 3-fluorophenyl, 4-fluorophenyl, 4-(methylsulfonyl)phenyl, 3-methoxyphenyl, 4-methoxyphenyl, 4-(methylsulfinyl)phenyl, 3-bromo-4-methoxyphenyl, 3,4-dimethoxyphenyl, 4-methoxy-3-methylphenyl, N,N-dimethylphenyl-1-sulfonamide, N,N-dimethylphenyl-1-carboxamide, or 3-phenyl-1,2,4-oxadiazol-3-yl. In another embodiment, $R^2$ is selected from methyl, —(C=NOCH$_3$)CH$_3$, or phenyl. In another embodiment, $R^2$ is methyl or —(C=NOCH$_3$)CH$_3$.

In one embodiment, $R^3$ is selected from $(C_1-C_6)$alkyl, phenyl, —NR$^6$R$^7$, and —OR$^8$. In another embodiment, $R^3$ is selected from $(C_1-C_6)$alkyl, phenyl, —NR$^6$R$^7$, and $(C_1-C_6)$alkoxy. In another embodiment, $R^3$ is selected from $(C_1-C_6)$alkyl, —NR$^6$R$^7$, and $(C_1-C_6)$alkoxy.

In another embodiment, $R^3$ is $(C_1-C_6)$alkyl. In another embodiment, $R^3$ is methyl, ethyl, iso-propyl, or tert-butyl. In another embodiment, $R^3$ is methyl, ethyl, or iso-propyl. In another embodiment, $R^3$ is methyl, ethyl, or tert-butyl. In another embodiment, $R^3$ is methyl, iso-propyl, or tert-butyl. In another embodiment, $R^3$ is ethyl, iso-propyl, or tert-butyl. In another embodiment, $R^3$ is methyl or ethyl. In another embodiment, $R^3$ is methyl or iso-propyl. In another embodiment, $R^3$ is methyl or tert-butyl. In another embodiment, $R^3$ is ethyl or iso-propyl. In another embodiment, $R^3$ is ethyl or tert-butyl. In another embodiment, $R^3$ is iso-propyl or tert-butyl. In another embodiment, $R^3$ is methyl. In another embodiment, $R^3$ is ethyl. In another embodiment, $R^3$ is iso-propyl. In another embodiment, $R^3$ is tert-butyl.

In another embodiment, $R^3$ is —NR$^6$R$^7$, wherein at least one of $R^6$ and $R^7$ is hydrogen. In another embodiment, $R^3$ is —NR$^6$R$^7$, wherein each of $R^6$ and $R^7$ is hydrogen. In another embodiment, $R^3$ is —NR$^6$R$^7$, wherein at least one of $R^6$ and $R^7$ is $(C_1-C_6)$alkyl. In another embodiment, $R^3$ is —NR$^6$R$^7$, wherein each of $R^6$ and $R^7$ is $(C_1-C_6)$alkyl. In another embodiment, $R^3$ is —NR$^6$R$^7$, wherein at least one of $R^6$ and $R^7$ is methyl. In another embodiment, $R^3$ is —NR$^6$R$^7$, wherein each of $R^6$ and $R^7$ is methyl. In another embodiment, $R^3$ is —NR$^6$R$^7$, wherein at least one of $R^6$ and $R^7$ is ethyl. In another embodiment, $R^3$ is —NR$^6$R$^7$, wherein each of $R^6$ and $R^7$ is ethyl. In another embodiment, $R^3$ is —NR$^6$R$^7$, wherein at least one of $R^6$ and $R^7$ is propyl. In another embodiment, $R^3$ is —NR$^6$R$^7$, wherein each of $R^6$ and $R^7$ is propyl. In another embodiment, $R^3$ is —NR$^6$R$^7$, wherein at least one of $R^6$ and $R^7$ is butyl. In another embodiment, $R^3$ is —NR$^6$R$^7$, wherein each of $R^6$ and $R^7$ is butyl.

In another embodiment, $R^3$ is $(C_1-C_6)$alkoxy. In another embodiment, $R^3$ is methoxy, ethoxy, propoxy or butoxy. In another embodiment, $R^3$ is methoxy or ethoxy. In another embodiment, $R^3$ is methoxy or propoxy. In another embodiment, $R^3$ is methoxy or butoxy. In another embodiment, $R^3$ is ethoxy or propoxy. In another embodiment, $R^3$ is ethoxy or butoxy. In another embodiment, $R^3$ is propoxy or butoxy. In another embodiment, $R^3$ is methoxy. In another embodiment, $R^3$ is ethoxy. In another embodiment, $R^3$ is propoxy. In another embodiment, $R^3$ is butoxy.

In another embodiment, $R^3$ is phenyl unsubstituted or substituted with 1, 2 or 3 substituent(s) independently selected from among the substituents disclosed above in connection with compounds of formula (I). In another embodiment, $R^3$ is unsubstituted phenyl. In another embodiment, $R^3$ is phenyl substituted with a substituent selected from, among the substituents disclosed above in connection with compounds of formula (I). In another embodiment, $R^3$ is methyl, tert-butyl, dimethylamino, methoxy, butoxy or phenyl. In another embodiment, $R^3$ is methyl, dimethylamino, methoxy, or butoxy.

In another embodiment, R is methyl and $R^1$ is methyl. In another embodiment, R is ethyl and $R^1$ is methyl. In another embodiment, R is iso-propyl and $R^1$ is methyl. In another embodiment, R is tert-butyl and $R^1$ is methyl. In another embodiment, R is unsubstituted phenyl and $R^1$ is methyl. In another embodiment, R is monosubstituted phenyl, e.g., selected from among the substituents disclosed above in connection with the compounds of formula (I) and $R^1$ is methyl. In another embodiment, R is disubstituted phenyl, e.g., selected from among the substituents disclosed above in connection with compounds of formula (I) and $R^1$ is methyl. In another embodiment, R is trisubstituted phenyl, e.g., selected from among the substituents disclosed above in connection with the compounds of formula (I) and $R^1$ is methyl. In another embodiment, R is unsubstituted phenyl and $R^1$ is methyl. In another embodiment, R is unsubstituted phenyl and $R^1$ is ethyl. In another embodiment, R is unsubstituted phenyl and $R^1$ is iso-propyl. In another embodiment, R is unsubstituted phenyl and $R^1$ is tert-butyl. In another embodiment, R is unsubstituted phenyl and $R^1$ is unsubstituted phenyl. In another embodiment, R is unsubstituted phenyl and $R^1$ is monosubstituted phenyl, e.g., selected from among the substituents disclosed above in connection with the compounds of formula (I). In another embodiment, R is unsubstituted phenyl and $R^1$ is disubstituted phenyl, e.g., selected from among the substituents disclosed above in connection with the compounds of formula (I). In another embodiment, R is unsubstituted phenyl and $R^1$ is trisubstituted phenyl, e.g., selected from among the substituents disclosed above in connection with the compounds of formula (I).

In another embodiment, R is methyl and $R^2$ is methyl. In another embodiment, R is methyl and $R^2$ is ethyl. In another embodiment, R is ethyl and $R^2$ is methyl. In another embodiment, R is ethyl and $R^2$ is ethyl. In another embodiment, R is iso-propyl and $R^2$ is methyl. In another embodiment, R is iso-propyl and $R^2$ is ethyl. In another embodiment, R is methyl and $R^2$ is iso-propyl. In another embodiment, R is ethyl and $R^2$ is iso-propyl. In another embodiment, R is iso-propyl and $R^2$ is iso-propyl. In another embodiment, R is unsubstituted phenyl and $R^2$ is methyl. In another embodiment, R is unsubstituted phenyl and $R^2$ is ethyl. In another embodiment, R is unsubstituted phenyl and $R^2$ is iso-propyl. In another embodiment, R is methyl and $R^2$ is —C(=NOR$^4$)R$^5$. In another embodiment, R is methyl and $R^2$ is —C(=NOR$^4$)R$^5$, wherein at least one of $R^4$ and $R^5$ is methyl. In another embodiment, R is methyl and $R^2$ is —C(=NOR$^4$)R$^5$, wherein each of $R^4$ and $R^5$ is methyl. In another embodiment, R is methyl and $R^2$ is —C(=NOR$^4$)R$^5$, wherein one of $R^4$ and $R^5$ is methyl and the other is ethyl. In another embodiment, R is ethyl and $R^2$ is —C(=NOR$^4$)R$^5$. In another embodiment, R is ethyl and $R^2$ is —C(=NOR$^4$)R$^5$, wherein at least one of $R^4$ and $R^5$ is methyl. In another embodiment, R is ethyl and $R^2$ is —C(=NOR$^4$)R$^5$, wherein each of $R^4$ and $R^5$ is methyl. In another embodiment, R is ethyl and $R^2$ is —C(=NOR$^4$)R$^5$, wherein one of $R^4$ and $R^5$ is methyl and the other is ethyl. In another embodiment, R is iso-propyl and $R^2$ is —C(=NOR$^4$)R$^5$. In another embodiment, R is iso-propyl and $R^2$ is —C(=NOR$^4$)R$^5$, wherein at least one of $R^4$ and $R^5$ is methyl. In another embodiment, R is iso-propyl and $R^2$ is —C(=NOR$^4$)R$^5$, wherein each of $R^4$ and $R^5$ is methyl. In another embodiment, R is iso-propyl and $R^2$ is —C(=NOR$^4$)R$^5$, wherein one of $R^4$ and $R^5$ is methyl and the other is ethyl.

In another embodiment, R is unsubstituted phenyl and $R^2$ is —C(=NOR$^4$)R$^5$. In another embodiment, R is unsubstituted phenyl and $R^2$ is —C(=NOR$^4$)R$^5$, wherein at least one of $R^4$ and $R^5$ is methyl. In another embodiment, R is unsubstituted phenyl and $R^2$ is —C(=NOR$^4$)R$^5$, wherein each of $R^4$ and $R^5$ is methyl. In another embodiment, R is unsubstituted phenyl and $R^2$ is —C(=NOR$^4$)R$^5$, wherein one of $R^4$ and $R^5$ is methyl and the other is ethyl. In another embodiment, R is unsubstituted phenyl and $R^2$ is methyl. In another embodiment, R is unsubstituted phenyl and $R^2$ is ethyl. In another embodiment, R is unsubstituted phenyl and $R^2$ is iso-propyl. In another embodiment, R is unsubstituted phenyl and $R^2$ is tert-butyl. In another embodiment, R is unsubstituted phenyl and $R^2$ is —C(=NOR$^4$)R$^5$. In another embodiment, R is unsubstituted phenyl and $R^2$ is —C(=NOR$^4$)R$^5$, wherein at least one of $R^4$ and $R^5$ is methyl. In another embodiment, R is unsubstituted phenyl and $R^2$ is —C(=NOR$^4$)R$^5$, wherein each of $R^4$ and $R^5$ is methyl. In another embodiment, R is unsubstituted phenyl and $R^2$ is —C(=NOR$^4$)R$^5$, wherein one of $R^4$ and $R^5$ is methyl and the other is ethyl.

In another embodiment, R is methyl and $R^3$ is methyl. In another embodiment, R is ethyl and $R^3$ is methyl. In another embodiment, R is iso-propyl and $R^3$ is methyl. In another embodiment, R is tert-butyl and $R^3$ is methyl. In another embodiment, R is unsubstituted phenyl and $R^3$ is methyl. In another embodiment, R is methyl and $R^3$ is ethyl. In another embodiment, R is ethyl and $R^3$ is ethyl. In another embodiment, R is iso-propyl and $R^3$ is ethyl. In another embodiment, R is tert-butyl and $R^3$ is ethyl. In another embodiment, R is unsubstituted phenyl and $R^3$ is ethyl. In another embodiment, R is methyl and $R^3$ is iso-propyl. In another embodiment, R is ethyl and $R^3$ is iso-propyl. In another embodiment, R is iso-propyl and $R^3$ is iso-propyl. In another embodiment, R is tert-butyl and $R^3$ is iso-propyl. In another embodiment, R is unsubstituted phenyl and $R^3$ is iso-propyl. In another embodiment, R is methyl and $R^3$ is tert-butyl. In another embodiment, R is ethyl and $R^3$ is tert-butyl. In another embodiment, R is iso-propyl and $R^3$ is tert-butyl. In another embodiment, R is tert-butyl and $R^3$ is tert-butyl. In another embodiment, R is unsubstituted phenyl and $R^3$ is tert-butyl. In another embodiment, R is methyl and $R^3$ is methoxy. In another embodiment, R is ethyl and $R^3$ is methoxy. In another embodiment, R is iso-propyl and $R^3$ is methoxy. In another embodiment, R is tert-butyl and $R^3$ is methoxy. In another embodiment, R is unsubstituted phenyl and $R^3$ is methoxy. In another embodiment, R is methyl and $R^3$ is ethoxy. In another embodiment, R is ethyl and $R^3$ is ethoxy. In another embodiment, R is iso-propyl and $R^3$ is ethoxy. In another embodiment, R is tert-butyl and $R^3$ is ethoxy. In another embodiment, R is unsubstituted phenyl and $R^3$ is ethoxy. In another embodiment, R is methyl and $R^3$ is iso-propoxy. In another embodiment, R is ethyl and $R^3$ is iso-propoxy. In another embodiment, R is iso-propyl and $R^3$ is iso-propoxy. In another embodiment, R is tert-butyl and $R^3$ is iso-propoxy. In another embodiment, R is unsubstituted phenyl and $R^3$ is iso-propoxy. In another embodiment, R is methyl and $R^3$ is tert-butoxy. In another embodiment, R is ethyl and $R^3$ is tert-butoxy. In another embodiment, R is iso-propyl and $R^3$ is tert-butoxy. In another embodiment, R is tert-butyl and $R^3$ is tert-butoxy. In another embodiment, R is unsubstituted phenyl and $R^3$ is tert-butoxy. In another embodiment, R is methyl and $R^3$ is dimethylamino. In another embodiment, R is ethyl and $R^3$ is dimethylamino. In another embodiment, R is iso-propyl and $R^3$ is dimethylamino. In another embodiment, R is tert-butyl and R is dimethylamino. In another embodiment, R is unsubstituted phenyl and $R^3$ is dimethylamino.

In another embodiment, $R^1$ is methyl and $R^2$ is methyl. In another embodiment, $R^1$ is ethyl and $R^2$ is methyl. In another embodiment, $R^1$ is iso-propyl and $R^2$ is methyl. In another embodiment, $R^1$ is tert-butyl and $R^2$ is methyl. In another embodiment, $R^1$ is unsubstituted phenyl and $R^2$ is methyl. In another embodiment, $R^1$ is methyl and $R^2$ is ethyl. In another embodiment, $R^1$ is ethyl and $R^2$ is ethyl. In another embodiment, $R^1$ is iso-propyl and $R^2$ is ethyl. In another embodiment, $R^1$ is tert-butyl and $R^2$ is ethyl. In another embodiment, $R^1$ is unsubstituted phenyl and $R^2$ is ethyl. In another embodiment, $R^1$ is methyl and $R^2$ is iso-propyl. In another embodiment, $R^1$ is ethyl and $R^2$ is iso-propyl. In another embodiment, $R^1$ is iso-propyl and $R^2$ is iso-propyl. In another embodiment, $R^1$ is tert-butyl and $R^2$ is iso-propyl. In another embodiment, $R^1$ is unsubstituted phenyl and $R^2$ is iso-propyl. In another embodiment, $R^1$ is methyl and $R^2$ is tert-butyl. In another embodiment, $R^1$ is ethyl and $R^2$ is tert-butyl. In another embodiment, $R^1$ is iso-propyl and $R^2$ is tert-butyl. In another embodiment, $R^1$ is tert-butyl and $R^2$ is tert-butyl. In another embodiment, $R^1$ is unsubstituted phenyl and $R^2$ is tert-butyl.

In another embodiment, $R^1$ is methyl and $R^2$ is —C(=NOR$^4$)R$^5$. In another embodiment, $R^1$ is methyl and $R^2$ is —C(=NOR$^4$)R$^5$, wherein at least one of $R^4$ and $R^5$ is methyl. In another embodiment, $R^1$ is methyl and $R^2$ is —C(=NOR$^4$)R$^5$, wherein each of $R^4$ and $R^5$ is methyl. In another embodiment, $R^1$ is methyl and $R^2$ is —C(=NOR$^4$)R$^5$, wherein one of $R^4$ and $R^5$ is methyl and the other is ethyl. In another embodiment, $R^1$ is ethyl and $R^2$ is —C(=NOR$^4$)R$^5$. In another embodiment, $R^1$ is ethyl and $R^2$ is —C(=NOR$^4$)R$^5$, wherein at least one of $R^4$ and $R^5$ is methyl. In another embodiment, $R^1$ is ethyl and $R^2$ is —C(=NOR$^4$)R$^5$, wherein each of $R^4$ and $R^5$ is methyl. In another embodiment, $R^1$ is ethyl and $R^2$ is —C(=NOR$^4$)R$^5$, wherein one of $R^4$ and $R_5$ is methyl and the other is ethyl. In another embodiment, $R^1$ is iso-propyl and $R^2$ is —C(=NOR$^4$)R$^5$. In another embodiment, $R^1$ is iso-propyl and $R^2$ is —C(=NOR$^4$)R$^5$, wherein at least one of $R^4$ and $R^5$ is methyl. In another embodiment, $R^1$ is iso-propyl and $R^2$ is —C(=NOR$^4$)R$^5$, wherein each of $R^4$ and $R^5$ is methyl. In another embodiment, $R^1$ is iso-propyl and $R^2$ is —C(=NOR$^4$)R$^5$, wherein one of $R^4$ and $R^5$ is methyl and the other is ethyl. In another embodiment, $R^1$ is tert-butyl and $R^2$ is —C(=NOR$^4$)R$^5$. In another embodiment, $R^1$ is tert-butyl and $R^2$ is —C(=NOR$^4$)R$^5$, wherein at least one of $R^4$ and $R^5$ is methyl. In another embodiment, $R^1$ is tert-butyl and $R^2$ is —C(=NOR$^4$)R$^5$, wherein each of $R^4$ and $R^5$ is methyl. In another embodiment, $R^1$ is tert-butyl and $R^2$ is —C(=NOR$^4$)R$^5$, wherein one of $R^4$ and $R^5$ is methyl and the other is ethyl.

In another embodiment, $R^1$ is monosubstituted phenyl, e.g., selected from among the substituents disclosed above in connection with the compounds of formula (I), and $R^2$ is methyl. In another embodiment, $R^1$ is monosubstituted phenyl, e.g., selected from among the substituents disclosed above in connection with the compounds of formula (I), and $R^2$ is ethyl. In another embodiment, $R^1$ is monosubstituted phenyl, e.g., selected from among the substituents disclosed above in connection with the compounds of formula (I), and $R^2$ is iso-propyl. In another embodiment, $R^1$ is monosubstituted phenyl, e.g., selected from among the substituents disclosed above in connection with the compounds of formula (I), and $R^2$ is tert-butyl. In another embodiment, $R^1$ is monosubstituted phenyl, e.g., selected from among the substituents disclosed above in connection with the compounds of formula (I), and $R^2$ is —C(=NOR$^4$)R$^5$. In another embodiment, $R^5$ is monosubstituted phenyl, e.g., selected from among the substituents disclosed above in connection with the compounds of formula (I), and $R^2$ is —C(=NOR$^4$)R$^5$, wherein at least one of $R^4$ and $R^5$ is methyl. In another embodiment, $R^1$ is monosubstituted phenyl, e.g., selected from among the substituents disclosed above in connection with the compounds of formula (I), and $R^2$ is —C(=NOR$^4$)R$^5$, wherein each of $R^4$ and $R^5$ is methyl. In another embodiment, $R^1$ is monosubstituted phenyl, e.g., selected from among the substituents disclosed above in connection with the compounds of formula (I), and $R^2$ is —C(=NOR$^4$)R$^5$, wherein one of $R^4$ and $R^5$ is methyl and the other is ethyl.

In another embodiment, $R^1$ is disubstituted phenyl, e.g., selected from among the substituents disclosed above in connection with the compounds of formula (I), and $R^2$ is methyl. In another embodiment, $R^1$ is disubstituted phenyl, e.g., selected from among the substituents disclosed above in connection with the compounds of formula (I), and $R^2$ is ethyl. In another embodiment, $R^1$ is disubstituted phenyl, e.g., selected from among the substituents disclosed above in connection with the compounds of formula (I), and $R^2$ is iso-propyl. In another embodiment, $R^1$ is disubstituted phenyl, e.g., selected from among the substituents disclosed above in connection with the compounds of formula (I), and $R^2$ is tert-butyl. In another embodiment, $R^1$ is disubstituted phenyl, e.g., selected from among the substituents disclosed above in connection with the compounds of formula (I), and $R^2$ is —C(=NOR$^4$)R$^5$. In another embodiment, $R^1$ is disubstituted phenyl, e.g., selected from among the substituents disclosed above in connection with the compounds of formula (I), and $R^2$ is —C(=NOR$^4$)R$^5$, wherein at least one of $R^4$ and $R^5$ is methyl. In another embodiment, $R^1$ is disubstituted phenyl, e.g., selected from among the substituents disclosed above in connection with the compounds of formula (I), and $R^2$ is —C(=NOR$^4$)R$^5$, wherein each of $R^4$ and $R^5$ is methyl. In another embodiment, $R^1$ is disubstituted phenyl, e.g., selected from among the substituents disclosed above in connection with the compounds of formula (I), and $R^2$ is —C(=NOR$^4$)R$^5$, wherein one of $R^4$ and $R^5$ is methyl and the other is ethyl.

In another embodiment, $R^1$ is methyl and $R^3$ is methyl. In another embodiment, $R^1$ is ethyl and $R^3$ is methyl. In another embodiment, $R^1$ is iso-propyl and $R^3$ is methyl. In another embodiment, $R^1$ is tert-butyl and $R^3$ is methyl. In another embodiment, $R^1$ is unsubstituted phenyl and $R^3$ is methyl. In another embodiment, $R^1$ is methyl and $R^3$ is ethyl. In another embodiment, $R^1$ is ethyl and $R^3$ is ethyl. In another embodiment, $R^1$ is iso-propyl and $R^3$ is ethyl. In another embodiment, $R^1$ is tert-butyl and $R^3$ is ethyl. In another embodiment, $R^1$ is unsubstituted phenyl and $R^3$ is ethyl. In another embodiment, $R^1$ is methyl and $R^3$ is iso-propyl. In another embodiment, $R^1$ is ethyl and $R^3$ is iso-propyl. In another embodiment, $R^1$ is iso-propyl and $R^3$ is iso-propyl. In another embodiment, $R^1$ is tert-butyl and $R^3$ is iso-propyl. In another embodiment, $R^1$ is unsubstituted phenyl and $R^3$ is iso-propyl. In another embodiment, $R^1$ is methyl and $R^3$ is tert-butyl. In another embodiment, $R^1$ is ethyl and $R^3$ is tert-butyl. In another embodiment, $R^1$ is iso-propyl and $R^3$ is tert-butyl. In another embodiment, $R^1$ is tert-butyl and $R^3$ is tert-butyl.

In another embodiment, $R^1$ is monosubstituted phenyl, e.g., selected from among the substituents disclosed above in connection with the compounds of formula (I), and $R^3$ is methyl. In another embodiment, $R^1$ is monosubstituted phenyl, e.g., selected from among the substituents disclosed above in connection with the compounds of formula (I), and $R^3$ is ethyl. In another embodiment, $R^1$ is monosubstituted phenyl, e.g., selected from among the substituents disclosed above in connection with the compounds of formula (I), and $R^3$ is iso-propyl. In another embodiment, $R^1$ is monosubstituted phenyl, e.g., selected from among the substituents disclosed above in connection with the compounds of formula (I), and $R^3$ is tert-butyl.

In another embodiment, $R^1$ is disubstituted phenyl, e.g., selected from among the substituents disclosed above in connection with the compounds of formula (I), and $R^3$ is methyl. In another embodiment, $R^1$ is disubstituted phenyl, e.g., selected from among the substituents disclosed above in connection with the compounds of formula (I), and $R^3$ is ethyl. In another embodiment, $R^1$ is disubstituted phenyl, e.g., selected from among the substituents disclosed above in connection with the compounds of formula (I), and $R^3$ is iso-propyl. In another embodiment, $R^1$ is disubstituted phenyl, e.g., selected from among the substituents disclosed above in connection with the compounds of formula (I), and $R^3$ is tert-butyl.

In another embodiment, $R^1$ is methyl and $R^3$ is methoxy. In another embodiment, $R^1$ is ethyl and $R^3$ is methoxy. In another embodiment, $R^1$ is iso-propyl and $R^3$ is methoxy. In another embodiment, $R^1$ is tert-butyl and $R^3$ is methoxy. In another embodiment, $R^1$ is unsubstituted phenyl and $R^3$ is methoxy. In another embodiment, $R^1$ is methyl and $R^3$ is ethoxy. In another embodiment, $R^1$ is ethyl and $R^3$ is ethoxy. In another embodiment, $R^1$ is iso-propyl and $R^3$ is ethoxy. In another embodiment, $R^1$ is tert-butyl and $R^3$ is ethoxy. In another embodiment, $R^1$ is unsubstituted phenyl and $R^3$ is ethoxy. In another embodiment, $R^1$ is methyl and $R^3$ is iso-propoxy. In another embodiment, $R^1$ is ethyl and $R^3$ is iso-propoxy. In another embodiment, $R^1$ is iso-propyl and $R^3$ is iso-propoxy. In another embodiment, $R^1$ is tert-butyl and $R^3$ is iso-propoxy. In another embodiment, $R^1$ is unsubstituted phenyl and $R^3$ is iso-propoxy. In another embodiment, $R^1$ is methyl and $R^3$ is tert-butoxy. In another embodiment, $R^1$ is ethyl and $R^3$ is tert-butoxy. In another embodiment, $R^1$ is iso-propyl and $R^3$ is tert-butoxy. In another embodiment, $R^1$ is tert-butyl and $R^3$ is tert-butoxy.

In another embodiment, $R^1$ is monosubstituted phenyl, e.g., selected from among the substituents disclosed above in connection with the compounds of formula (I), and $R^3$ is methoxy. In another embodiment, $R^1$ is monosubstituted phenyl, e.g., selected from among the substituents disclosed above in connection with the compounds of formula (I), and $R^3$ is ethoxy. In another embodiment, $R^1$ is monosubstituted phenyl, e.g., selected from among the substituents disclosed above in connection with the compounds of formula (I), and $R^3$ is iso-propoxy. In another embodiment, $R^1$ is monosubstituted phenyl, e.g., selected from among the substituents disclosed above in connection with the compounds of formula (I), and $R^3$ is tert-butoxy.

In another embodiment, $R^1$ is disubstituted phenyl, e.g., selected from among the substituents disclosed above in connection with the compounds of formula (I), and $R^3$ is methoxy. In another embodiment, $R^1$ is disubstituted phenyl, e.g., selected from among the substituents disclosed above in connection with the compounds of formula (I), and $R^3$ is ethoxy. In another embodiment, $R^1$ is disubstituted phenyl, e.g., selected from among the substituents disclosed above in connection with the compounds of formula (I), and $R^3$ is iso-propoxy. In another embodiment, $R^1$ is disubstituted phenyl, e.g., selected from among the substituents disclosed above in connection with the compounds of formula (I), and $R^3$ is tert-butoxy.

In another embodiment, $R^1$ is methyl and $R^3$ is dimethylamino. In another embodiment, $R^1$ is ethyl and $R^3$ is dimethylamino. In another embodiment, $R^1$ is iso-propyl and $R^3$ is dimethylamino. In another embodiment, $R^1$ is tert-butyl and $R^3$ is dimethylamino. In another embodiment, $R^1$ is unsubstituted phenyl and $R^3$ is dimethylamino. In another embodiment, $R^1$ is monosubstituted phenyl, e.g., selected from, among the substituents disclosed above in connection with the compounds of formula (I), and $R^3$ is dimethylamino. In another embodiment, $R^1$ is disubstituted phenyl, e.g., selected from among the substituents disclosed above in connection with the compounds of formula (I), and $R^3$ is dimethylamino.

In another embodiment, $R^2$ is methyl and $R^3$ is methyl. In another embodiment, $R^2$ is methyl and $R^3$ is ethyl. In another embodiment, $R^2$ is methyl and $R^3$ is iso-propyl. In another embodiment, $R^2$ is methyl and $R^3$ is tert-butyl. In another embodiment, $R^2$ is ethyl and $R^3$ is methyl. In another embodiment, $R^2$ is ethyl and $R^3$ is ethyl. In another embodiment, $R^2$ is ethyl and $R^3$ is iso-propyl. In another embodiment, $R^2$ is ethyl and $R^3$ is tert-butyl. In another embodiment, $R^2$ is iso-propyl and $R^3$ is methyl. In another embodiment, $R^2$ is iso-propyl and $R^3$ is ethyl. In another embodiment, $R^2$ is iso-propyl and $R^3$ is iso-propyl. In another embodiment, $R^2$ is iso-propyl and $R^3$ is tert-butyl. In another embodiment, $R^2$ is tert-butyl and $R^3$ is methyl. In another embodiment, $R^2$ is tert-butyl and $R^3$ is ethyl. In another embodiment, $R^2$ is tert-butyl and $R^3$ is iso-propyl. In another embodiment, $R^2$ is tert-butyl and $R^3$ is tert-butyl.

In another embodiment, $R^2$ is —C(=NOR$^4$)R$^5$ and $R^3$ is methyl. In another embodiment, $R^2$ is —C(=NOR$^4$)R$^5$, wherein at least one of $R^4$ and $R^5$ is methyl, and $R^3$ is methyl. In another embodiment, $R^2$ is —C(=NOR$^4$)R$^5$, wherein each of $R^4$ and $R^5$ is methyl, and $R^3$ is methyl. In another embodiment, $R^2$ is —C(=NOR$^4$)R$^5$, wherein one of $R^4$ and $R^5$ is methyl and the other is ethyl, and $R^3$ is methyl. In another embodiment, $R^2$ is —C(=NOR$^4$)R$^5$ and $R^3$ is ethyl. In another embodiment, $R^2$ is —C(=NOR$^4$)R$^5$, wherein at least one of $R^4$ and $R^5$ is methyl, and $R^3$ is ethyl. In another embodiment, $R^2$ is —C(=NOR$^4$)R$^5$, wherein each of $R^4$ and $R^5$ is methyl, and $R^3$ is ethyl. In another embodiment, $R^2$ is —C(=NOR$^4$)R$^5$, wherein one of $R^4$ and $R^5$ is methyl and the other is ethyl, and $R^3$ is ethyl. In another embodiment, $R^2$ is —C(=NOR$^4$)R$^5$ and $R^3$ is iso-propyl. In another embodiment, $R^2$ is —C(=NOR$^4$)R$^5$, wherein at least one of $R^4$ and $R^5$ is methyl, and $R^3$ is iso-propyl. In another embodiment, $R^2$ is —C(=NOR$^4$)R$^5$, wherein each of $R^4$ and $R^5$ is methyl, and $R^3$ is iso-propyl. In another embodiment, $R^2$ is —C(=NOR$^4$)R$^5$, wherein one of $R^4$ and $R^5$ is methyl and the other is ethyl, and $R^3$ is iso-propyl. In another embodiment, $R^2$ is —C(=NOR$^4$)R$^5$ and $R^3$ is tert-butyl. In another embodiment, $R^2$ is —C(=NOR$^4$)R$^5$, wherein at least one of $R^4$ and $R^5$ is methyl, and $R^3$ is tert-butyl. In another embodiment, $R^2$ is —C(=NOR$^4$)R$^5$, wherein each of $R^4$ and $R^5$ is methyl, and $R^3$ is tert-butyl. In another embodiment, $R^2$ is —C(=NOR$^4$)R$^5$, wherein one of $R^4$ and $R^5$ is methyl and the other is ethyl, and $R^3$ is tert-butyl.

In another embodiment, $R^2$ is methyl and $R^3$ is methoxy. In another embodiment, $R^2$ is methyl and $R^3$ is ethoxy. In another embodiment, $R^2$ is methyl and $R^3$ is iso-propoxy. In another embodiment, $R^2$ is methyl and $R^3$ is tert-butoxy. In another embodiment, $R^2$ is ethyl and $R^3$ is methoxy. In another embodiment, $R^2$ is ethyl and $R^3$ is ethoxy. In another embodiment, $R^2$ is ethyl and $R^3$ is iso-propoxy. In another embodiment, $R^2$ is ethyl and $R^3$ is tert-butoxy. In another embodiment, $R^2$ is iso-propyl and $R^3$ is methoxy. In another embodiment, $R^2$ is iso-propyl and $R^3$ is ethoxy. In another embodiment, $R^2$ is iso-propyl and $R^3$ is iso-propoxy. In another embodiment, $R^2$ is iso-propyl and $R^3$ is tert-butoxy. In another embodiment, $R^2$ is tert-butyl and $R^3$ is methoxy. In another embodiment, $R^2$ is tert-butyl and $R^3$ is ethoxy. In another embodiment, $R^2$ is tert-butyl and $R^3$ is iso-propoxy. In another embodiment, $R^2$ is tert-butyl and $R^3$ is tert-butoxy.

In another embodiment, $R^2$ is —C(=NOR$^4$)R$^5$ and $R^3$ is methoxy. In another embodiment, $R^2$ is —C(=NOR$^4$)R$^5$, wherein at least one of $R^4$ and $R^5$ is methyl, and $R^3$ is methoxy. In another embodiment, $R^2$ is —C(=NOR$^4$)R$^5$, wherein each of $R^4$ and $R^5$ is methyl, and $R^3$ is methoxy. In another embodiment, $R^2$ is —C(=NOR$^4$)R$^5$, wherein one of $R^4$ and $R^5$ is methyl and the other is ethyl, and $R^3$ is methoxy. In another embodiment, $R^2$ is —C(=NOR$^4$)R$^5$ and $R^3$ is ethoxy. In another embodiment, $R^2$ is —C(=NOR$^4$)R$^5$, wherein at least one of $R^4$ and $R^5$ is methyl, and $R^3$ is ethoxy. In another embodiment, $R^2$ is —C(=NOR$^4$)R$^5$, wherein each of $R^4$ and $R^5$ is methyl, and $R^3$ is ethoxy. In another embodiment, $R^2$ is —C(=NOR$^4$)R$^5$, wherein one of $R^4$ and $R^5$ is methyl and the other is ethyl, and $R^3$ is ethoxy. In another embodiment, $R^2$ is —C(=NOR$^4$)R$^5$ and $R^3$ is iso-propoxy. In another embodiment, $R^2$ is —C(=NOR$^4$)R$^5$, wherein at least one of $R^4$ and $R^5$ is methyl, and $R^3$ is iso-propoxy. In another embodiment, $R^2$ is —C(=NOR$^4$)R$^5$, wherein each of $R^4$ and $R^5$ is methyl, and $R^3$ is iso-propoxy. In another embodiment, $R^2$ is —C(=NOR$^4$)R$^5$, wherein one of $R^4$ and $R^5$ is methyl and the other is ethyl, and $R^3$ is iso-propoxy. In another embodiment, $R^2$ is —C(=NOR$^4$)R$^5$ and $R^3$ is tert-butoxy. In another embodiment, $R^2$ is —C(=NOR$^4$)R$^5$, wherein at least one of $R^4$ and $R^5$ is methyl, and $R^3$ is tert-butoxy. In another embodiment, $R^2$ is —C(=NOR$^4$)R$^5$, wherein each of $R^4$ and $R^5$ is methyl, and $R^3$ is tert-butoxy. In another embodiment, $R^2$ is —C(=NOR$^4$)R$^5$, wherein one of $R^4$ and $R^5$ is methyl and the other is ethyl, and $R^3$ is tert-butoxy.

In another embodiment, $R^2$ is methyl and $R^3$ is dimethylamino. In another embodiment, $R^2$ is ethyl and $R^3$ is dimethylamino. In another embodiment, $R^2$ is iso-propyl and $R^3$ is dimethylamino. In another embodiment, $R^2$ is tert-butyl and $R^3$ is dimethylamino. In another embodiment, $R^2$ is —C(=NOR$^4$)R$^5$ and $R^3$ is dimethylamino. In another embodiment, $R^2$ is —C(=NOR$^4$)R$^5$, wherein at least one of $R^4$ and $R^5$ is methyl, and $R^3$ is dimethylamino. In another embodiment, $R^2$ is —C(=NOR$^4$)R$^5$, wherein each of $R^4$ and $R^5$ is methyl, and $R^3$ is dimethylamino. In another embodiment, $R^2$ is —C(=NOR$^4$)R$^5$, wherein one of $R^4$ and $R^5$ is methyl and the other is ethyl, and $R^3$ is dimethylamino.

Another aspect of the disclosure provides a compound of formula (I'):

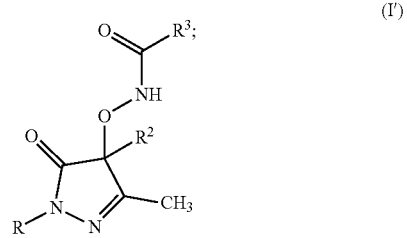

or a pharmaceutically acceptable salt thereof, wherein:
R, $R^2$, $R^3$, $R^4$, $R^5$, $R^6$, $R^7$ and $R^8$ are as defined above in connection with the compounds of formula (I).

In one embodiment, R is methyl and $R^2$ is methyl. In another embodiment, R is methyl and $R^2$ is ethyl. In another embodiment, R is ethyl and $R^2$ is methyl. In another embodiment, R is ethyl and $R^2$ is ethyl. In another embodiment, R is iso-propyl and $R^2$ is methyl. In another embodiment, R is iso-propyl and $R^2$ is ethyl. In another embodiment, R is methyl and $R^2$ is iso-propyl. In another embodiment, R is ethyl and $R^2$ is iso-propyl. In another embodiment, R is iso-propyl and $R^2$ is iso-propyl. In another embodiment, R is unsubstituted phenyl and $R^2$ is methyl. In another embodiment, R is unsubstituted phenyl and $R^2$ is ethyl. In another embodiment, R is unsubstituted phenyl and $R^2$ is iso-propyl. In another embodiment, R is methyl and $R^2$ is —C(=NOR$^4$)R$^5$. In another embodiment, R is methyl and $R^2$ is —C(=NOR$^4$)R$^5$, wherein at least one of $R^4$ and $R^5$ is methyl. In another embodiment, R is methyl and $R^2$ is —C(=NOR$^4$)R$^5$, wherein each of $R^4$ and $R^5$ is methyl. In another embodiment, R is methyl and $R^2$ is —C(=NOR$^4$)R$^5$, wherein one of $R^4$ and $R^5$ is methyl and the other is ethyl. In another embodiment, R is ethyl and $R^2$ is —C(=NOR$^4$)R$^5$. In another embodiment, R is ethyl and $R^2$ is —C(=NOR$^4$)R$^5$, wherein at least one of $R^4$ and $R^5$ is methyl. In another embodiment, R is ethyl and $R^2$ is —C(=NOR$^4$)R$^5$, wherein each of $R^4$ and $R^5$ is methyl. In another embodiment, R is ethyl and $R^2$ is —C(=NOR$^4$)R$^5$, wherein one of $R^4$ and $R^5$ is methyl and the other is ethyl. In another embodiment, R is iso-propyl and $R^2$ is —C(=NOR$^4$)R$^5$. In another embodiment, R is iso-propyl and $R^2$ is —C(=NOR$^4$)R$^5$, wherein at least one of $R^4$ and $R^5$ is methyl. In another embodiment, R is iso-propyl and $R^2$ is —C(=NOR$^4$)R$^5$, wherein each of $R^4$ and $R^5$ is methyl. In another embodiment, R is iso-propyl and $R^2$ is —C(=NOR$^4$)R$^5$, wherein one of $R^4$ and $R^5$ is methyl and the other is ethyl.

In another embodiment, R is unsubstituted phenyl and $R^2$ is —C(=NOR$^4$)R$^5$. In another embodiment, R is unsubstituted phenyl and $R^2$ is —C(=NOR$^4$)R$^5$, wherein at least one of $R^4$ and $R^5$ is methyl. In another embodiment, R is unsubstituted phenyl and $R^2$ is —C(=NOR$^4$)R$^5$, wherein each of $R^4$ and $R^5$ is methyl. In another embodiment, R is unsubstituted phenyl and $R^2$ is —C(=NOR$^4$)R$^5$, wherein one of $R^4$ and $R^5$ is methyl and the other is ethyl. In another embodiment, R is unsubstituted phenyl and $R^2$ is methyl. In another embodiment, R is unsubstituted phenyl and $R^2$ is ethyl. In another embodiment, R is unsubstituted phenyl and $R^2$ is iso-propyl. In another embodiment, R is unsubstituted phenyl and $R^2$ is tert-butyl. In another embodiment, R is unsubstituted phenyl and $R^2$ is —C(=NOR$^4$)R$^5$. In another embodiment, R is unsubstituted phenyl and $R^2$ is —C(=NOR$^4$)R$^5$, wherein at least one of $R^4$ and $R^5$ is methyl. In another embodiment, R is unsubstituted phenyl and $R^2$ is —C(=NOR$^4$)R$^5$, wherein each of $R^4$ and $R^5$ is methyl. In another embodiment, R is unsubstituted phenyl and $R^2$ is —C(=NOR$^4$)R$^5$, wherein one of $R^4$ and $R^5$ is methyl and the other is ethyl.

In another embodiment, R is methyl and $R^3$ is methyl. In another embodiment, R is ethyl and $R^3$ is methyl. In another embodiment, R is iso-propyl and $R^3$ is methyl. In another embodiment, R is tert-butyl and $R^3$ is methyl. In another embodiment, R is unsubstituted phenyl and $R^3$ is methyl. In another embodiment, R is methyl and $R^3$ is ethyl. In another embodiment, R is ethyl and $R^3$ is ethyl. In another embodiment, R is iso-propyl and $R^3$ is ethyl. In another embodiment, R is tert-butyl and $R^3$ is ethyl. In another embodiment, R is unsubstituted phenyl and $R^3$ is ethyl. In another embodiment, R is methyl and $R^3$ is iso-propyl. In another embodiment, R is ethyl and $R^3$ is iso-propyl. In another embodiment, R is iso-propyl and $R^3$ is iso-propyl. In another embodiment, R is tert-butyl and $R^3$ is iso-propyl. In another embodiment, R is unsubstituted phenyl and $R^3$ is iso-propyl. In another embodiment, R is methyl and $R^3$ is tert-butyl. In another embodiment, R is ethyl and $R^3$ is tert-butyl. In another embodiment, R is iso-propyl and $R^3$ is tert-butyl. In another embodiment, R is tert-butyl and $R^3$ is tert-butyl. In another embodiment, R is unsubstituted phenyl and $R^3$ is tert-butyl. In another embodiment, R is methyl and $R^3$ is methoxy. In another embodiment, R is ethyl and $R^3$ is methoxy. In another embodiment, R is iso-propyl and $R^3$ is methoxy. In another embodiment, R is tert-butyl and $R^3$ is methoxy. In another embodiment, R is unsubstituted phenyl and $R^3$ is methoxy. In another embodiment, R is methyl and $R^3$ is ethoxy. In another embodiment, R is ethyl and $R^3$ is ethoxy. In another embodiment, R is iso-propyl and $R^3$ is ethoxy. In another embodiment, R is tert-butyl and $R^3$ is ethoxy. In another embodiment, R is unsubstituted phenyl and $R^3$ is ethoxy. In another embodiment, R is methyl and $R^3$ is iso-propoxy. In another embodiment, R is ethyl and $R^3$ is iso-propoxy. In another embodiment, R is iso-propyl and $R^3$ is iso-propoxy. In another embodiment, R is tert-butyl and $R^3$ is iso-propoxy. In another embodiment, R is unsubstituted phenyl and $R^3$ is iso-propoxy. In another embodiment, R is methyl and $R^3$ is tert-butoxy. In another embodiment, R is ethyl and $R^3$ is tert-butoxy. In another embodiment, R is iso-propyl and $R^3$ is tert-butoxy. In another embodiment, R is tert-butyl and $R^3$ is tert-butoxy. In another embodiment, R is unsubstituted phenyl and $R^3$ is tert-butoxy. In another embodiment, R is methyl and $R^3$ is dimethylamino. In another embodiment, R is ethyl and $R^3$ is dimethylamino. In another embodiment, R is iso-propyl and $R^3$ is dimethylamino. In another embodiment, R is tert-butyl and $R^3$ is dimethylamino. In another embodiment, R is unsubstituted phenyl and $R^3$ is dimethylamino.

In another embodiment, $R^2$ is methyl and $R^3$ is methyl. In another embodiment, $R^2$ is methyl and $R^3$ is ethyl. In another embodiment, $R^2$ is methyl and $R^3$ is iso-propyl. In another embodiment, $R^2$ is methyl and $R^3$ is tert-butyl. In another embodiment, $R^2$ is ethyl and $R^3$ is methyl. In another embodiment, $R^2$ is ethyl and $R^3$ is ethyl. In another embodiment, $R^2$ is ethyl and $R^3$ is iso-propyl. In another embodiment, $R^2$ is ethyl and $R^3$ is tert-butyl. In another embodiment, $R^2$ is iso-propyl and $R^3$ is methyl. In another embodiment, $R^2$ is iso-propyl and $R^3$ is ethyl. In another embodiment, $R^2$ is iso-propyl and $R^3$ is iso-propyl. In another embodiment, $R^2$ is iso-propyl and $R^3$ is tert-butyl. In another embodiment, $R^2$ is tert-butyl and $R^3$ is methyl. In another embodiment, $R^2$ is tert-butyl and $R^3$ is ethyl. In another embodiment, $R^2$ is tert-butyl and $R^3$ is iso-propyl. In another embodiment, $R^2$ is tert-butyl and $R^3$ is tert-butyl.

In another embodiment, $R^2$ is —C(=NOR$^4$)R$^5$ and $R^3$ is methyl. In another embodiment, $R^2$ is —C(=NOR$^4$)R$^5$, wherein at least one of $R^4$ and $R^5$ is methyl, and $R^3$ is methyl. In another embodiment, $R^2$ is —C(=NOR$^4$)R$^5$, wherein each of $R^4$ and $R^5$ is methyl, and $R^3$ is methyl. In another embodiment, $R^2$ is —C(=NOR$^4$)R$^5$, wherein one of $R^4$ and $R^5$ is methyl and the other is ethyl, and $R^3$ is methyl. In another embodiment, $R^2$ is —C(=NOR$^4$)R$^5$ and $R^3$ is ethyl. In another embodiment, $R^2$ is —C(=NOR$^4$)R$^5$, wherein at least one of $R^4$ and $R^5$ is methyl, and $R^3$ is ethyl. In another embodiment, $R^2$ is —C(=NOR$^4$)R$^5$, wherein each of $R^4$ and $R^5$ is methyl, and $R^3$ is ethyl. In another embodiment, $R^2$ is —C(=NOR$^4$)R$^5$, wherein one of $R^4$ and $R^5$ is methyl and the other is ethyl, and $R^3$ is ethyl. In another embodiment, $R^2$ is —C(=NOR$^4$)R$^5$ and $R^3$ is iso-propyl. In another embodiment, $R^2$ is —C(=NOR$^4$)R$^5$, wherein at least one of $R^4$ and $R^5$ is methyl, and $R^3$ is iso-propyl. In another embodiment, $R^2$ is —C(=NOR$^4$)R$^5$, wherein each of $R^4$ and $R^5$ is methyl, and $R^3$ is iso-propyl. In another embodiment, $R^2$ is —C(=NOR$^4$)R$^5$, wherein one of $R^4$ and $R^5$ is methyl and the other is ethyl, and $R^3$ is iso-propyl. In another embodiment, $R^2$ is —C(=NOR$^4$)R$^5$ and $R^3$ is tert-butyl. In another embodiment, $R^2$ is —C(=NOR$^4$)R$^5$, wherein at least one of $R^4$ and $R^5$ is methyl, and $R^3$ is tert-butyl. In another embodiment, $R^2$ is —C(=NOR$^4$)R$^5$, wherein each of $R^4$ and $R^5$ is methyl, and $R^3$ is tert-butyl. In another embodiment, $R^2$ is —C(=NOR$^4$)R$^5$, wherein one of $R^4$ and $R^5$ is methyl and the other is ethyl, and $R^3$ is tert-butyl.

In another embodiment, $R^2$ is methyl and $R^3$ is methoxy. In another embodiment, $R^2$ is methyl and $R^3$ is ethoxy. In another embodiment, $R^2$ is methyl and $R^3$ is iso-propoxy. In another embodiment, $R^2$ is methyl and $R^3$ is tert-butoxy. In another embodiment, $R^2$ is ethyl and $R^3$ is methoxy. In another embodiment, $R^2$ is ethyl and $R^3$ is ethoxy. In another embodiment, $R^2$ is ethyl and $R^3$ is iso-propoxy. In another embodiment, $R^2$ is ethyl and $R^3$ is tert-butoxy. In another embodiment, $R^2$ is iso-propyl and $R^3$ is methoxy. In another embodiment, $R^2$ is iso-propyl and $R^3$ is ethoxy. In another embodiment, $R^2$ is iso-propyl and $R^3$ is iso-propoxy. In another embodiment, $R^2$ is iso-propyl and $R^3$ is tert-butoxy. In another embodiment, $R^2$ is tert-butyl and $R^3$ is methoxy. In another embodiment, $R^2$ is tert-butyl and $R^3$ is ethoxy. In another embodiment, $R^2$ is tert-butyl and $R^3$ is iso-propoxy. In another embodiment, $R^2$ is tert-butyl and $R^3$ is tert-butoxy.

In another embodiment, $R^2$ is —C(=NOR$^4$)R$^5$ and $R^3$ is methoxy. In another embodiment, $R^2$ is —C(=NOR$^4$)R$^5$, wherein at least one of $R^4$ and $R^5$ is methyl, and $R^3$ is methoxy. In another embodiment, $R^2$ is —C(=NOR$^4$)R$^5$, wherein each of $R^4$ and $R^5$ is methyl, and $R^3$ is methoxy. In another embodiment, $R^2$ is —C(=NOR$^4$)R$^5$, wherein one of $R^4$ and $R^5$ is methyl and the other is ethyl, and $R^3$ is methoxy. In another embodiment, $R^2$ is —C(=NOR$^4$)R$^5$ and $R^3$ is ethoxy. In another embodiment, $R^2$ is —C(=NOR$^4$)R$^5$, wherein at least one of $R^4$ and $R^5$ is methyl, and $R^3$ is ethoxy. In another embodiment, $R^2$ is —C(=NOR$^4$)R$^5$, wherein each of $R^4$ and $R^5$ is methyl, and $R^3$ is ethoxy. In another embodiment, $R^2$ is —C(=NOR$^4$)R$^5$, wherein one of $R^4$ and $R^5$ is methyl and the other is ethyl, and $R^3$ is ethoxy. In another embodiment, $R^2$ is —C(=NOR$^4$)R$^5$ and $R^3$ is iso-propoxy. In another embodiment, $R^2$ is —C(=NOR$^4$)R$^5$, wherein at least one of $R^4$ and $R^5$ is methyl, and $R^3$ is iso-propoxy. In another embodiment, $R^2$ is —C(=NOR$^4$)R$^5$, wherein each of $R^4$ and $R^5$ is methyl, and $R^3$ is iso-propoxy. In another embodiment, $R^2$ is —C(=NOR$^4$)R$^5$, wherein one of $R^4$ and $R^5$ is methyl and the other is ethyl, and $R^3$ is iso-propoxy. In another embodiment, $R^2$ is —C(=NOR$^4$)R$^5$ and $R^3$ is tert-butoxy. In another embodiment, $R^2$ is —C(=NOR$^4$)R$^5$ wherein at least one of $R^4$ and $R^5$ is methyl, and $R^3$ is tert-butoxy. In another embodiment, $R^2$ is —C(=NOR$^4$)R$^5$, wherein each of $R^4$ and $R^5$ is methyl, and $R^3$ is tert-butoxy. In another embodiment, $R^2$ is —C(=NOR$^4$)R$^5$, wherein one of $R^4$ and $R^5$ is methyl and the other is ethyl, and $R^3$ is tert-butoxy.

In another embodiment, $R^2$ is methyl and $R^3$ is dimethylamino. In another embodiment, $R^2$ is ethyl and $R^3$ is dimethylamino. In another embodiment, $R^2$ is iso-propyl and $R^3$ is dimethylamino. In another embodiment, $R^2$ is tert-butyl and $R^3$ is dimethylamino. In another embodiment, $R^2$ is —C(=NOR$^4$)R$^5$ and $R^3$ is dimethylamino. In another embodiment, $R^2$ is —C(=NOR$^4$)R$^5$, wherein at least one of $R^4$ and $R^5$ is methyl, and $R^3$ is dimethylamino. In another embodiment, $R^2$ is —C(=NOR$^4$)R$^5$, wherein each of $R^4$ and $R^5$ is methyl, and $R^3$ is dimethylamino. In another embodiment, $R^2$ is —C(=NOR$^4$)R$^5$, wherein one of $R^4$ and $R^5$ is methyl and the other is ethyl, and $R^3$ is dimethylamino.

Another aspect of the disclosure provides a compound of formula (II):

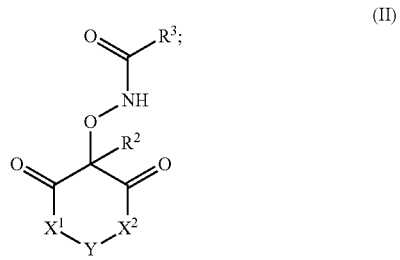

(II)

or a pharmaceutically acceptable salt thereof, wherein;

$R^2$ is selected from the group consisting of hydrogen, (C$_1$-C$_6$)alkyl, —C(=O)R$^4$, —C(=S)R$^4$, C(=NR$^4$)R$^5$, —C(=NOR$^4$)R$^5$, (5- or 6-membered)heteroaryl and (C$_6$-C$_{10}$)aryl;

$R^3$ is selected from the group consisting of hydrogen, (C$_1$-C$_6$)alkyl, (C$_6$-C$_{10}$)aryl, —NR$^6$R$^7$, and —OR$^8$;

$R^4$, $R^5$, $R^6$, $R^7$, and $R^8$ are each independently selected from the group consisting of hydrogen, (C$_1$-C$_6$)alkyl, (C$_1$-C$_6$)alkoxy, phenyl and benzyl;

$X^1$ and $X^2$ are each independently selected from the group consisting of O, NR$^9$, S, CR$^{10}$, and CR$^{10}$R$^{11}$;

Y is selected from the group consisting of C(=O), C(=S), C(=NR$^9$), and CR$^{10}$R$^{11}$;

$R^9$, $R^{10}$ and $R^{11}$ are each independently selected from the group consisting of hydrogen and (C$_1$-C$_6$)alkyl, wherein said alkyl, aryl, phenyl, benzyl, heteroalkyl, heterocycloalkyl and heteroaryl are unsubstituted or substituted with 1, 2, 3, 4 or 5 substituent(s) selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, (C$_5$-C$_7$)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl.

In one embodiment, $R^2$ is selected from (C$_1$-C$_6$)alkyl, —C(=O)R$^4$, —C(=S)R$^4$, C(=NR$^4$)R$^5$, —C(=NOR$^4$)R$^5$, (5- or 6-membered)heteroaryl or (C$_6$-C$_{10}$)aryl, wherein said alkyl, heteroaryl and aryl are unsubstituted or substituted with 1, 2 or 3 substituent(s) independently selected from among the substituents disclosed above in connection with the compounds of formula (II). In another embodiment, $R^2$ is selected from (C$_1$-C$_6$)alkyl, —C(=NOR$^4$)R$^5$, (5- or 6-membered)heteroaryl or phenyl, wherein said alkyl, heteroaryl and phenyl are unsubstituted or substituted with 1, 2 or 3 substituent(s) independently selected from among the substituents disclosed above in connection with the compounds of formula (II). In another embodiment, $R^2$ is selected from (C$_1$-C$_6$)alkyl and —C(=NOR$^4$)R$^5$.

In another embodiment, $R^2$ is (C$_1$-C$_6$)alkyl. In another embodiment, $R^2$ is methyl, ethyl, iso-propyl, or tert-butyl. In another embodiment, $R^2$ is methyl, ethyl, or iso-propyl. In another embodiment, $R^2$ is methyl, ethyl, or tert-butyl. In another embodiment, $R^2$ is methyl, iso-propyl, or tert-butyl. In another embodiment, $R^2$ is ethyl, iso-propyl, or tert-butyl. In another embodiment, $R^2$ is methyl or ethyl. In another embodiment, $R^2$ is methyl or iso-propyl. In another embodiment, $R^2$ is methyl or tert-butyl. In another embodiment, $R^2$ is ethyl or iso-propyl. In another embodiment, $R^2$ is ethyl or tert-butyl. In another embodiment, $R^2$ is iso-propyl or tert-butyl. In another embodiment, $R^2$ is methyl. In another embodiment, $R^2$ is ethyl. In another embodiment, $R^2$ is iso-propyl. In another embodiment, $R^2$ is tert-butyl.

In another embodiment, $R^2$ is —C(=NOR$^4$)R$^5$. In another embodiment, $R^2$ is —C(=NOR$^4$)R$^5$, wherein at least one of $R^4$ and $R^5$ is methyl. In another embodiment, $R^2$ is —C(=NOR$^4$)R$^5$, wherein each of $R^4$ and $R^5$ is methyl. In another embodiment, $R^2$ is —C(=NOR$^4$)R$^5$, wherein at least one of $R^4$ and $R^5$ is ethyl. In another embodiment, $R^2$ is —C(=NOR$^4$)R$^5$, wherein each of $R^4$ and $R^5$ is ethyl. In another embodiment, $R^2$ is —C(=NOR$^4$)R$^5$ wherein at least one of $R^4$ and $R^5$ is propyl. In another embodiment, $R^2$ is —C(=NOR$^4$)R$^5$, wherein each of $R^4$ and $R^5$ is propyl. In another embodiment, $R^2$ is —C(=NOR$^4$)R$^5$, wherein at least one of $R^4$ and $R^5$ is butyl. In another embodiment, $R^2$ is —C(=NOR$^4$)R$^5$, wherein each of $R^4$ and $R^5$ is butyl. In another embodiment, $R^2$ is —C(=NOR$^4$)R$^5$, wherein $R^4$ is methyl and $R^5$ is ethyl. In another embodiment, $R^2$ is —C(=NOR$^4$)R$^5$, wherein $R^4$ is ethyl and $R^5$ is methyl. In another embodiment, $R^2$ is —C(=NOR$^4$)R$^5$, wherein $R^4$ is methyl and $R^5$ is propyl. In another embodiment, $R^2$ is —C(=NOR$^4$)R$^5$, wherein $R^4$ is propyl and $R^5$ is methyl. In another embodiment, $R^2$ is —C(=NOR$^4$)R$^5$, wherein $R^4$ is methyl and $R^5$ is butyl. In another embodiment, $R^2$ is —C(=NOR$^4$)R$^5$, wherein $R^4$ is butyl and $R^5$ is methyl. In another embodiment, $R^2$ is —C(=NOR$^4$)R$^5$, wherein $R^4$ is ethyl and $R^5$ is propyl. In another embodiment, $R^2$ is —C(=NOR$^4$)R$^5$, wherein $R^4$ is propyl and $R^5$ is ethyl. In another embodiment, $R^2$ is —C(=NOR$^4$)R$^5$, wherein $R^4$ is propyl and $R^5$ is butyl. In another embodiment, $R^2$ is —C(=NOR$^4$)R$^5$, wherein $R^4$ is butyl and $R^5$ is propyl. In another embodiment, $R^2$ is —C(=NOR$^4$)R$^5$, wherein at least one of $R^4$ and $R^5$ is phenyl. In another embodiment, $R^2$ is —C(=NOR$^4$)R$^5$, wherein $R^4$ is phenyl and $R^5$ is methyl. In another embodiment, $R^2$ is —C(=NOR$^4$)R$^5$, wherein $R^4$ is phenyl and $R^5$ is ethyl. In another embodiment, $R^2$ is —C(=NOR$^4$)R$^5$, wherein at least one of $R^4$ and $R^5$ is phenyl substituted with a substituent selected from among the substituents disclosed above in connection with the compounds of formula (II). In another embodiment, $R^2$ is —C(=NOR$^4$)R$^5$, wherein $R^4$ is phenyl substituted with a substituent selected from among the substituents disclosed above in connection with the compounds of formula (II) and $R^5$ is methyl. In another embodiment, $R^2$ is —C(=NOR$^4$)R$^5$, wherein $R^4$ is phenyl substituted with a substituent selected from among the substituents disclosed above in connection with the compounds of formula (II) and $R^5$ is ethyl. In another embodiment, $R^2$ is —C(=NOR$^4$)R$^5$, wherein at least one of $R^4$ and $R^5$ is benzyl. In another embodiment, $R^2$ is —C(=NOR$^4$)R$^5$, wherein $R^4$ is benzyl and $R^5$ is methyl. In another embodiment, $R^2$ is —C(=NOR$^4$)R$^5$, wherein $R^4$ is benzyl and $R^5$ is ethyl.

In another embodiment, $R^2$ is unsubstituted phenyl. In another embodiment, $R^2$ is phenyl substituted with 1, 2 or 3 substituent(s) independently selected from halo, $(C_1-C_6)$alkyl, $(C_1-C_6)$alkoxy, $(C_1-C_{10})$alkylsulfonyl, $(C_1-C_6)$alkylsulfinyl, —C(=O)NR$^4$R$^5$ and —S(O)$_2$—NR$^6$R$^7$.

In another embodiment, R$^2$ is $(C_1-C_6)$alkyl, —C(=NOR$^4$)R$^5$, or phenyl. In another embodiment, R$^2$ is $(C_1-C_6)$alkyl or —C(=NOR$^4$)R$^5$. In another embodiment, R$^2$ is methyl, ethyl, ethylpropanoate, —(C=NOCH$_3$)CH$_3$, —(C=NOphenyl)CH$_3$, —(C=NO-4-bromophenyl)CH$_3$, —(C=NObenzyl)CH$_3$, —(C=NO-(2-methylpropyl))CH$_3$, —(C=NOethyl)CH$_3$, —(C=NOtert-butyl)CH$_3$, phenyl, 3-methylphenyl, 3-chlorophenyl, 4-chlorophenyl, 3-fluorophenyl, 4-fluorophenyl, 4-(methylsulfonyl)phenyl, 3-methoxyphenyl, 4-methoxyphenyl, 4-(methylsulfinyl)phenyl, 3-bromo-4-methoxyphenyl, 3,4-dimethoxyphenyl, 4-methoxy-3-methylphenyl, N,N-dimethylphenyl-1-sulfonamide, N,N-dimethylphenyl-1-carboxamide, or 5-phenyl-1,2,4-oxadiazol-3-yl. In another embodiment, R$^2$ is methyl, —(C=NOCH$_3$)CH$_3$, or phenyl. In another embodiment, R$^2$ is methyl or —(C=NOCH$_3$)CH$_3$.

In one embodiment, R$^3$ is $(C_1-C_6)$alkyl, phenyl, —NR$^6$R$^7$, or —OR$^8$. In another embodiment, R$^3$ is $(C_1-C_6)$alkyl, phenyl, —NR$^6$R$^7$, or $(C_1-C_6)$alkoxy. In another embodiment, R$^3$ is $(C_1-C_6)$alkyl, —NR$^6$R$^7$, or $(C_1-C_6)$alkoxy.

In another embodiment, R$^3$ is $(C_1-C_6)$alkyl. In another embodiment, R$^3$ is methyl, ethyl, iso-propyl, or tert-butyl. In another embodiment, R$^3$ is methyl, ethyl, or iso-propyl. In another embodiment, R$^3$ is methyl, ethyl, or tert-butyl. In another embodiment, R$^3$ is methyl, iso-propyl, or tert-butyl. In another embodiment, R$^3$ is ethyl, iso-propyl, or tert-butyl. In another embodiment, R$^3$ is methyl or ethyl. In another embodiment, R$^3$ is methyl or iso-propyl. In another embodiment, R$^3$ is methyl or tert-butyl. In another embodiment, R$^3$ is ethyl or iso-propyl. In another embodiment, R$^3$ is ethyl or tert-butyl. In another embodiment, R$^3$ is iso-propyl or tert-butyl. In another embodiment, R$^3$ is methyl. In another embodiment, R$^3$ is ethyl. In another embodiment, R$^3$ is iso-propyl, in another embodiment, R$^3$ is tert-butyl.

In another embodiment, R$^3$ is —NR$^6$R$^7$, wherein at least one of R$^6$ and R$^7$ is hydrogen. In another embodiment, R$^3$ is —NR$^6$R$^7$, wherein each of R$^6$ and R$^7$ is hydrogen. In another embodiment, R$^3$ is —NR$^6$R$^7$, wherein at least one of R$^6$ and R$^7$ is $(C_1-C_6)$alkyl. In another embodiment, R$^3$ is —NR$^6$R$^7$, wherein each of R$^6$ and R$^7$ is $(C_1-C_6)$alkyl. In another embodiment, R$^3$ is —NR$^6$R$^7$, wherein at least one of R$^6$ and R$^7$ is methyl. In another embodiment, R$^3$ is —NR$^6$R$^7$, wherein each of R$^6$ and R$^7$ is methyl. In another embodiment, R$^3$ is —NR$^6$R$^7$, wherein at least one of R$^6$ and R$^7$ is ethyl. In another embodiment, R$^3$ is —NR$^6$R$^7$, wherein each of R$^6$ and R$^7$ is ethyl. In another embodiment R$^3$ is —NR$^6$R$^7$, wherein at least one of R$^6$ and R$^7$ is propyl. In another embodiment, R$^3$ is —NR$^6$R$^7$, wherein each of R$^6$ and R$^7$ is propyl. In another embodiment, R$^3$ is —NR$^6$R$^7$, wherein at least one of R$^6$ and R$^7$ is butyl. In another embodiment, R$^3$ is —NR$^6$R$^7$, wherein each of R$^6$ and R$^7$ is butyl.

In another embodiment, R$^3$ is $(C_1-C_6)$alkoxy. In another embodiment, R$^3$ is methoxy, ethoxy, propoxy or butoxy. In another embodiment, R$^3$ is methoxy or ethoxy. In another embodiment, R$^3$ is methoxy or propoxy. In another embodiment, R$^3$ is methoxy or butoxy. In another embodiment, R$^3$ is ethoxy or propoxy. In another embodiment, R$^3$ is ethoxy or butoxy. In another embodiment, R$^3$ is propoxy or butoxy. In another embodiment, R$^3$ is methoxy. In another embodiment, R$^3$ is ethoxy. In another embodiment, R$^3$ is propoxy. In another embodiment, R$^3$ is butoxy.

In another embodiment, R$^3$ is unsubstituted or substituted phenyl, wherein the substituents are selected from among the substituents disclosed above in connection with compounds of formula (II). In another embodiment, R$^3$ is unsubstituted phenyl. In another embodiment, R$^3$ is phenyl substituted with a substituent selected from among the substituents disclosed above in connection with compounds of formula (II). In another embodiment, R$^3$ is methyl, tert-butyl, dimethylamino, methoxy, butoxy or phenyl. In another embodiment, R$^3$ is methyl, dimethylamino, methoxy or butoxy.

In one embodiment, at least one of X$^1$ and X$^2$ is O. In another embodiment, each of X$^1$ and X$^2$ are O. In another embodiment, at least one of X$^1$ and X$^2$ is NR$^9$. In another embodiment, each of X$^1$ and X$^2$ are NR$^9$. In another embodiment, at least one of X$^1$ and X$^2$ is NH. In another embodiment, each of X$^1$ and X$^2$ are NR$^9$, wherein R$^9$ is H. In another embodiment, at least one of X$^1$ and X$^2$ is NR$^9$, wherein R$^9$ is $(C_1-C_6)$alkyl. In another embodiment, each of X$^1$ and X$^2$ are NR$^9$, wherein R$^9$ is $(C_1-C_6)$alkyl. In another embodiment, at least one of X$^1$ and X$^2$ is NR$^9$, wherein R$^9$ is methyl. In another embodiment, each of X$^1$ and X$^2$ are NR$^9$, wherein R$^9$ is methyl. In another embodiment, at least one of X$^1$ and X$^2$ is NR$^9$, wherein R$^9$ is ethyl. In another embodiment, each of X$^1$ and X$^2$ are NR$^9$, wherein R$^9$ is ethyl. In another embodiment, at least one of X$^1$ and X$^2$ is NR$^9$, wherein R$^9$ is iso-propyl. In another embodiment, each of X$^1$ and X$^2$ are NR$^9$, wherein R$^9$ is iso-propyl. In another embodiment, at least one of X$^1$ and X$^2$ is NR$^9$, wherein R$^9$ is tert-butyl. In another embodiment, each of X$^1$ and X$^2$ are NR$^9$, wherein R$^9$ is tert-butyl. In another embodiment, at least one of X$^1$ and X$^2$ is CR$^{10}$R$^{11}$. In another embodiment, each of X$^1$ and X$^2$ are CR$^{10}$R$^{11}$. In another embodiment, at least one of X$^1$ and X$^2$ is CR$^{10}$R$^{11}$, wherein at least one of R$^{10}$ and R$^{11}$ is H. In another embodiment, at least one of X$^1$ and X$^2$ is CR$^{10}$R$^{11}$, wherein each of R$^{10}$ and R$^{11}$ is H. In another embodiment, at least one of X$^1$ and X$^2$ is CR$^{10}$R$^{11}$, wherein at least one of R$^{10}$ and R$^{11}$ is $(C_1-C_6)$alkyl. In another embodiment, at least one of X$^1$ and X$^2$ is CR$^{10}$R$^{11}$, wherein each of R$^{10}$ and R$^{11}$ is $(C_1-C_6)$alkyl. In another embodiment, at least one of X$^1$ and X$^2$ is CR$^{10}$R$^{11}$, wherein at least one of R$^{10}$ and R$^{11}$ is methyl. In another embodiment, at least one of X$^1$ and X$^2$ is CR$^{10}$R$^{11}$, wherein each of R$^{10}$ and R$^{11}$ is methyl. In another embodiment, at least one of X$^1$ and X$^2$ is CR$^{10}$R$^{11}$, wherein at least one of R$^{10}$ and R$^{11}$ is ethyl. In another embodiment, at least one of X$^1$ and X$^2$ is CR$^{10}$R$^{11}$, wherein each of R$^{10}$ and R$^{11}$ is ethyl. In another embodiment, at least one of X$^1$ and X$^2$ is CR$^{10}$R$^{11}$, wherein at least one of R$^{10}$ and R$^{11}$ is iso-propyl. In another embodiment, at least one of X$^1$ and X$^2$ is CR$^{10}$R$^{11}$, wherein each of R$^{10}$ and R$^{11}$ is iso-propyl. In another embodiment, at least one of X$^1$ and X$^2$ is CR$^{10}$R$^{11}$, wherein at least one of R$^{10}$ and R$^{11}$ is tert-butyl. In another embodiment, at least one of X$^1$ and X$^2$ is CR$^{10}$R$^{11}$, wherein each of R$^{10}$ and R$^{11}$ is tert-butyl.

In one embodiment, Y is C(=O). In another embodiment, Y is C(=S). In another embodiment, Y is C(=NR$^9$). In another embodiment, Y is C(=NR$^9$), wherein R$^9$ is H. In another embodiment, Y is C(=NR$^9$), wherein R$^9$ is $(C_1-C_6)$alkyl. In another embodiment, Y is C(=NR$^9$), wherein R$^9$ is methyl. In another embodiment, Y is CR$^{10}$R$^{11}$. In another embodiment, Y is CR$^{10}$R$^{11}$, wherein at least one of R$^{10}$ and R$^{11}$ is H. In another embodiment, Y is CR$^{10}$R$^{11}$, wherein each of R$^{10}$ and R$^{11}$ is H. In another embodiment, Y is CR$^{10}$R$^{11}$, wherein at least one of R$^{10}$ and R$^{11}$ is $(C_1-C_6)$alkyl. In another embodiment, Y is CR$^{10}$R$^{11}$, wherein each of R$^{10}$ and R$^{11}$ is $(C_1-C_6)$alkyl. In another embodiment, Y is CR$^{10}$R$^{11}$, wherein at least one of R$^{10}$ and R$^{11}$ is methyl. In another embodiment, Y is $CR^{10}R^{11}$, wherein each of $R^{10}$ and $R^{11}$ is methyl. In another embodiment, Y is $CR^{10}R^{11}$, wherein at least one of $R^{10}$ and $R^{11}$ is ethyl. In another embodiment, Y is $CR^{10}R^{11}$, wherein each of $R^{10}$ and $R^{11}$ is ethyl. In another embodiment, Y is $CR^{10}R^{11}$, wherein at least one of $R^{10}$ and $R^{11}$ is iso-propyl. In another embodiment, Y is $CR^{10}R^{11}$, wherein each of $R^{10}$ and $R^{11}$ is iso-propyl. In another embodiment, Y is $CR^{10}R^{11}$, wherein at least one of $R^{10}$ and $R^{11}$ is tert-butyl. In another embodiment, Y is $CR^{10}R^{11}$, wherein each of $R^{10}$ and $R^{11}$ is tert-butyl.

In one embodiment, at least one of $X^1$ and $X^2$ is O and Y is $CR^{10}R^{11}$. In another embodiment, at least one of $X^1$ and $X^2$ is O and Y is $CR^{10}R^{11}$, wherein at least one of $R^{10}$ and $R^{11}$ is H. In another embodiment, at least one of $X^1$ and $X^2$ is O and Y is $CR^{10}R^{11}$, wherein each of $R^{10}$ and $R^{11}$ is H. In another embodiment, at least one of $X^1$ and $X^2$ is O and Y is $CR^{10}R^{11}$, wherein at least one of $R^{10}$ and $R^{11}$ is $(C_1-C_6)$alkyl. In another embodiment, at least one of $X^1$ and $X^2$ is O and Y is $CR^{10}R^{11}$, wherein each of $R^{10}$ and $R^{11}$ is $(C_1-C_6)$alkyl. In another embodiment, at least one of $X^1$ and $X^2$ is O and Y is $CR^{10}R^{11}$, wherein at least one of $R^{10}$ and $R^{11}$ is methyl. In another embodiment, at least one of $X^1$ and $X^2$ is O and Y is $CR^{10}R^{11}$, wherein each of $R^{10}$ and $R^{11}$ is methyl.

In another embodiment, each of $X^1$ and $X^2$ are O and Y is $CR^{10}R^{11}$. In another embodiment, each of $X^1$ and $X^2$ are O and Y is $CR^{10}R^{11}$, wherein at least one of $R^{10}$ and $R^{11}$ is H. In another embodiment, each of $X^1$ and $X^2$ are O and Y is $CR^{10}R^{11}$, wherein each of $R^{10}$ and $R^{11}$ is H. In another embodiment, each of $X^1$ and $X^2$ are O and Y is $CR^{10}R^{11}$, wherein at least one of $R^{10}$ and $R^{11}$ is $(C_1-C_6)$alkyl. In another embodiment, each of $X^1$ and $X^2$ are O and Y is $CR^{10}R^{11}$, wherein each of $R^{10}$ and $R^{11}$ is $(C_1-C_6)$alkyl. In another embodiment, each of $X^1$ and $X^2$ are O and Y is $CR^{10}R^{11}$, wherein at least one of $R^{10}$ and $R^{11}$ is methyl. In another embodiment, each of $X^1$ and $X^2$ are O and Y is $CR^{10}R^{11}$, wherein each of $R^{10}$ and $R^{11}$ is methyl.

In another embodiment, at least one of $X^1$ and $X^2$ is $NR^9$ and Y is $C(=O)$. In another embodiment, each of $X^1$ and $X^2$ are $NR^9$ and Y is $C(=O)$. In another embodiment, at least one of $X^1$ and $X^2$ is NH and Y is $C(=O)$. In another embodiment, each of $X^1$ and $X^2$ are NH and Y is $C(=O)$. In another embodiment, at least one of $X^1$ and $X^2$ is $N(C_1-C_6)$alkyl and Y is $C(=O)$. In another embodiment, each of $X^1$ and $X^2$ are $N(C_1-C_6)$alkyl and Y is $C(=O)$. In another embodiment, at least one of $X^1$ and $X^2$ is $N-CH_3$ and Y is $C(=O)$. In another embodiment, each of $X^1$ and $X^2$ are $N-CH_3$ and Y is $C(=O)$. In another embodiment, at least one of $X^1$ and $X^2$ is $CR^{10}R^{11}$ and Y is $C(=O)$. In another embodiment, each of $X^1$ and $X^2$ are $CR^{10}R^{11}$ and Y is $C(=O)$.

In another embodiment, $R^2$ is methyl and $R^3$ is methyl. In another embodiment, $R^2$ is methyl and $R^3$ is ethyl. In another embodiment, $R^2$ is methyl and $R^3$ is iso-propyl. In another embodiment, $R^2$ is methyl and $R^3$ is tert-butyl. In another embodiment, $R^2$ is ethyl and $R^3$ is methyl. In another embodiment, $R^2$ is ethyl and $R^3$ is ethyl. In another embodiment, $R^2$ is ethyl and $R^3$ is iso-propyl. In another embodiment, $R^2$ is ethyl and $R^3$ is tert-butyl. In another embodiment, $R^2$ is iso-propyl and $R^3$ is methyl. In another embodiment, $R^2$ is iso-propyl and $R^3$ is ethyl. In another embodiment, $R^2$ is iso-propyl and $R^3$ is iso-propyl. In another embodiment, $R^2$ is iso-propyl and $R^3$ is tert-butyl. In another embodiment, $R^2$ is tert-butyl and $R^3$ is methyl. In another embodiment, $R^2$ is tert-butyl and $R^3$ is ethyl. In another embodiment, $R^2$ is tert-butyl and $R^3$ is iso-propyl. In another embodiment, $R^2$ is tert-butyl and $R^3$ is tert-butyl.

In another embodiment, $R^2$ is $-C(=NOR^4)R^5$ and $R^3$ is methyl. In another embodiment, $R^2$ is $-C(=NOR^4)R^5$, wherein at least one of $R^4$ and $R^5$ is methyl, and $R^3$ is methyl. In another embodiment, $R^2$ is $-C(=NOR^4)R^5$, wherein each of $R^4$ and $R^5$ is methyl, and $R^3$ is methyl. In another embodiment, $R^2$ is $-C(=NOR^4)R^5$, wherein one of $R^4$ and $R^5$ is methyl and the other is ethyl, and $R^3$ is methyl. In another embodiment, $R^2$ is $-C(=NOR^4)R^5$ and $R^3$ is ethyl. In another embodiment, $R^2$ is $-C(=NOR^4)R^5$, wherein at least one of $R^4$ and $R^5$ is methyl, and $R^3$ is ethyl. In another embodiment, $R^2$ is $-C(=NOR^4)R^5$, wherein each of $R^4$ and $R^5$ is methyl, and $R^3$ is ethyl. In another embodiment, $R^2$ is $-C(=NOR^4)R^5$, wherein one of $R^4$ and $R^5$ is methyl and the other is ethyl, and $R^3$ is ethyl. In another embodiment, $R^2$ is $-C(=NOR^4)R^5$ and $R^3$ is iso-propyl. In another embodiment, $R^2$ is $-C(=NOR^4)R^5$, wherein at least one of $R^4$ and $R^5$ is methyl, and $R^3$ is iso-propyl. In another embodiment, $R^2$ is $-C(=NOR^4)R^5$, wherein each of $R^4$ and $R^5$ is methyl, and $R^3$ is iso-propyl. In another embodiment, $R^2$ is $-C(=NOR^4)R^5$, wherein one of $R^4$ and $R^5$ is methyl and the other is ethyl, and $R^3$ is iso-propyl. In another embodiment, $R^2$ is $-C(=NOR^4)R^5$ and $R^3$ is tert-butyl. In another embodiment, $R^2$ is $-C(=NOR^4)R^5$, wherein at least one of $R^4$ and $R^5$ is methyl, and $R^3$ is tert-butyl. In another embodiment, $R^2$ is $-C(=NOR^4)R^5$, wherein each of $R^4$ and $R^5$ is methyl, and $R^3$ is tert-butyl. In another embodiment, $R^2$ is $-C(=NOR^4)R^5$, wherein one of $R^4$ and $R^5$ is methyl and the other is ethyl, and $R^3$ is tert-butyl.

In another embodiment, $R^2$ is methyl and $R^3$ is methoxy. In another embodiment, $R^2$ is methyl and $R^3$ is ethoxy. In another embodiment, $R^2$ is methyl and $R^3$ is iso-propoxy. In another embodiment, $R^2$ is methyl and $R^3$ is tert-butoxy. In another embodiment, $R^2$ is ethyl and $R^3$ is methoxy. In another embodiment, $R^2$ is ethyl and $R^3$ is ethoxy. In another embodiment, $R^2$ is ethyl and $R^3$ is iso-propoxy. In another embodiment, $R^2$ is ethyl and $R^3$ is tert-butoxy. In another embodiment, $R^2$ is iso-propyl and $R^3$ is methoxy. In another embodiment, $R^2$ is iso-propyl and $R^3$ is ethoxy. In another embodiment, $R^2$ is iso-propyl and $R^3$ is iso-propoxy. In another embodiment, $R^2$ is iso-propyl and $R^3$ is tert-butoxy. In another embodiment, $R^2$ is tert-butyl and $R^3$ is methoxy. In another embodiment, $R^2$ is tert-butyl and $R^3$ is ethoxy. In another embodiment, $R^2$ is tert-butyl and $R^3$ is iso-propoxy. In another embodiment, $R^2$ is tert-butyl and $R^3$ is tert-butoxy.

In another embodiment, $R^2$ is $-C(=NOR^4)R^5$ and $R^3$ is methoxy. In another embodiment, $R^2$ is $-C(=NOR^4)R^5$, wherein at least one of $R^4$ and $R^5$ is methyl, and $R^3$ is methoxy. In another embodiment, $R^2$ is $-C(=NOR^4)R^5$, wherein each of $R^4$ and $R^5$ is methyl, and $R^3$ is methoxy. In another embodiment, $R^2$ is $-C(=NOR^4)R^5$, wherein one of $R^4$ and $R^5$ is methyl and the other is ethyl, and $R^3$ is methoxy. In another embodiment, $R^2$ is $-C(=NOR^4)R^5$ and $R^3$ is ethoxy. In another embodiment, $R^2$ is $-C(=NOR^4)R^5$, wherein at least one of $R^4$ and $R^5$ is methyl, and $R^3$ is ethoxy. In another embodiment, $R^2$ is $-C(=NOR^4)R^5$, wherein each of $R^4$ and $R^5$ is methyl, and $R^3$ is ethoxy. In another embodiment, $R^2$ is $-C(=NOR^4)R^5$, wherein one of $R^4$ and $R^5$ is methyl and the other is ethyl, and $R^3$ is ethoxy. In another embodiment, $R^2$ is $-C(=NOR^4)R^5$ and $R^3$ is iso-propoxy. In another embodiment, $R^2$ is $-C(=NOR^4)R^5$, wherein at least one of $R^4$ and $R^5$ is methyl, and $R^3$ is iso-propoxy. In another embodiment, $R^2$ is $-C(=NOR^4)R^5$, wherein each of $R^4$ and $R^5$ is methyl, and $R^3$ is iso-propoxy. In another embodiment, $R^2$ is $-C(=NOR^4)R^5$, wherein one of $R^4$ and $R^5$ is methyl and the other is ethyl, and $R^3$ is iso-propoxy. In another embodiment, $R^2$ is —C(=NOR$^4$)R$^5$ and R$^3$ is tert-butoxy. In another embodiment, R$^2$ is —C(=NOR$^4$)R$^5$, wherein at least one of R$^4$ and R$^5$ is methyl, and R$^3$ is tert-butoxy. In another embodiment, R$^2$ is —C(=NOR$^4$)R$^5$, wherein each of R$^4$ and R$^5$ is methyl, and R$^3$ is tert-butoxy. In another embodiment, R$^2$ is —C(=NOR$^4$)R$^5$, wherein one of R$^4$ and R$^5$ is methyl and the other is ethyl, and R$^3$ is tert-butoxy.

In another embodiment, R$^2$ is methyl and R$^3$ is dimethylamino. In another embodiment, R$^2$ is ethyl and R$^3$ is dimethylamino. In another embodiment, R$^2$ is iso-propyl and R$^3$ is dimethylamino. In another embodiment, R$^2$ is tert-butyl and R$^3$ is dimethylamino. In another embodiment, R$^2$ is —C(=NOR$^4$)R$^5$ and R$^3$ is dimethylamino. In another embodiment, R$^2$ is —C(=NOR$^4$)R$^5$, wherein at least one of R$^4$ and R$^5$ is methyl, and R$^3$ is dimethylamino. In another embodiment, R$^2$ is —C(=NOR$^4$)R$^5$, wherein each of R$^4$ and R$^5$ is methyl, and R$^3$ is dimethylamino. In another embodiment, R$^2$ is —C(=NOR$^4$)R$^5$, wherein one of R$^4$ and R$^5$ is methyl and the other is ethyl, and R$^3$ is dimethylamino.

Another aspect of the disclosure provides a compound of formula (II'):

(II')

or a pharmaceutically acceptable salt thereof, wherein:
R$^2$, R$^3$, R$^4$, R$^5$, R$^6$, R$^7$, R$^8$ and R$^9$ are as defined above in connection with the compounds of formula (II).

In another embodiment, R$^2$ is methyl and R$^3$ is methyl. In another embodiment, R$^2$ is methyl and R$^3$ is ethyl. In another embodiment, R$^2$ is methyl and R$^3$ is iso-propyl. In another embodiment, R$^2$ is methyl and R$^3$ is tert-butyl. In another embodiment, R$^2$ is ethyl and R$^3$ is methyl. In another embodiment, R$^2$ is ethyl and R$^3$ is ethyl. In another embodiment, R$^2$ is ethyl and R$^3$ is iso-propyl. In another embodiment, R$^2$ is ethyl and R$^3$ is tert-butyl. In another embodiment, R$^2$ is iso-propyl and R$^3$ is methyl. In another embodiment, R$^2$ is iso-propyl and R$^3$ is ethyl. In another embodiment, R$^2$ is iso-propyl and R$^3$ is iso-propyl. In another embodiment, R$^2$ is iso-propyl and R$^3$ is tert-butyl. In another embodiment, R$^2$ is tert-butyl and R$^3$ is methyl. In another embodiment, R$^2$ is tert-butyl and R$^3$ is ethyl. In another embodiment, R$^2$ is tert-butyl and R$^3$ is iso-propyl. In another embodiment, R$^2$ is tert-butyl and R$^3$ is tert-butyl.

In another embodiment, R$^2$ is —C(=NOR$^4$)R$^5$ and R$^3$ is methyl. In another embodiment, R$^2$ is —C(=NOR$^4$)R$^5$, wherein at least one of R$^4$ and R$^5$ is methyl, and R$^3$ is methyl. In another embodiment, R$^2$ is —C(=NOR$^4$)R$^5$, wherein each of R$^4$ and R$^5$ is methyl, and R$^3$ is methyl. In another embodiment, R$^2$ is —C(=NOR$^4$)R$^5$, wherein one of R$^4$ and R$^5$ is methyl and the other is ethyl, and R$^3$ is methyl. In another embodiment, R$^2$ is —C(=NOR$^4$)R$^5$ and R$^3$ is ethyl. In another embodiment, R$^2$ is —C(=NOR$^4$)R$^5$, wherein at least one of R$^4$ and R$^5$ is methyl, and R$^3$ is ethyl. In another embodiment, R$^2$ is —C(=NOR$^4$)R$^5$, wherein each of R$^4$ and R$^5$ is methyl, and R$^3$ is ethyl. In another embodiment, R$^2$ is —C(=NOR$^4$)R$^5$, wherein one of R$^4$ and R$^5$ is methyl and the other is ethyl, and R$^3$ is ethyl. In another embodiment, R$^2$ is —C(=NOR$^4$)R$^5$ and R$^3$ is iso-propyl. In another embodiment, R$^2$ is —C(=NOR$^4$)R$^5$, wherein at least one of R$^4$ and R$^5$ is methyl, and R$^3$ is iso-propyl. In another embodiment, R$^2$ is —C(=NOR$^4$)R$^5$, wherein each of R$^4$ and R$^5$ is methyl, and R$^3$ is iso-propyl. In another embodiment, R$^2$ is —C(=NOR$^4$)R$^5$, wherein one of R$^4$ and R$^5$ is methyl and the other is ethyl, and R$^3$ is iso-propyl. In another embodiment, R$^2$ is —C(=NOR$^4$)R$^5$ and R$^3$ is tert-butyl. In another embodiment, R$^2$ is —C(=NOR$^4$)R$^5$, wherein at least one of R$^4$ and R$^5$ is methyl, and R$^3$ is tert-butyl. In another embodiment, R$^2$ is —C(=NOR$^4$)R$^5$, wherein each of R$^4$ and R$^5$ is methyl, and R$^3$ is tert-butyl. In another embodiment, R$^2$ is —C(=NOR$^4$)R$^5$, wherein one of R$^4$ and R$^5$ is methyl and the other is ethyl, and R$^3$ is tert-butyl.

In another embodiment, R$^2$ is methyl and R$^3$ is methoxy. In another embodiment, R$^2$ is methyl and R$^3$ is ethoxy. In another embodiment, R$^2$ is methyl and R$^3$ is iso-propoxy. In another embodiment, R$^2$ is methyl and R$^3$ is tert-butoxy. In another embodiment, R$^2$ is ethyl and R$^3$ is methoxy. In another embodiment, R$^2$ is ethyl and R$^3$ is ethoxy. In another embodiment, R$^2$ is ethyl and R$^3$ is iso-propoxy. In another embodiment, R$^2$ is ethyl and R$^3$ is tert-butoxy. In another embodiment, R$^2$ is iso-propyl and R$^3$ is methoxy. In another embodiment, R$^2$ is iso-propyl and R$^3$ is ethoxy. In another embodiment, R$^2$ is iso-propyl and R$^3$ is iso-propoxy. In another embodiment, R$^2$ is iso-propyl and R$^3$ is tert-butoxy. In another embodiment, R$^2$ is tert-butyl and R$^3$ is methoxy. In another embodiment, R$^2$ is tert-butyl and R$^3$ is ethoxy. In another embodiment, R$^2$ is tert-butyl and R$^3$ is iso-propoxy. In another embodiment, R$^2$ is tert-butyl and R$^3$ is tert-butoxy.

In another embodiment, R$^2$ is —C(=NOR$^4$)R$^5$ and R$^3$ is methoxy. In another embodiment, R$^2$ is —C(=NOR$^4$)R$^5$, wherein at least one of R$^4$ and R$^5$ is methyl, and R$^3$ is methoxy. In another embodiment, R$^2$ is —C(=NOR$^4$)R$^5$, wherein each of R$^4$ and R$^5$ is methyl, and R$^3$ is methoxy. In another embodiment, R$^2$ is —C(=NOR$^4$)R$^5$, wherein one of R$^4$ and R$^5$ is methyl and the other is ethyl, and R$^3$ is methoxy. In another embodiment, R$^2$ is —C(=NOR$^4$)R$^5$ and R$^3$ is ethoxy. In another embodiment, R$^2$ is —C(=NOR$^4$)R$^5$, wherein at least one of R$^4$ and R$^5$ is methyl, and R$^3$ is ethoxy. In another embodiment, R$^2$ is —C(=NOR$^4$)R$^5$, wherein each of R$^4$ and R$^5$ is methyl, and R$^3$ is ethoxy. In another embodiment, R$^2$ is —C(=NOR$^4$)R$^5$, wherein one of R$^4$ and R$^5$ is methyl and the other is ethyl, and R$^3$ is ethoxy. In another embodiment, R$^2$ is —C(=NOR$^4$)R$^5$ and R$^3$ is iso-propoxy. In another embodiment, R$^2$ is —C(=NOR$^4$)R$^5$, wherein at least one of R$^4$ and R$^5$ is methyl, and R$^3$ is iso-propoxy. In another embodiment, R$^2$ is —C(=NOR$^4$)R$^5$, wherein each of R$^4$ and R$^5$ is methyl, and R$^3$ is iso-propoxy. In another embodiment, R$^2$ is —C(=NOR$^4$)R$^5$, wherein one of R$^4$ and R$^5$ is methyl and the other is ethyl, and R$^3$ is iso-propoxy. In another embodiment, R$^2$ is —C(=NOR$^4$)R$^5$ and R$^3$ is tert-butoxy. In another embodiment, R$^2$ is —C(=NOR$^4$)R$^5$, wherein at least one of R$^4$ and R$^5$ is methyl, and R$^3$ is tert-butoxy. In another embodiment, R$^2$ is —C(=NOR$^4$)R$^5$, wherein each of R$^4$ and R$^5$ is methyl, and R$^3$ is tert-butoxy. In another embodiment, R$^2$ is —C(=NOR$^4$)R$^5$, wherein one of R$^4$ and R$^5$ is methyl and the other is ethyl, and R$^3$ is tert-butoxy.

In another embodiment, R$^2$ is methyl and R$^3$ is dimethylamino. In another embodiment, R$^2$ is ethyl and R$^3$ is dimethylamino. In another embodiment, R$^2$ is iso-propyl and R$^3$ is dimethylamino. In another embodiment, R$^2$ is tert-butyl and R$^3$ is dimethylamino. In another embodiment, $R^2$ is —C(=NOR$^4$)R$^5$ and R$^3$ is dimethylamino. In another embodiment, R$^2$ is —C(=NOR$^4$)R$^5$, wherein at least one of R$^4$ and R$^5$ is methyl, and R$^3$ is dimethylamino. In another embodiment, R$^2$ is —C(=NOR$^4$)R$^5$, wherein each of R$^4$ and R$^5$ is methyl, and R$^3$ is dimethylamino. In another embodiment, R$^2$ is —C(=NOR$^4$)R$^5$, wherein one of R$^4$ and R$^5$ is methyl and the other is ethyl, and R$^3$ is dimethylamino.

Another aspect of the disclosure provides a compound of formula (III):

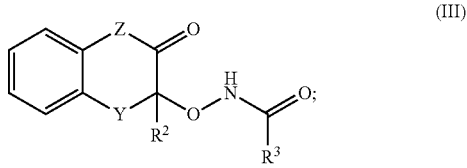

(III)

or a pharmaceutically acceptable salt thereof, wherein:

R$^2$ is selected from the group consisting of hydrogen, (C$_1$-C$_6$)alkyl, —C(=O)R$^4$, —C(=S)R$^4$, C(=NR$^4$)R$^5$, —C(=NOR$^4$)R$^5$, (5- or 6-membered)heteroaryl and (C$_6$-C$_{10}$)aryl;

R$^3$ is selected from the group consisting of hydrogen, (C$_1$-C$_6$)alkyl, (C$_6$-C$_{10}$)aryl, —NR$^6$R$^7$, and —OR$^8$;

R$^4$, R$^5$, R$^6$, R$^7$, and R$^8$ are each independently selected from the group consisting of hydrogen, (C$_1$-C$_6$)alkyl, (C$_1$-C$_6$)alkoxy, phenyl and benzyl;

Y is selected from the group consisting of C(=O), C(=S), C(=NR$^9$), and CR$^{10}$R$^{11}$;

Z is selected from the group consisting of O and S; and

R$^9$, R$^{10}$ and R$^{11}$ are each independently selected from the group consisting of hydrogen and (C$_1$-C$_6$)alkyl;

wherein said alkyl, aryl, phenyl, benzyl, heteroalkyl, heterocycloalkyl and heteroaryl are unsubstituted or substituted with 1, 2, 3, 4 or 5 substituent(s) selected from, halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)—(C$_5$-C$_7$)heterocycloalkyl, (C$_5$-C$_7$)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$—(C$_5$-C$_7$)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl.

In one embodiment, R$^2$ is (C$_1$-C$_6$)alkyl, —C(=O)R$^4$, —C(=S)R$^4$, C(=NR$^4$)R$^5$, —C(=NOR$^4$)R$^5$, (5- or 6-membered)heteroaryl or (C$_6$-C$_{10}$)aryl, wherein said alkyl, heteroaryl and aryl are unsubstituted or substituted with 1, 2 or 3 substituent(s) independently selected from among the substituents disclosed above in connection with the compounds of formula (III). In another embodiment, R$^2$ is (C$_1$-C$_6$)alkyl, —C(=NOR$^4$)R$^5$, (5- or 6-membered)heteroaryl or phenyl, wherein said alkyl, heteroaryl and phenyl are unsubstituted or substituted with 1, 2 or 3 substituent(s) independently selected from among the substituents disclosed above in connection with the compounds of formula (III). In another embodiment, R$^2$ is (C$_1$-C$_6$)alkyl or —C(=NOR$^4$)R$^5$.

In another embodiment, R$^2$ is (C$_1$-C$_6$)alkyl. In another embodiment, R$^2$ is methyl, ethyl, iso-propyl, or tert-butyl. In another embodiment, R$^2$ is methyl, ethyl, or iso-propyl. In another embodiment, R$^2$ is methyl, ethyl, or tert-butyl. In another embodiment, R$^2$ is methyl, iso-propyl, or tert-butyl. In another embodiment, R$^2$ is ethyl, iso-propyl, or tert-butyl. In another embodiment, R$^2$ is methyl or ethyl. In another embodiment, R$^2$ is methyl or iso-propyl. In another embodiment, R$^2$ is methyl or tert-butyl. In another embodiment, R$^2$ is ethyl or iso-propyl. In another embodiment, R$^2$ is ethyl or tert-butyl. In another embodiment, R$^2$ is iso-propyl or tert-butyl. In another embodiment, R$^2$ is methyl. In another embodiment, R$^2$ is ethyl. In another embodiment, R$^2$ is iso-propyl. In another embodiment, R$^2$ is tert-butyl.

In another embodiment, R$^2$ is —C(=NOR$^4$)R$^5$. In another embodiment, R$^2$ is —C(=NOR$^4$)R$^5$, wherein at least one of R$^4$ and R$^5$ is methyl. In another embodiment, R$^2$ is —C(=NOR$^4$)R$^5$, wherein each of R$^4$ and R$^5$ is methyl. In another embodiment, R$^2$ is —C(=NOR$^4$)R$^5$, wherein at least one of R$^4$ and R$^5$ is ethyl. In another embodiment, R$^2$ is —C(=NOR$^4$)R$^5$, wherein each of R$^4$ and R$^5$ is ethyl. In another embodiment, R$^2$ is —C(=NOR$^4$)R$^5$, wherein at least one of R$^4$ and R$^5$ is propyl. In another embodiment, R$^2$ is —C(=NOR$^4$)R$^5$, wherein each of R$^4$ and R$^5$ is propyl. In another embodiment, R$^2$ is —C(=NOR$^4$)R$^5$, wherein at least one of R$^4$ and R$^5$ is butyl. In another embodiment, R$^2$ is —C(=NOR$^4$)R$^5$, wherein each of R$^4$ and R$^5$ is butyl. In another embodiment, R$^2$ is —C(=NOR$^4$)R$^5$, wherein R$^4$ is methyl and R$^5$ is ethyl. In another embodiment, R$^2$ is —C(=NOR$^4$)R$^5$, wherein R$^4$ is ethyl and R$^5$ is methyl. In another embodiment, R$^2$ is —C(=NOR$^4$)R$^5$, wherein R$^4$ is methyl and R$^5$ is propyl. In another embodiment, R$^2$ is —C(=NOR$^4$)R$^5$, wherein R$^4$ is propyl and R$^5$ is methyl. In another embodiment, R$^2$ is —C(=NOR$^4$)R$^5$, wherein R$^4$ is methyl and R$^5$ is butyl. In another embodiment, R$^2$ is —C(=NOR$^4$)R$^5$, wherein R$^4$ is butyl and R$^5$ is methyl. In another embodiment, R$^2$ is —C(=NOR$^4$)R$^5$, wherein R$^4$ is ethyl and R$^5$ is propyl. In another embodiment, R$^2$ is —C(=NOR$^4$)R$^5$, wherein R$^4$ is propyl and R$^5$ is ethyl. In another embodiment, R$^2$ is —C(=NOR$^4$)R$^5$, wherein R$^4$ is propyl and R$^5$ is butyl. In another embodiment, R$^2$ is —C(=NOR$^4$)R$^5$, wherein R$^4$ is butyl and R$^5$ is propyl. In another embodiment, R$^2$ is —C(=NOR$^4$)R$^5$, wherein at least one of R$^4$ and R$^5$ is phenyl. In another embodiment, R$^2$ is —C(=NOR$^4$)R$^5$, wherein R$^4$ is phenyl and R$^5$ is methyl. In another embodiment, R$^2$ is —C(=NOR$^4$)R$^5$, wherein R$^4$ is phenyl and R$^5$ is ethyl. In another embodiment, R$^2$ is —C(=NOR$^4$)R$^5$, wherein at least one of R$^4$ and R$^5$ is phenyl substituted with a substituent selected from among the substituents disclosed above in connection with the compounds of formula (III). In another embodiment, R$^2$ is —C(=NOR$^4$)R$^5$ wherein R$^4$ is phenyl substituted with a substituent selected from among the substituents disclosed above in connection with the compounds of formula (III) and R$^5$ is methyl. In another embodiment, R$^2$ is —C(=NOR$^4$)R$^5$, wherein R$^4$ is phenyl substituted with a substituent selected from among the substituents disclosed above in connection with the compounds of formula (III) and R$^5$ is ethyl. In another embodiment, R$^2$ is —C(=NOR$^4$)R$^5$, wherein at least one of R$^4$ and R$^5$ is benzyl. In another embodiment, R$^2$ is —C(=NOR$^4$)R$^5$, wherein R$^4$ is benzyl and R$^5$ methyl. In another embodiment, R$^2$ is —C(=NOR$^4$)R$^5$, wherein R$^4$ is benzyl and R$^5$ ethyl.

In another embodiment, R$^2$ is unsubstituted phenyl. In another embodiment, R$^2$ is phenyl substituted with 1, 2 or 3 substituent(s) independently selected from halo, (C$_1$-C$_6$)alkyl, (C$_1$-C$_6$)alkoxy, (C$_1$-C$_6$)alkylsulfonyl, (C$_1$-C$_6$)alkylsulfinyl, —C(=O)NR$^4$R$^5$ and —S(O)$_2$—NR$^6$R$^7$.

In another embodiment, R$^2$ is (C$_1$-C$_6$)alkyl, —C(=NOR$^4$)R$^5$, or phenyl, wherein said alkyl and phenyl are unsubstituted or substituted with a substituent selected from among the substituents disclosed above in connection with compounds of formula (III). In another embodiment, $R^2$ is $(C_1-C_6)$alkyl or $—C(=NOR^4)R^5$. In another embodiment, $R^2$ is methyl, ethyl, ethylpropanoate, $—(C=NOCH_3)CH_3$, $—(C=NOphenyl)CH_3$, $—(C=NO-4-bromophenyl)CH_3$, $—(C=NObenzyl)CH_3$, $—(C=NO-(2-methylpropyl))CH_3$, $—(C=NOethyl)CH_3$, $—(C=NOtert-butyl)CH_3$, phenyl, 3-methylphenyl, 3-chlorophenyl, 4-chlorophenyl, 3-fluorophenyl, 4-fluorophenyl, 4-(methylsulfonyl)phenyl, 3-methoxyphenyl, 4-methoxyphenyl, 4-(methylsulfinyl)phenyl, 3-bromo-4-methoxyphenyl, 3,4-dimethoxyphenyl, 4-methoxy-3-methylphenyl, N,N-dimethylphenyl-1-sulfonamide, N,N-dimethylphenyl-1-carboxamide, or 5-phenyl-1,2,4-oxadiazol-3-yl. In another embodiment, $R^2$ is methyl, $—(C=NOCH_3)CH_3$, or phenyl. In another embodiment, $R^2$ is methyl or $—(C=NOCH_3)CH_3$.

In one embodiment, $R^3$ is $(C_1-C_6)$alkyl, phenyl, $—NR^6R^7$, or $—OR^8$. In another embodiment, $R^3$ is $(C_1-C_6)$alkyl, phenyl, $—NR^6R^7$, or $(C_1-C_6)$alkoxy. In another embodiment, $R^3$ is $(C_1-C_6)$alkyl, $—NR^6R^7$, or $(C_1-C_6)$alkoxy.

In another embodiment, $R^3$ is $(C_1-C_6)$alkyl. In another embodiment, $R^3$ is methyl, ethyl, iso-propyl, or tert-butyl. In another embodiment, $R^3$ is methyl, ethyl, or iso-propyl. In another embodiment, $R^3$ is methyl, ethyl, or tert-butyl. In another embodiment, $R^3$ is methyl, iso-propyl, or tert-butyl. In another embodiment, $R^3$ is ethyl, iso-propyl, or tert-butyl. In another embodiment, $R^3$ is methyl or ethyl. In another embodiment, $R^3$ is methyl or iso-propyl. In another embodiment, $R^3$ is methyl or tert-butyl. In another embodiment, $R^3$ is ethyl or iso-propyl. In another embodiment, $R^3$ is ethyl or tert-butyl. In another embodiment, $R^3$ is iso-propyl or tert-butyl. In another embodiment, $R^3$ is methyl. In another embodiment, $R^3$ is ethyl. In another embodiment, $R^3$ is iso-propyl. In another embodiment, $R^3$ is tert-butyl.

In another embodiment, $R^3$ is $—NR^6R^7$, wherein at least one of $R^6$ and $R^7$ is hydrogen. In another embodiment, $R^3$ is $—NR^6R^7$, wherein each of $R^6$ and $R^7$ is hydrogen. In another embodiment, $R^3$ is $—NR^6R^7$, wherein at least one of $R^6$ and $R^7$ is $(C_1-C_6)$alkyl. In another embodiment, $R^3$ is $—NR^6R^7$, wherein each of $R^6$ and $R^7$ is $(C_1-C_6)$alkyl. In another embodiment, $R^3$ is $—NR^6R^7$, wherein at least one of $R^6$ and $R^7$ is methyl. In another embodiment, $R^3$ is $—NR^6R^7$, wherein each of $R^6$ and $R^7$ is methyl. In another embodiment, $R^3$ is $—NR^6R^7$, wherein at least one of $R^6$ and $R^7$ is ethyl. In another embodiment, $R^3$ is $—NR^6R^7$, wherein each of $R^6$ and $R^7$ is ethyl. In another embodiment, $R^3$ is $—NR^6R^7$, wherein at least one of $R^6$ and $R^7$ is propyl. In another embodiment, $R^3$ is $—NR^6R^7$, wherein each of $R^6$ and $R^7$ is propyl. In another embodiment, $R^3$ is $—NR^6R^7$, wherein at least one of $R^6$ and $R^7$ is butyl. In another embodiment, $R^3$ is $—NR^6R^7$, wherein each of $R^6$ and $R^7$ is butyl.

In another embodiment, $R^3$ is $(C_1-C_6)$alkoxy. In another embodiment, $R^3$ is methoxy, ethoxy, propoxy or butoxy. In another embodiment, $R^3$ is methoxy or ethoxy. In another embodiment, $R^3$ is methoxy or propoxy. In another embodiment, $R^3$ is methoxy or butoxy. In another embodiment, $R^3$ is ethoxy or propoxy. In another embodiment, $R^3$ is ethoxy or butoxy. In another embodiment, $R^3$ is propoxy or butoxy. In another embodiment, $R^3$ is methoxy. In another embodiment, $R^3$ is ethoxy. In another embodiment, $R^3$ is propoxy. In another embodiment, $R^3$ is butoxy.

In another embodiment, $R^3$ is unsubstituted or substituted phenyl, wherein the substituents are selected from among the substituents disclosed above in connection with compounds of formula (III). In another embodiment, $R^3$ is unsubstituted phenyl. In another embodiment, $R^3$ is phenyl substituted with a substituent selected from among the substituents disclosed above in connection with compounds of formula (III). In another embodiment, $R^3$ is methyl, tert-butyl, dimethylamino, methoxy, butoxy or phenyl. In another embodiment, $R^3$ is methyl, dimethylamino, methoxy or butoxy.

In one embodiment, Y is $C(=O)$. In another embodiment, Y is $C(=S)$. In another embodiment, Y is $C(=NR^9)$. In another embodiment, Y is $C(=NR^9)$, wherein $R^9$ is H. In another embodiment, Y is $C(=NR^9)$, wherein $R^9$ is $(C_1-C_6)$alkyl. In another embodiment, Y is $C(=NR^9)$, wherein $R^9$ is methyl. In another embodiment, Y is $CR^{10}R^{11}$. In another embodiment, Y is $CR^{10}R^{11}$, wherein at least one of $R^{10}$ and $R^{11}$ is H. In another embodiment, Y is $CR^{10}R^{11}$, wherein each of $R^{10}$ and $R^{11}$ is H. In another embodiment, Y is $CR^{10}R^{11}$, wherein at least one of $R^{10}$ and $R^{11}$ is $(C_1-C_6)$alkyl. In another embodiment, Y is $CR^{10}R^{11}$, wherein each of $R^{10}$ and $R^{11}$ is $(C_1-C_6)$alkyl. In another embodiment, Y is $CR^{10}R^{11}$, wherein at least one of $R^{10}$ and $R^{11}$ is methyl. In another embodiment, Y is $CR^{10}R^{11}$, wherein each of $R^{10}$ and $R^{11}$ is methyl.

In one embodiment, Z is O. In another embodiment, Z is S.

In one embodiment, Y is $C(=O)$ and Z is O. In another embodiment, Y is $C(=O)$ and Z is S. In another embodiment, Y is $C(=S)$ and Z is O. In another embodiment, Y is $C(=S)$ and Z is S. In another embodiment, Y is $C(=NR^9)$ and Z is O. In another embodiment, Y is $C(=NR^9)$ and Z is S. In another embodiment, Y is $C(=NR^9)$, wherein $R^9$ is H and Z is O. In another embodiment, Y is $C(=NR^9)$, wherein $R^9$ is H and Z is S. In another embodiment, Y is $C(=NR^9)$, wherein $R^9$ is $(C_1-C_6)$alkyl and Z is O. In another embodiment, Y is $C(=NR^9)$, wherein $R^9$ is $(C_1-C_6)$alkyl and Z is S. In another embodiment, Y is $C(=NR^9)$, wherein $R^9$ is methyl and Z is O. In another embodiment, Y is $C(=NR^9)$, wherein $R^9$ is methyl and Z is S.

In another embodiment, $R^2$ is methyl and $R^3$ is methyl. In another embodiment, $R^2$ is methyl and $R^3$ is ethyl. In another embodiment, $R^2$ is methyl and $R^3$ is iso-propyl. In another embodiment, $R^2$ is methyl and $R^3$ is tert-butyl. In another embodiment, $R^2$ is ethyl and $R^3$ is methyl. In another embodiment, $R^2$ is ethyl and $R^3$ is ethyl. In another embodiment, $R^2$ is ethyl and $R^3$ is iso-propyl. In another embodiment, $R^2$ is ethyl and $R^3$ is tert-butyl. In another embodiment, $R^2$ is iso-propyl and $R^3$ is methyl. In another embodiment, $R^2$ is iso-propyl and $R^3$ is ethyl. In another embodiment, $R^2$ is iso-propyl and $R^3$ is iso-propyl. In another embodiment, $R^2$ is iso-propyl and $R^3$ is tert-butyl. In another embodiment, $R^2$ is tert-butyl and $R^3$ is methyl. In another embodiment, $R^2$ is tert-butyl and $R^3$ is ethyl. In another embodiment, $R^2$ is tert-butyl and $R^3$ is iso-propyl. In another embodiment, $R^2$ is tert-butyl and $R^3$ is tert-butyl.

In another embodiment, $R^2$ is $—C(=NOR^4)R^5$ and $R^3$ is methyl. In another embodiment, $R^2$ is $—C(=NOR^4)R^5$, wherein at least one of $R^4$ and $R^5$ is methyl, and $R^3$ is methyl. In another embodiment, $R^2$ is $—C(=NOR^4)R^5$, wherein each of $R^4$ and $R^5$ is methyl, and $R^3$ is methyl. In another embodiment, $R^2$ is $—C(=NOR^4)R^5$, wherein one of $R^4$ and $R^5$ is methyl and the other is ethyl, and $R^3$ is methyl. In another embodiment, $R^2$ is $—C(=NOR^4)R^5$ and $R^3$ is ethyl. In another embodiment, $R^2$ is $—C(=NOR^4)R^5$, wherein at least one of $R^4$ and $R^5$ is methyl, and $R^3$ is ethyl. In another embodiment, $R^2$ is $—C(=NOR^4)R^5$, wherein each of $R^4$ and $R^5$ is methyl, and $R^3$ is ethyl. In another embodiment, $R^2$ is $—C(=NOR^4)R^5$, wherein one of $R^4$ and $R^5$ is methyl and the other is ethyl, and $R^3$ is ethyl. In another embodiment, $R^2$ is —C(=NOR$^4$)R$^5$ and R$^3$ is iso-propyl. In another embodiment, R$^2$ is —C(=NOR$^4$)R$^5$, wherein at least one of R$^4$ and R$^5$ is methyl, and R$^3$ is iso-propyl. In another embodiment, R$^2$ is —C(=NOR$^4$)R$^5$, wherein each of R$^4$ and R$^5$ is methyl, and R$^3$ is iso-propyl. In another embodiment, R$^2$ is —C(=NOR$^4$)R$^5$, wherein one of R$^4$ and R$^5$ is methyl and the other is ethyl, and R$^3$ is iso-propyl. In another embodiment, R$^2$ is —C(=NOR$^4$)R$^5$, and R$^3$ is tert-butyl. In another embodiment, R$^2$ is —C(=NOR$^4$)R$^5$, wherein at least one of R$^4$ and R$^5$ is methyl, and R$^3$ is tert-butyl. In another embodiment, R$^2$ is —C(=NOR$^4$)R$^5$, wherein each of R$^4$ and R$^5$ is methyl, and R$^3$ is tert-butyl. In another embodiment, R$^2$ is —C(=NOR$^4$)R$^5$, wherein one of R$^4$ and R$^5$ is methyl and the other is ethyl, and R$^3$ is tert-butyl.

In another embodiment, R$^2$ is methyl and R$^3$ is methoxy. In another embodiment, R$^2$ is methyl and R$^3$ is ethoxy. In another embodiment, R$^2$ is methyl and R$^3$ is iso-propoxy. In another embodiment, R$^2$ is methyl and R$^3$ is tert-butoxy. In another embodiment, R$^2$ is ethyl and R$^3$ is methoxy. In another embodiment, R$^2$ is ethyl and R$^3$ is ethoxy. In another embodiment, R$^2$ is ethyl and R$^3$ is iso-propoxy. In another embodiment, R$^2$ is ethyl and R$^3$ is tert-butoxy. In another embodiment, R$^2$ is iso-propyl and R$^3$ is methoxy. In another embodiment, R$^2$ is iso-propyl and R$^3$ is ethoxy. In another embodiment, R$^2$ is iso-propyl and R$^3$ is iso-propoxy. In another embodiment, R$^3$ is iso-propyl and R$^3$ is tert-butoxy. In another embodiment, R$^2$ is tert-butyl and R$^3$ is methoxy. In another embodiment, R$^2$ is tert-butyl and R$^3$ is ethoxy. In another embodiment, R$^2$ is tert-butyl and R$^3$ is iso-propoxy. In another embodiment, R$^2$ is tert-butyl and R$^3$ is tert-butoxy.

In another embodiment, R$^2$ is —C(=NOR$^4$)R$^5$ and R$^3$ is methoxy. In another embodiment, R$^2$ is —C(=NOR$^4$)R$^5$, wherein at least one of R$^4$ and R$^5$ is methyl, and R$^3$ is methoxy. In another embodiment, R$^2$ is —C(=NOR$^4$)R$^5$, wherein each of R$^4$ and R$^5$ is methyl, and R$^3$ is methoxy. In another embodiment, R$^2$ is —C(=NOR$^4$)R$^5$, wherein one of R$^4$ and R$^5$ is methyl and the other is ethyl, and R$^3$ is methoxy. In another embodiment, R$^2$ is —C(=NOR$^4$)R$^5$ and R$^3$ is ethoxy. In another embodiment, R$^2$ is —C(=NOR$^4$)R$^5$, wherein at least one of R$^4$ and R$^5$ is methyl, and R$^3$ is ethoxy. In another embodiment, R$^2$ is —C(=NOR$^4$)R$^5$, wherein each of R$^4$ and R$^5$ is methyl, and R$^3$ is ethoxy. In another embodiment, R$^2$ is —C(=NOR$^4$)R$^5$, wherein one of R$^4$ and R$^5$ is methyl and the other is ethyl, and R$^3$ is ethoxy. In another embodiment, R$^2$ is —C(=NOR$^4$)R$^5$ and R$^3$ is iso-propoxy. In another embodiment, R$^2$ is —C(=NOR$^4$)R$^5$, wherein at least one of R$^4$ and R$^5$ is methyl, and R$^3$ is iso-propoxy. In another embodiment, R$^2$ is —C(=NOR$^4$)R$^5$, wherein each of R$^4$ and R$^5$ is methyl, and R$^3$ is iso-propoxy. In another embodiment, R$^2$ is —C(=NOR$^4$)R$^5$, wherein one of R$^4$ and R$^5$ is methyl and the other is ethyl, and R$^3$ is iso-propoxy. In another embodiment, R$^2$ is —C(=NOR$^4$)R$^5$ and R$^3$ is tert-butoxy. In another embodiment, R$^2$ is —C(=NOR$^4$)R$^5$, wherein at least one of R$^4$ and R$^5$ is methyl, and R$^3$ is tert-butoxy. In another embodiment, R$^2$ is —C(=NOR$^4$)R$^5$, wherein each of R$^4$ and R$^5$ is methyl, and R$^3$ is tert-butoxy. In another embodiment, R$^2$ is —C(=NOR$^4$)R$^5$, wherein one of R$^4$ and R$^5$ is methyl and the other is ethyl, and R$^3$ is tert-butoxy.

In another embodiment, R$^2$ is methyl and R$^3$ is dimethylamino. In another embodiment, R$^2$ is ethyl and R$^3$ is dimethylamino. In another embodiment, R$^2$ is iso-propyl and R$^3$ is dimethylamino. In another embodiment, R$^2$ is tert-butyl and R$^3$ is dimethylamino. In another embodiment, R$^2$ is —C(=NOR$^4$)R$^5$ and R$^3$ is dimethylamino. In another embodiment, R$^2$ is —C(=NOR$^4$)R$^5$, wherein at least one of R$^4$ and R$^5$ is methyl, and R$^3$ is dimethylamino. In another embodiment, R$^2$ is —C(=NOR$^4$)R$^5$, wherein each of R$^4$ and R$^5$ is methyl, and R$^3$ is dimethylamino. In another embodiment, R$^2$ is —C(=NOR$^4$)R$^5$, wherein one of R$^4$ and R$^5$ is methyl and the other is ethyl, and R$^3$ is dimethylamino.

Another aspect of the disclosure provides a compound of formula (III'):

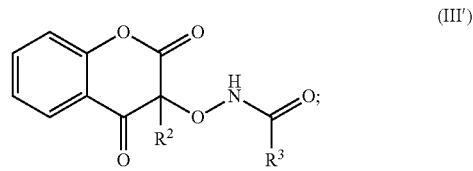

(III')

or a pharmaceutically acceptable salt thereof, wherein:
R$^2$, R$^3$, R$^4$, R$^5$, R$^6$, R$^7$, and R$^9$ are as defined above in connection with the compounds of formula (III).

In another embodiment, R$^2$ is methyl and R$^3$ is methyl. In another embodiment, R$^2$ is methyl and R$^3$ is ethyl. In another embodiment, R$^2$ is methyl and R$^3$ is iso-propyl. In another embodiment, R$^2$ is methyl and R$^3$ is tert-butyl. In another embodiment, R$^2$ is ethyl and R$^3$ is methyl. In another embodiment, R$^2$ is ethyl and R$^3$ is ethyl. In another embodiment, R$^2$ is ethyl and R$^3$ is iso-propyl. In another embodiment, R$^2$ is ethyl and R$^3$ is tert-butyl. In another embodiment, R$^2$ is iso-propyl and R$^3$ is methyl. In another embodiment, R$^2$ is iso-propyl and R$^3$ is ethyl. In another embodiment, R$^2$ is iso-propyl and R$^3$ is iso-propyl. In another embodiment, R$^2$ is iso-propyl and R$^3$ is tert-butyl. In another embodiment, R$^2$ is tert-butyl and R$^3$ is methyl. In another embodiment, R$^2$ is tert-butyl and R$^3$ is ethyl. In another embodiment, R$^2$ is tert-butyl and R$^3$ is iso-propyl. In another embodiment, R$^2$ is tert-butyl and R$^3$ is tert-butyl.

In another embodiment, R$^2$ is —C(=NOR$^4$)R$^5$ and R$^3$ is methyl. In another embodiment, R$^2$ is —C(=NOR$^4$)R$^5$, wherein at least one of R$^4$ and R$^5$ is methyl, and R$^3$ is methyl. In another embodiment, R$^2$ is —C(=NOR$^4$)R$^5$, wherein each of R$^4$ and R$^5$ is methyl, and R$^3$ is methyl. In another embodiment, R$^2$ is —C(=NOR$^4$)R$^5$, wherein one of R$^4$ and R$^5$ is methyl and the other is ethyl, and R$^3$ is methyl. In another embodiment, R$^2$ is —C(=NOR$^4$)R$^5$ and R$^3$ is ethyl. In another embodiment, R$^2$ is —C(=NOR$^4$)R$^5$, wherein at least one of R$^4$ and R$^5$ is methyl, and R$^3$ is ethyl. In another embodiment, R$^2$ is —C(=NOR$^4$)R$^5$, wherein each of R$^4$ and R$^5$ is methyl, and R$^3$ is ethyl. In another embodiment, R$^2$ is —C(=NOR$^4$)R$^5$, wherein one of R$^4$ and R$^5$ is methyl and the other is ethyl, and R$^3$ is ethyl. In another embodiment, R$^2$ is —C(=NOR$^4$)R$^5$ and R$^3$ is iso-propyl. In another embodiment, R$^2$ is —C(=NOR$^4$)R$^5$, wherein at least one of R$^4$ and R$^5$ is methyl, and R$^3$ is iso-propyl. In another embodiment, R$^2$ is —C(=NOR$^4$)R$^5$, wherein each of R$^4$ and R$^5$ is methyl, and R$^3$ is iso-propyl. In another embodiment, R$^2$ is —C(=NOR$^4$)R$^5$, wherein one of R$^4$ and R$^5$ is methyl and the other is ethyl, and R$^3$ is iso-propyl. In another embodiment, R$^2$ is —C(=NOR$^4$)R$^5$ and R$^3$ is tert-butyl. In another embodiment, R$^2$ is —C(=NOR$^4$)R$^5$, wherein at least one of R$^4$ and R$^5$ is methyl, and R$^3$ is tert-butyl. In another embodiment, R$^2$ is —C(=NOR$^4$)R$^5$, wherein each of R$^4$ and R$^5$ is methyl, and R$^3$ is tert-butyl. In another embodiment, R$^2$ is —C(=NOR$^4$)R$^5$, wherein one of R$^4$ and R$^5$ is methyl and the other is ethyl, and R$^3$ is tert-butyl.

In another embodiment, $R^2$ is methyl and $R^3$ is methoxy. In another embodiment, $R^2$ is methyl and $R^3$ is ethoxy. In another embodiment, $R^2$ is methyl and $R^3$ is iso-propoxy. In another embodiment, $R^2$ is methyl and $R^3$ is tert-butoxy. In another embodiment, $R^2$ is ethyl and $R^3$ is methoxy. In another embodiment, $R^2$ is ethyl and $R^3$ is ethoxy. In another embodiment, $R^2$ is ethyl and $R^3$ is iso-propoxy. In another embodiment, $R^2$ is ethyl and $R^3$ is tert-butoxy. In another embodiment, $R^2$ is iso-propyl and $R^3$ is methoxy. In another embodiment, $R^2$ is iso-propyl and $R^3$ is ethoxy. In another embodiment, $R^2$ is iso-propyl and $R^3$ is iso-propoxy. In another embodiment, $R^2$ is iso-propyl and $R^3$ is tert-butoxy. In another embodiment, $R^2$ is tert-butyl and $R^3$ is methoxy. In another embodiment, $R^2$ is tert-butyl and $R^3$ is ethoxy. In another embodiment, $R^2$ is tert-butyl and $R^3$ is iso-propoxy. In another embodiment, $R^2$ is tert-butyl and $R^3$ is tert-butoxy.

In another embodiment, $R^2$ is —C(=NOR$^4$)R$^5$ and $R^3$ is methoxy. In another embodiment, $R^2$ is —C(=NOR$^4$)R$^5$, wherein at least one of $R^4$ and $R^5$ is methyl, and $R^3$ is methoxy. In another embodiment, $R^2$ is —C(=NOR$^4$)R$^5$, wherein each of $R^4$ and $R^5$ is methyl, and $R^3$ is methoxy. In another embodiment, $R^2$ is —C(=NOR$^4$)R$^5$, wherein one of $R^4$ and $R^5$ is methyl and the other is ethyl, and $R^3$ is methoxy. In another embodiment, $R^2$ is —C(=NOR$^4$)R$^5$ and $R^3$ is ethoxy. In another embodiment, $R^2$ is —C(=NOR$^4$)R$^5$, wherein at least one of $R^4$ and $R^5$ is methyl, and $R^3$ is ethoxy. In another embodiment, $R^2$ is —C(=NOR$^4$)R$^5$, wherein each of $R^4$ and $R^5$ is methyl, and $R^3$ is ethoxy. In another embodiment, $R^2$ is —C(=NOR$^4$)R$^5$, wherein one of $R^4$ and $R^5$ is methyl and the other is ethyl, and $R^3$ is ethoxy. In another embodiment, $R^2$ is —C(=NOR$^4$)R$^5$ and $R^3$ is iso-propoxy. In another embodiment, $R^2$ is —C(=NOR$^4$)R$^5$, wherein at least one of $R^4$ and $R^5$ is methyl, and $R^3$ is iso-propoxy. In another embodiment, $R^2$ is —C(=NOR$^4$)R$^5$, wherein each of $R^4$ and $R^5$ is methyl, and $R^3$ is iso-propoxy. In another embodiment, $R^2$ is —C(=NOR$^4$)R$^5$, wherein one of $R^4$ and $R^5$ is methyl and the other is ethyl, and $R^3$ is iso-propoxy. In another embodiment, $R^2$ is —C(=NOR$^4$)R$^5$ and $R^3$ is tert-butoxy. In another embodiment, $R^2$ is —C(=NOR$^4$)R$^5$, wherein at least one of $R^4$ and $R^5$ is methyl, and $R^3$ is tert-butoxy. In another embodiment, $R^2$ is —C(=NOR$^4$)R$^5$, wherein each of $R^4$ and $R^5$ is methyl, and $R^3$ is tert-butoxy. In another embodiment, $R^2$ is —C(=NOR$^4$)R$^5$, wherein one of $R^4$ and $R^5$ is methyl and the other is ethyl, and $R^3$ is tert-butoxy.

In another embodiment, $R^2$ is methyl and $R^3$ is dimethylamino. In another embodiment, $R^2$ is ethyl and $R^3$ is dimethylamino. In another embodiment, $R^2$ is iso-propyl and $R^3$ is dimethylamino. In another embodiment, $R^2$ is tert-butyl and $R^3$ is dimethylamino. In another embodiment, $R^2$ is —C(=NOR$^4$)R$^5$ and $R^3$ is dimethylamino. In another embodiment, $R^2$ is —C(=NOR$^4$)R$^5$, wherein at least one of $R^4$ and $R^5$ is methyl, and $R^3$ is dimethylamino. In another embodiment, $R^2$ is —C(=NOR$^4$)R$^5$, wherein each of $R^4$ and $R^5$ is methyl, and $R^3$ is dimethylamino. In another embodiment, $R^2$ is —C(=NOR$^4$)R$^5$, wherein one of $R^4$ and $R^5$ is methyl and the other is ethyl, and $R^3$ is dimethylamino.

Table 1 provides representative compounds of the disclosure.

TABLE 1

| No. | Name | Structure |
|---|---|---|
| 1 | N-((4-(1-(methoxyimino)ethyl)-3-methyl-5-oxo-1-phenyl-4,5-dihydro-1H-pyrazol-4-yl)oxy)acetamide | 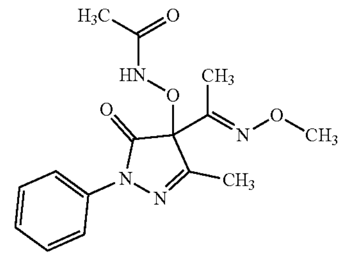 [SMILES: CO/N=C(\C)C1(ONC(C)=O)C(=O)N(c2ccccc2)N=C1C] |
| 2 | N-((3,4-dimethyl-5-oxo-1-phenyl-4,5-dihydro-1H-pyrazol-4-yl)oxy)acetamide | 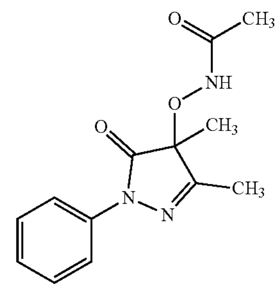 [SMILES: CC(=O)NOC1(C)C(=O)N(c2ccccc2)N=C1C] |
| 3 | methyl (4-(1-(methoxyimino)ethyl)-3-methyl-5-oxo-1-phenyl-4,5-dihydro-1H-pyrazol-4-yl)oxycarbamate | 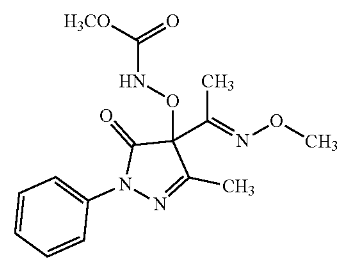 [SMILES: CO/N=C(\C)C1(ONC(=O)OC)C(=O)N(c2ccccc2)N=C1C] |
| 4 | methyl (4-(1-(methoxyimino)ethyl)-1,3-dimethyl-5-oxo-4,5-dihydro-1H-pyrazol-4-yl)oxycarbamate | 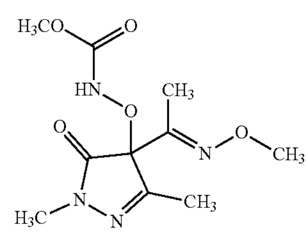 |
| 5 | tert-butyl (4-(1-(methoxyimino)ethyl)-3-methyl-5-oxo-1-phenyl-4,5-dihydro-1H-pyrazol-4-yl)oxycarbamate | 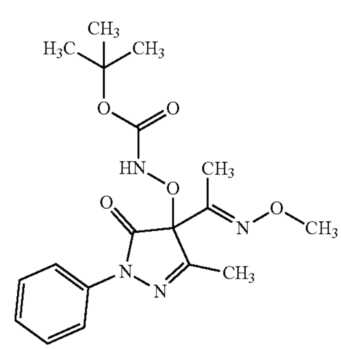 [SMILES: CO/N=C(\C)C1(ONC(=O)OC(C)(C)C)C(=O)N(c2ccccc2)N=C1C] |

TABLE 1-continued

| No. | Name | Structure |
|---|---|---|
| 6 | tert-butyl (4-(1-(methoxyimino)ethyl)-1,3-dimethyl-5-oxo-4,5-dihydro-1H-pyrazol-4-yl)oxycarbamate | 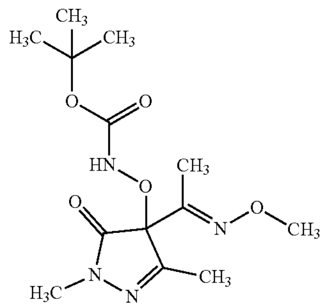 [SMILES: CO/N=C(\C)C1(ONC(=O)OC(C)(C)C)C(=O)N(C)N=C1C] |
| 7 | 3-((4-(1-(methoxyimino)ethyl)-3-methyl-5-oxo-1-phenyl-4,5-dihydro-1H-pyrazol-4-yl)oxy)-1,1-dimethylurea | 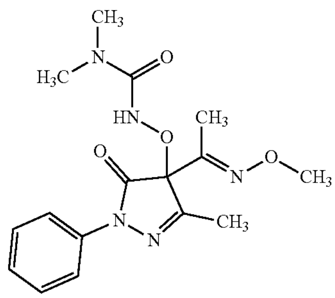 [SMILES: CO/N=C(\C)C1(ONC(=O)N(C)C)C(=O)N(c2ccccc2)N=C1C] |
| 8 | 3-((4-(1-(methoxyimino)ethyl)-1,3-dimethyl-5-oxo-4,5-dihydro-1H-pyrazol-4-yl)oxy)-1,1-dimethylurea | 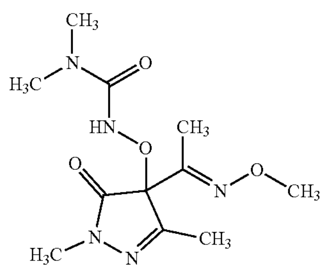 |
| 9 | 3-((3,4-dimethyl-5-oxo-1-phenyl-4,5-dihydro-1H-pyrazol-4-yl)oxy)-1,1-dimethylurea | 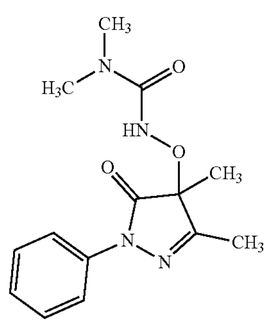 [SMILES: CC1=NN(c2ccccc2)C(=O)C1(C)ONC(=O)N(C)C] |
| 10 | 1,1-dimethyl-3-(((1,3,4-trimethyl-5-oxo-4,5-dihydro-1H-pyrazol-4-yl)oxy)urea | 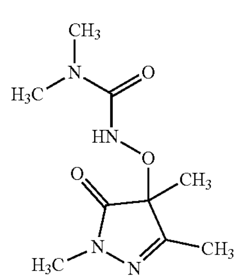 |
| 11 | N-((1,4-dimethyl-3-(4-(methylsulfonyl)phenyl)-5-oxo-4,5-dihydro-1H-pyrazol-4-yl)oxy)acetamide | |
| 12 | methyl (1,4-dimethyl-3-(4-(methylsulfonyl)phenyl)-5-oxo-4,5-dihydro-1H-pyrazol-4-yl)oxycarbamate | |
| 13 | tert-butyl (1,4-dimethyl-3-(4-(methylsulfonyl)phenyl)-5-oxo-4,5-dihydro-1H-pyrazol-4-yl)oxycarbamate | |
| 14 | 3-((1,4-dimethyl-3-(4-(methylsulfonyl)phenyl)-5-oxo-4,5-dihydro-1H pyrazol-4-yl)oxy)-1,1-dimethylurea | |

TABLE 1-continued

| No. | Name | Structure |
|---|---|---|
| 15 | N-((5-methyl-2,4,6-trioxohexahydropyrimidin-5-yl)oxy)acetamide | 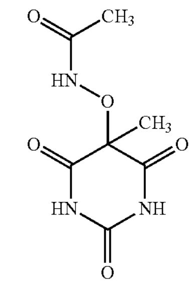 |
| 16 | N-((1,3,5-trimethyl-2,4,6-trioxohexahydropyrimidin-5-yl)oxy)acetamide | 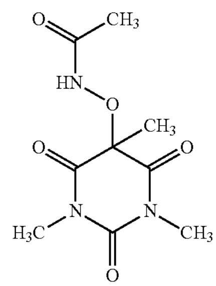 [SMILES: CC(=O)NOC1(C)C(=O)N(C)C(=O)N(C)C1=O] |
| 17 | N-((5-(1-(methoxyimino)ethyl)-2,4,6-trioxohexahydropyrimidin-5-yl)oxy)acetamide | 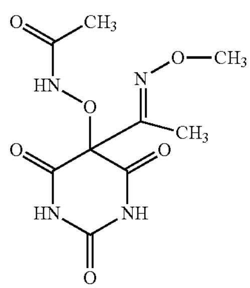 [SMILES: CO/N=C(\C)C1(ONC(C)=O)C(=O)NC(=O)NC1=O] |
| 18 | N-((5-(1-(methoxyimino)ethyl)-1,3-dimethyl-2,4,6-trioxohexahydropyrimidin-5-yl)oxy)acetamide | 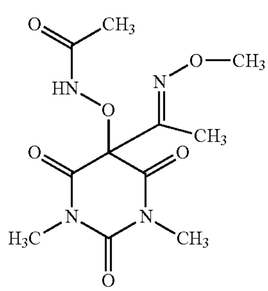 [SMILES: CO/N=C(\C)C1(ONC(C)=O)C(=O)N(C)C(=O)N(C)C1=O] |
| 19 | methyl (5-methyl-2,4,6-trioxohexahydropyrimidin-5-yl)oxycarbamate | 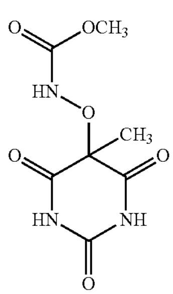 [SMILES: COC(=O)NOC1(C)C(=O)NC(=O)NC1=O] |
| 20 | methyl (1,3,5-trimethyl-2,4,6-trioxohexahydropyrimidin-5-yl)oxycarbamate | 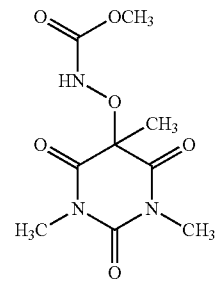 [SMILES: COC(=O)NOC1(C)C(=O)N(C)C(=O)N(C)C1=O] |
| 21 | methyl (5-(1-(methoxyimino)ethyl)-2,4,6-trioxohexahydropyrimidin-5-yl)oxycarbamate | 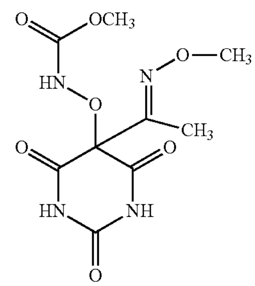 [SMILES: CO/N=C(\C)C1(ONC(=O)OC)C(=O)NC(=O)NC1=O] |
| 22 | methyl (5-(1-(methoxyimino)ethyl)-1,3-dimethyl-2,4,6-trioxohexahydropyrimidin-5-yl)oxycarbamate | 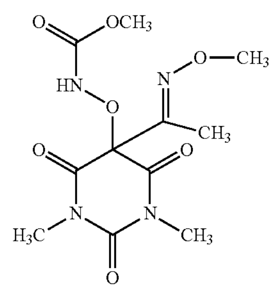 [SMILES: CO/N=C(\C)C1(ONC(=O)OC)C(=O)N(C)C(=O)N(C)C1=O] |
| 23 | tert-butyl (5-methyl-2,4,6-trioxohexahydropyrimidin-5-yl)oxycarbamate | 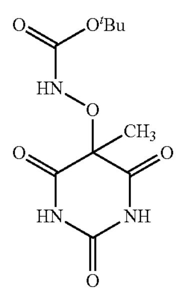 |
| 24 | tert-butyl (1,3,5-trimethyl-2,4,6-trioxohexahydropyrimidin-5-yl)oxycarbamate | 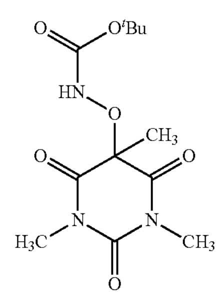 [SMILES: CN1C(=O)N(C)C(=O)C(C)(ONC(=O)OC(C)(C)C)C1=O] |

TABLE 1-continued

| No. | Name | Structure |
|---|---|---|
| 25 | tert-butyl (5-(1-(methoxyimino)ethyl)-2,4,6-trioxohexahydropyrimidin-5-yl)oxycarbamate | 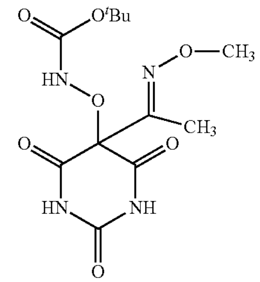 [SMILES: CO/N=C(\C)C1(ONC(=O)OC(C)(C)C)C(=O)NC(=O)NC1=O] |
| 26 | tert-butyl (5-(1-(methoxyimino)ethyl)-1,3-dimethyl-2,4,6-trioxohexahydropyrimidin-5-yl)oxycarbamate | 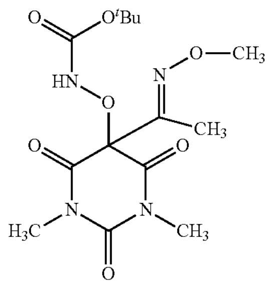 [SMILES: CO/N=C(\C)C1(ONC(=O)OC(C)(C)C)C(=O)N(C)C(=O)N(C)C1=O] |
| 27 | 1,1-dimethyl-3-((5-methyl-2,4,6-trioxohexahydropyrimidin-5-yl)oxy)urea | 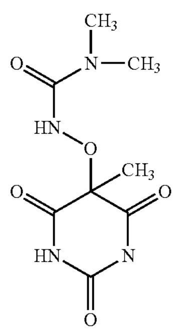 [SMILES: CN(C)C(=O)NOC1(C)C(=O)NC(=O)NC1=O] |
| 28 | 1,1-dimethyl-3-((1,3,5-trimethyl-2,4,6-trioxohexahydropyrimidin-5-yl)oxy)urea | 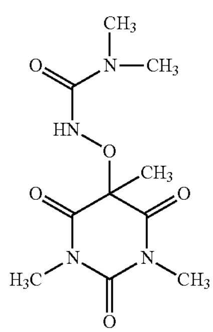 [SMILES: CN(C)C(=O)NOC1(C)C(=O)N(C)C(=O)N(C)C1=O] |
| 29 | 3-((5-(1-(methoxyimino)ethyl)-2,4,6-trioxohexahydropyrimidin-5-yl)oxy)-1,1-dimethylurea | 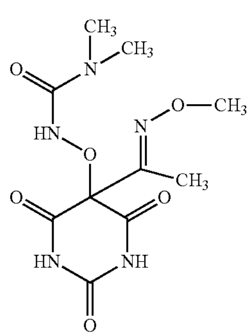 [SMILES: CO/N=C(\C)C1(ONC(=O)N(C)C)C(=O)NC(=O)NC1=O] |
| 30 | 3-((5-(1-(methoxyimino)ethyl)-1,3-dimethyl-2,4,6-trioxohexahydropyrimidin-5-yl)oxy)-1,1-dimethylurea | 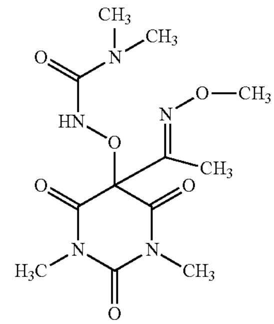 [SMILES: CO/N=C(\C)C1(ONC(=O)N(C)C)C(=O)N(C)C(=O)N(C)C1=O] |
| 31 | N-((3-methyl-2,4-dioxochroman-3-yl)oxy)acetamide | 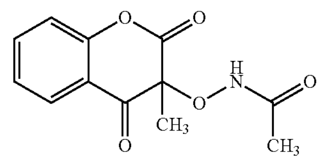 [SMILES: CC(=O)NOC1(C)C(=O)Oc2ccccc2C1=O] |
| 32 | N-((3-(1-(methoxyimino)ethyl)-2,4-dioxochroman-3-yl)oxy)acetamide | 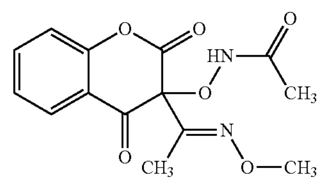 [SMILES: CO/N=C(\C)C1(ONC(C)=O)C(=O)Oc2ccccc2C1=O] |
| 33 | methyl (3-methyl-2,4-dioxochroman-3-yl)oxycarbamate | 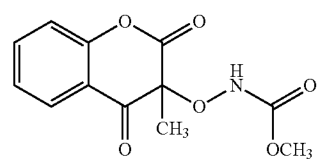 [SMILES: COC(=O)NOC1(C)C(=O)Oc2ccccc2C1=O] |
| 34 | methyl (3-(1-(methoxyimino)ethyl)-2,4-dioxochroman-3-yl)oxycarbamate | 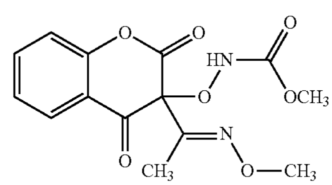 [SMILES: CO/N=C(\C)C1(ONC(=O)OC)C(=O)Oc2ccccc2C1=O] |
| 35 | tert-butyl (3-methyl-2,4-dioxochroman-3-yl)oxycarbamate | 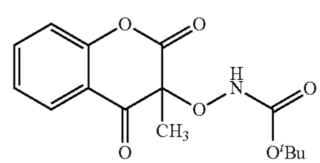 [SMILES: CC(C)(C)OC(=O)NOC1(C)C(=O)Oc2ccccc2C1=O] |
| 36 | tert-butyl (3-(1-(methoxyimino)ethyl)-2,4-dioxochroman-3-yl)oxycarbamate | 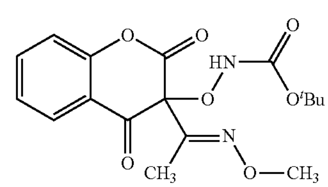 [SMILES: CO/N=C(\C)C1(ONC(=O)OC(C)(C)C)C(=O)Oc2ccccc2C1=O] |
| 37 | 1,1-dimethyl-3-((3-methyl-2,4-dioxochroman-3-yl)oxy)urea | 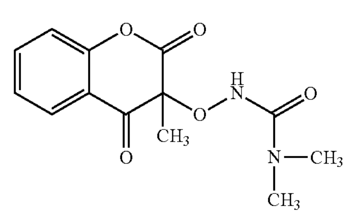 [SMILES: CN(C)C(=O)NOC1(C)C(=O)Oc2ccccc2C1=O] |

TABLE 1-continued

| No. | Name | Structure |
|---|---|---|
| 38 | 3-((3-(1-(methoxyimino)ethyl)-2,4-dioxochroman-3-yl)oxy)-1,1-dimethylurea | 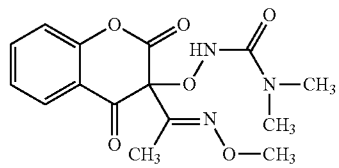 [SMILES: CO/N=C(\C)C1(ONC(=O)N(C)C)C(=O)Oc2ccccc2C1=O] |

Measuring Nitroxyl Donating Ability

Compounds are easily tested for nitroxyl donation by routine experiments. Although it is typically impractical to directly measure whether nitroxyl is donated, several analytical approaches are accepted as suitable for determining whether a compound donates nitroxyl. For example, a test compound can be placed in solution, for example in phosphate buffered saline ("PBS") or in a phosphate buffered solution at a pH of about 7.4, in a sealed container. After sufficient time for disassociation has elapsed, such as from several minutes to several hours, the headspace gas is withdrawn and analyzed to determine its composition, such as by gas chromatography and/or mass spectrometry. If the gas $N_2O$ is formed (which occurs by HNO dimerization), the test is positive for nitroxyl donation and the test compound is deemed to be a nitroxyl donor.

If desired, nitroxyl donation also can be detected by exposing the test compound to metmyoglobin ("$Mb^{3+}$"). See Bazylinski et al., *J. Amer. Chem. Soc.* 107(26):7982-7986 (1985). Nitroxyl reacts with $Mb^{3+}$ to form a $Mb^{2+}$—NO complex, which can be detected by changes in the ultraviolet/visible spectrum or by electron paramagnetic resonance ("EPR"). The $Mb^{2+}$—NO complex has an EPR signal centered around a g-value of about 2. Nitric oxide, on the other hand, reacts with $Mb^{3+}$ to form an $Mb^{3+}$—NO complex that has a negligible, if any, EPR signal. Accordingly, if a compound reacts with $Mb^{3+}$ to form a complex detectable by common methods, such as ultraviolet/visible or EPR, then the test is positive for nitroxyl donation.

The level of nitroxyl donating ability can be expressed as a percentage of a compound's theoretical stoichiometric maximum. A compound that donates a "significant level of nitroxyl" means, in various embodiments, a compound that donates about 40% or more, about 50% or more, about 60% or more, about 70% or more, about 80% or more, about 90% or more, or about 95% or more of its theoretical maximum amount of nitroxyl. In particular embodiments, a compound donates from about 70% to about 90% of its theoretical maximum amount of nitroxyl. In particular embodiments, a compound donates from about 85% to about 95% of its theoretical maximum amount of nitroxyl. In particular embodiments, a compound donates from about 90% to about 95% of its theoretical maximum amount of nitroxyl. Compounds that donate less than about 40%, or less than about 50%, of their theoretical maximum amount of nitroxyl are still nitroxyl donors and can be used in the methods disclosed. A compound that donates less than about 50% of its theoretical amount of nitroxyl can be used in the methods disclosed, but may require higher dosing levels as compared to a compound that donates a higher level of nitroxyl.

Testing for nitroxyl donation can be performed at a physiologically relevant pH. In particular embodiments, a compound of the disclosure is capable of donating nitroxyl at physiological pH (i.e., apH of about 7.4) and physiological temperature (i.e., a temperature of about 37° C.) (together, "physiological conditions"). In particular embodiments, a compound of the disclosure can donate about 40% or more of its theoretical maximum (i.e., 100%) amount of nitroxyl under physiological conditions. In particular embodiments, a compound of the disclosure can donate about 50% or more of its theoretical maximum amount of nitroxyl under physiological conditions. In particular embodiments, a compound of the disclosure can donate about 60% or more of its theoretical maximum amount of nitroxyl under physiological conditions. In particular embodiments, a compound of the disclosure can donate about 70% or more of its theoretical maximum amount of nitroxyl under physiological conditions. In particular embodiments, a compound of the disclosure can donate about 80% or more of its theoretical maximum amount of nitroxyl under physiological conditions. In particular embodiments, a compound of the disclosure can donate about 90% or more of its theoretical maximum amount of nitroxyl under physiological conditions.

It will be understood that a compound of the disclosure might also donate a limited amount of nitric oxide, so long as the amount of nitroxyl donation exceeds the amount of nitric oxide donation. In certain embodiments, a compound of the disclosure can donate about 25 mole % or less of nitric oxide under physiological conditions. In particular embodiments, a compound of the disclosure can donate about 20 mole % or less of nitric oxide under physiological conditions. In particular embodiments, a compound of the disclosure can donate about 15 mole % or less of nitric oxide under physiological conditions. In particular embodiments, a compound of the disclosure can donate about 10 mole % or less of nitric oxide under physiological conditions. In particular embodiments, a compound of the disclosure can donates about 5 mole % or less of nitric oxide under physiological conditions. In particular embodiments, a compound of the disclosure can donate about 2 mole % or less of nitric oxide under physiological conditions. In particular embodiments, a compound of the disclosure can donate an insignificant amount (e.g., about 1 mole % or less) of nitric oxide under physiological conditions.

Pharmaceutical Compositions and Administration

The disclosure also encompasses pharmaceutical compositions comprising at least one compound of formula (I), (II), (III), (I'), (II'), (III'), or a compound from Table 1, and at least one pharmaceutically acceptable excipient. Examples of pharmaceutically acceptable excipients include those described above, such as carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and any combination thereof. The selection and use of pharmaceutically acceptable excipients is taught, e.g., in Troy, Ed., *Remington: The Science and Practice of Pharmacy*, 21$^{st}$ Ed. (Lippincott Williams & Wilkins, Baltimore, Md., 2005).

In one embodiment, the at least one pharmaceutically acceptable excipient is selected from lactose, microcrystalline cellulose, croscarmellose, or any mixture thereof. In another embodiment, the at least one pharmaceutically acceptable excipient is selected from lactose, microcrystalline cellulose, croscarmellose sodium, or any mixture thereof. Lactose, the naturally-occurring disaccharide of galactose and glucose, being available in a range of varieties, e.g., granulated, sieved, milled, spray dried, and anhydrous, is a well-accepted excipient for medical and pharmaceutical uses. Reilly, "Pharmaceutical Necessities," pp. 1015-1050 in *Remington: The Science and Practice of*

*Pharmacy* (Gennaro, ed., 20th ed., Lippincott, Williams & Wilkins, Baltimore, Md., 2000). Microcrystalline cellulose is disclosed to be a most resourceful excipient because of the profusion of grades available for different needs and its physical properties that support a variety of functional requirements, e.g., as a bulking agent, disintegrant, binder, lubricant, glidant, and/or stability enhancer. Baboota et al., "Microcrystalline cellulose as a versatile excipient in drug research," *J. Young Pharmacists* 1:6-12 (2009). Croscarmellose is an internally cross-linked carboxymethylcellulose; croscarmellose sodium is the sodium salt of an internally cross-linked, at least partially O-(carboxymethylated) cellulose. Either form of this excipient has reduced water solubility, attributed to the cross-linking, thus providing, inter alia, enhanced dissolution characteristics. Boylan et al., pp. 2623-2624 in *Encyclopedia of Pharmaceut. Technol.* (1st ed., Marcel Dekker, New York, 1988).

The pharmaceutical compositions can be formulated for administration in solid or liquid form, including those adapted for the following: (1) oral administration, for example, as drenches (for example, aqueous or non-aqueous solutions or suspensions), tablets (for example, those targeted for buccal, sublingual and systemic absorption), caplets, boluses, powders, granules, pastes for application to the tongue, hard gelatin capsules, soft gelatin capsules, mouth sprays, troches, lozenges, pellets, syrups, suspensions, elixirs, liquids, emulsions and microemulsions; or (2) parenteral administration by, for example, subcutaneous, intramuscular, intravenous or epidural injection as, for example, a sterile solution or suspension. The pharmaceutical compositions can be for immediate, sustained, or controlled release.

In one particular embodiment, the pharmaceutical composition is formulated for intravenous administration. In another embodiment, the pharmaceutical composition is formulated for intravenous administration by continuous infusion.

In another embodiment, the pharmaceutical composition is formulated for oral administration. In another embodiment, the pharmaceutical composition is formulated for oral administration as a liquid dosage form. In another embodiment, the pharmaceutical composition is formulated for oral administration in solid dosage form. In particular embodiments where the pharmaceutical composition is formulated as an oral liquid or solid dosage form, polyethylene glycol, such as polyethylene glycol 300 ("PEG300"), polyethylene glycol 400 ("PEG400"), and mixtures thereof, can serve as an excipient.

The pharmaceutical composition can be prepared as any appropriate unit dosage form, such as capsule, sachet, tablet, powder, granule, solution, suspension in an aqueous liquid, suspension in a non-aqueous liquid, oil-in-water liquid emulsion, water-in-oil liquid emulsion, liposomes or bolus. In one embodiment, the pharmaceutical composition is formulated as a tablet. In another embodiment, the pharmaceutical composition is formulated as a capsule.

Tablets can be made by compression or molding, optionally with one or more accessory ingredients. Compressed tablets can be prepared by compressing in a suitable machine the therapeutic agent or agents in a free-flowing form such as a powder or granules, optionally mixed with a binder, lubricant, inert diluent, preservative, surface-active or dispersing agent. Molded tablets can be made by molding in a suitable machine a mixture of the powdered compound moistened with an inert liquid diluent. The tablets can be optionally coated or scored and can be formulated so as to provide slow or controlled release of the active ingredient therein. Methods of formulating such slow or controlled release compositions of pharmaceutically active ingredients, such as the therapeutic agents herein and other compounds known in the art, are known in the art and disclosed in issued U.S. patents, some of which include, but are not limited to, U.S. Pat. Nos. 4,369,174, 4,842,866, and the references cited therein. Coatings can be used for delivery of compounds to the intestine (see, e.g., U.S. Pat. Nos. 6,638,534, 5,217,720, 6,569,457, and the references cited therein). An artisan will recognize that in addition to tablets, other dosage forms can be formulated to provide slow or controlled release of the active ingredient. Such dosage forms include, but are not limited to, capsules, granulations and gel-caps.

Pharmaceutical compositions suitable for topical administration include, without limitation, lozenges comprising the ingredients in a flavored basis, such as sucrose, acacia and tragacanth; and pastilles comprising the active ingredient in a flavored basis or in an inert basis, such as gelatin and glycerin.

Various embodiments of pharmaceutical compositions suitable for parenteral administration include, without limitation, either aqueous sterile injection solutions or non-aqueous sterile injection solutions, each containing, for example, anti-oxidants, buffers, bacteriostats and solutes that render the formulation isotonic with the blood of the intended recipient; and aqueous sterile suspensions and non-aqueous sterile suspensions, each containing, for example, suspending agents and thickening agents. The formulations can be presented in unit-dose or multi-dose containers, for example, sealed ampules or vials, and can be stored in a freeze dried (lyophilized) condition requiring only the addition of a sterile liquid carrier, such as water, immediately prior to use.

Pharmaceutical compositions administered parenterally can be administered in an acidic, neutral or basic solution. In one embodiment, pharmaceutical compositions are formulated in an acidic solution having a pH of from about 4 to about 5, for instance, a pH of about 4, about 4.5, about 4.8, or about 5, including values there between. While a pH of about 4 has generally been considered optimal for formulating nitroxyl donating compositions to achieve adequate stability of the compound, it has been discovered that formulating under such acidic conditions can potentially cause or exacerbate venous irritation following parenteral administration. The amount of irritation can be attenuated by formulating the pharmaceutical compositions in less acidic or even neutral solutions. Accordingly, in particular embodiments, a pharmaceutical composition formulated for parenteral use at a pH of from about 5 to about 6.2 (e.g., pH of about 5, about 5.5, about 5.8, about 6, or about 6.2, including values there between).

Method of Using the Compounds or Pharmaceutical Compositions

In one aspect, the disclosure provides a method of increasing in vivo nitroxyl levels, comprising administering to a patient in need thereof an effective amount of a compound or a pharmaceutical composition as disclosed herein. In various embodiments, the patient has, is suspected of having, or is at risk of having or developing a condition that is responsive to nitroxyl therapy.

In particular embodiments, the disclosure provides a method of treating, preventing or delaying the onset and/or development of a condition, comprising administering to a patient (including a patient identified as in need of such treatment, prevention or delay) an effective amount of a compound or a pharmaceutical composition as disclosed herein. Identifying a patient in need thereof can be in the judgment of a physician, clinical staff, emergency response personnel or other health care professional and can be subjective (e.g., opinion) or objective (e.g., measurable by a test or diagnostic method).

Particular conditions embraced by the methods disclosed herein include, without limitation, cardiovascular diseases, ischemia/reperfusion injury, and pulmonary hypertension.

Cardiovascular Diseases

In one embodiment, the disclosure provides a method of treating a cardiovascular disease, comprising administering an effective amount of a compound or a pharmaceutical composition as disclosed herein to a patient in need thereof.

Examples of cardiovascular diseases and symptoms that can usefully be treated with the compounds and compositions disclosed herein include cardiovascular diseases that are responsive to nitroxyl therapy, coronary obstructions, coronary artery disease ("CAD"), angina, heart attack, myocardial infarction, high blood pressure, ischemic cardiomyopathy and infarction, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, diastolic heart failure, systolic heart failure, congestive heart failure, acute congestive heart failure, acute decompensated heart failure, and cardiac hypertrophy.

Heart Failure

The compounds and pharmaceutical compositions of the disclosure can be used to treat patients suffering from heart failure. The heart failure can be of any type or form, including any of the heart failures disclosed herein. Non-limiting examples of heart failure include early stage heart failure, Class I, II, III and IV heart failure, acute heart failure, congestive heart failure ("CHF") and acute CHF. In one embodiment, the compounds and pharmaceutical compositions of the disclosure can be used to treat acute decompensated heart failure.

In embodiments where the compounds and pharmaceutical compositions of the disclosure are used to treat patients suffering from, heart failure, another active agent that treats heart failure can also be administered. In one such embodiment, the compound or pharmaceutical composition of the disclosure can be administered in conjunction with a positive inotrope such as a beta-agonist. Examples of beta-agonists include, without limitation, dopamine, dobutamine, isoproterenol, analogs of such compounds and derivatives of such compounds. In another embodiment, the compound or pharmaceutical composition of the disclosure can be administered in conjunction with a beta-adrenergic receptor antagonist (also referred to herein as beta-antagonist or beta-blocker). Examples of beta-antagonists include, without limitation, propranolol, metoprolol, bisoprolol, bucindolol, and carvedilol.

Compounds of the disclosure can be administered as pharmaceutical formulations to patients in need of modulating in vivo nitroxyl levels. For instance, a pharmaceutical formulation comprising a compound of the disclosure can be administered to a patient intravenously.

Ischemia/Reperfusion Injury

In another embodiment, the disclosed subject matter provides a method of treating, preventing or delaying the onset and/or development of ischemia/reperfusion injury, comprising administering an effective amount of a compound or pharmaceutical composition as disclosed herein to a subject in need thereof.

In a particular embodiment, the method is for preventing ischemia/reperfusion injury. In a particular embodiment, a compound or pharmaceutical composition of the disclosure is administered prior to the onset of ischemia. In a particular embodiment, a pharmaceutical composition of the disclosure is administered prior to procedures in which myocardial ischemia can occur, for example an angioplasty or surgery, such as a coronary artery bypass graft surgery. In a particular embodiment, a pharmaceutical composition of the disclosure is administered after ischemia but before reperfusion. In a particular embodiment, a pharmaceutical composition of the disclosure is administered after ischemia and reperfusion.

In another embodiment, a pharmaceutical composition of the disclosure can be administered to a patient who is at risk for an ischemic event. In a particular embodiment, a pharmaceutical composition of the disclosure is administered to a patient at risk for a future ischemic event, but who has no present evidence of ischemia. The determination of whether a patient is at risk for an ischemic event can be performed by any method known in the art, such as by examining the patient or the patient's medical history. In a particular embodiment, the patient has had a prior ischemic event. Thus, the patient can be at risk of a first or subsequent ischemic event. Examples of patients at risk for an ischemic event include patients with known hypercholesterolemia, EKG changes associated with ischemia (e.g., peaked or inverted T-waves or ST segment elevations or depression in an appropriate clinical context), abnormal EKG not associated with active ischemia, elevated CKMB, clinical evidence of ischemia (e.g., crushing sub-sternal chest pain or arm pain, shortness of breath and/or diaphoresis), prior history of myocardial infarction ("MI"), elevated serum cholesterol, sedentary lifestyle, angiographic evidence of partial coronary artery obstruction, echocardiographic evidence of myocardial damage, or any other evidence of a risk for a future ischemic event. Examples of ischemic events include, without limitation, MI and neurovascular ischemia, such as a cerebrovascular accident ("CVA").

In another embodiment, the subject of treatment is an organ that is to be transplanted. In a particular embodiment, a pharmaceutical composition of the disclosure can be administered prior to reperfusion of the organ in a transplant recipient. In a particular embodiment, a pharmaceutical composition of the disclosure can be administered prior to removal of the organ from the donor, for example through the perfusion cannulas used in the organ removal process. If the organ donor is a live donor, for example a kidney donor, the compounds or pharmaceutical compositions of the disclosure can be administered to the organ donor. In a particular embodiment, the compounds or pharmaceutical compositions of the disclosure are administered by storing the organ in a solution comprising the compound or pharmaceutical composition. For example, a compound or pharmaceutical composition of the disclosure can be included in the organ preservation solution, such as the University of Wisconsin "UW" solution, which is a solution comprising hydroxyethyl starch substantially free of ethylene glycol, ethylene chlorohydrin and acetone (see U.S. Pat. No. 4,798, 824). In a particular embodiment, a pharmaceutical composition of the disclosure that is administered is such that ischemia/reperfusion injury to the tissues of the organ is reduced upon reperfusion in the recipient of transplanted organ. In a particular embodiment, the method reduces tissue necrosis (the size of infarct) in at-risk tissues.

Ischemia/reperfusion injury can damage tissues other than those of the myocardium and the disclosed subject matter embraces methods of treating or preventing such damage. In various embodiments, the ischemia/reperfusion injury is non-myocardial. In particular embodiments, the method reduces injury from ischemia/reperfusion in the tissue of the brain, liver, gut, kidney, bowel, or any part of the body other than the myocardium. In another embodiment, the patient is at risk for such injury. Selecting a person at risk for non-myocardial ischemia could include a determination of the indicators used to assess risk for myocardial ischemia. However, other factors can indicate a risk for ischemia/reperfusion in other tissues. For example, surgery patients often experience surgery related ischemia. Thus, patients scheduled for surgery could be considered at risk for an ischemic event. The following risk factors for stroke (or a subset of these risk factors) could demonstrate a patient's risk for ischemia of brain tissue: hypertension, cigarette smoking, carotid artery stenosis, physical inactivity, diabetes mellitus, hyperlipidemia, transient ischemic attack, atrial fibrillation, CAD, CHF, past MI, left ventricular dysfunction with mural thrombus, and mitral stenosis. Ingall, *Postgrad. Med.* 107(6):34-50 (2000). Further, complications of untreated infectious diarrhea in the elderly can include myocardial, renal, cerebrovascular and intestinal ischemia. Slotwiner-Nie et al., *Gastroenterol. Clin. N. Amer.* 30(3): 625-635 (2001). Alternatively, patients could be selected based on risk factors for ischemic bowel, kidney and/or liver disease. For example, treatment would be initiated in elderly patients at risk of hypotensive episodes (such as surgical blood loss). Thus, patients presenting with such an indication would be considered at risk for an ischemic event. In another embodiment, the patient has any one or more of the conditions listed herein, such as diabetes mellitus and hypertension. Other conditions that can result in ischemia, such as cerebral arteriovenous malformation, could demonstrate a patient's risk for an ischemic event.

Pulmonary Hypertension

In another embodiment, a compound or pharmaceutical composition of the disclosure can be used to prevent or delay the onset and/or development of pulmonary hypertension. In one such embodiment, a compound or pharmaceutical composition of the disclosure can be used to prevent or delay the onset and/or development of pulmonary arterial hypertension ("PAH").

In another embodiment, the disclosed subject matter provides a method of reducing mean pulmonary arterial pressure ("MPAP"), comprising administering an effective amount of a compound or a pharmaceutical composition disclosed herein to a patient in need thereof. In another embodiment, the MPAP is reduced by up to about 50%. In another embodiment, the MPAP is reduced by up to about 25%. In another embodiment, the MPAP is reduced by up to about 20%. In another embodiment, the MPAP is reduced by up to about 15%. In another embodiment, the MPAP is reduced by up to 10%. In another embodiment, the MPAP is reduced by up to about 5%. In another embodiment, the MPAP is reduced to be from about 12 mmHg to about 16 mmHg. In another embodiment, the MPAP is reduced to be about 15 mmHg.

Administration Modes, Regimens and Dose Levels

The compounds and pharmaceutical compositions of the disclosure can be administered via parenteral (e.g., subcutaneous, intramuscular, intravenous or intradermal) administration. In certain embodiments, the compound or pharmaceutical composition is administered by intravenous infusion. In other embodiments, the compounds and pharmaceutical compositions of the disclosure can be administered by oral administration.

When a pharmaceutical composition comprising a compound of the disclosure is administered, dosages are expressed based on the amount of active pharmaceutical ingredient, i.e., the amount of compound(s) of the disclosure present in the pharmaceutical composition.

In a variety of embodiments, including various oral administration embodiments, the compounds or pharmaceutical compositions of the disclosure are administered according to a weight-based daily dosing regimen, either as a single daily dose ("QD") or in multiple divided doses administered, e.g., twice a day ("BID"), 3 times a day ("TID"), or four times a day ("QID").

In certain embodiments, the compound or pharmaceutical composition of the disclosure is administered in a dose of at least about 0.5 mg/kg/d, at least about 0.75 mg/kg/d, at least about 1.0 mg/kg/d, at least about 1.5 mg/kg/d, at least about 2 mg/kg/d, at least about 2.5 mg/kg/d, at least about 3 mg/kg/d, at least about 4 mg/kg/d, at least about 5 mg/kg/d, at least about 7.5 mg/kg/d, at least about 10 mg/kg/d, at least about 12.5 mg/kg/d, at least about 15 mg/kg/d, at least about 17.5 mg/kg/d, at least about 20 mg/kg/d, at least about 25 mg/kg/d, at least about 30 mg/kg/d, at least about 35 mg/kg/d, at least about 40 mg/kg/d, at least about 45 mg/kg/d, at least about 50 mg/kg/d, at least about 60 mg/kg/d, at least about 70 mg/kg/d, at least about 80 mg/kg/d, at least about 90 mg/kg/d, or at least about 100 mg/kg/d.

In certain embodiments, the compound or pharmaceutical composition of the disclosure is administered at a dose of no more than about 100 mg/kg/d, no more than about 100 mg/kg/d, no more than about 90 mg/kg/d, no more than about 80 mg/kg/d, no more than about 80 mg/kg/d, no more than about 75 mg/kg/d, no more than about 70 mg/kg/d, no more than about 60 mg/kg/d, no more than about 50 mg/kg/d, no more than about 45 mg/kg/d, no more than about 40 mg/kg/d, no more than about 35 mg/kg/d, or no more than about 30 mg/kg/d.

In a variety of embodiments, the dose is from about 0.001 mg/kg/d to about 10,000 mg/kg/d. In certain embodiments, the dose is from, about 0.01 mg/kg/d to about 1,000 mg/kg/d. In certain embodiments, the dose is from about 0.01 mg/kg/d to about 100 mg/kg/d. In certain embodiments, the dose is from about 0.01 mg/kg/d to about 10 mg/kg/d. In certain embodiments, the dose is from about 0.1 mg/kg/d to about 1 mg/kg/d. In certain embodiments, the dose is less than about 1 g/kg/d.

In certain embodiments, a compound or pharmaceutical composition of the disclosure is administered in a dose range in which the low end of the range is any amount from about 0.1 mg/kg/day to about 90 mg/kg/day and the high end of the range is any amount from about 1 mg/kg/day to about 100 mg/kg/day (e.g., from about 0.5 mg/kg/day to about 2 mg/kg/day in one series of embodiments and from about 5 mg/kg/day to about 20 mg/kg/day in another series of embodiments).

In particular embodiments, the compound or pharmaceutical composition of the disclosure is administered in a dose range of about 3 to about 30 mg/kg, administered QD, BID, or TID.

In certain embodiments, compounds or pharmaceutical compositions of the disclosure are administered according to a flat (i.e., non-weight-based) dosing regimen, either QD or in multiple divided doses administered, e.g., BID, TID, or QID.

In various embodiments, the compound or pharmaceutical composition of the disclosure is administered at a dose of at least about 0.01 grams/day (g/d), at least about 0.05 g/d, at least about 0.1 g/d, at least about 0.5 g/d, at least about 1 g/d, at least about 1.5 g/d, at least about 2.0 g/d, at least about 2.5 g/d, at least about 3.0 g/d, or at least about 3.5 g/d.

In various embodiments, the compound or pharmaceutical composition of the disclosure is administered at a dose of no more than about 5 g/d, no more than about 4.5 g/d, no more than about 4 g/d, no more than about 3.5 g/d, no more than about 3 g/d, no more than about 2.5 g/d, or no more than about 2 g/d.

In certain embodiments, the compound or pharmaceutical composition of the disclosure is administered in a dose of about 0.01 grams per day to about 4.0 grams per day. In certain embodiments, a compound or pharmaceutical composition of the disclosure can be administered at a dose in which the low end of the range is any amount from about 0.1 mg/day to about 400 mg/day and the high end of the range is any amount from about 1 mg/day to about 4000 mg/day. In certain embodiments, the compound or pharmaceutical composition is administered in a dose of about 5 mg/day to about 100 mg/day. In various embodiments, the compound or pharmaceutical composition is administered at a dose of from about 150 mg/day to about 500 mg/day.

The dosing interval for parenteral or oral administration can be adjusted according to the needs of the patient. For longer intervals between administrations, extended release or depot formulations can be used.

For intravenous administration, the dose can usefully be expressed per unit time, either as a fixed amount per unit time or as a weight-based amount per unit time.

In various embodiments, a compound or pharmaceutical composition of the disclosure is administered intravenously in an amount of at least about 0.1 µg/kg/min, at least about 0.2 µg/kg/min, at least about 0.3 µg/kg/min, at least about 0.4 µg/kg/min, at least about 0.5 µg/kg/min, at least about 1 µg/kg/min, at least about 2.5 µg/kg/min, at least about 5 µg/kg/min, at least about 7.5 µg/kg/min, at least about 10 µg/kg/min, at least about 11 µg/kg/min, at least about 12 µg/kg/min, at least about 13 µg/kg/min, at least about 14 µg/kg/min, at least about 15 µg/kg/min, at least about 16 µg/kg/min, at least about 17 µg/kg/min, at least about 18 µg/kg/min, at least about 19 µg/kg/min, at least about 20 µg/kg/min, at least about 21 µg/kg/min, at least about 22 µg/kg/min, at least about 23 µg/kg/min, at least about 24 µg/kg/min, at least about 25 µg/kg/min, at least about 26 µg/kg/min, at least about 27 µg/kg/min, at least about 28 µg/kg/min, at least about 29 µg/kg/min, at least about 30 µg/kg/min, at least about 31 µg/kg/min, at least about 32 µg/kg/min, at least about 33 µg/kg/min, at least about 34 µg/kg/min, at least about 35 µg/kg/min, at least about 36 µg/kg/min, at least about 37 µg/kg/min, at least about 38 µg/kg/min, at least about 39 µg/kg/min, or at least about 40 µg/kg/min.

In various embodiments, the compound or pharmaceutical composition of the present disclosure is administered intravenously in an amount of no more than about 100 µg/kg/min, no more than about 90 µg/kg/min, no more than about 80 µg/kg/min, no more than about 70 µg/kg/min, no more than about 60 µg/kg/min, no more than about 50 µg/kg/min, no more than about 49 µg/kg/min, no more than about 48 µg/kg/min, no more than about 47 µg/kg/min, no more than about 46 µg/kg/min, no more than about 45 µg/kg/min, no more than about 44 µg/kg/min, no more than about 43 µg/kg/min, no more than about 42 µg/kg/min, no more than about 41 µg/kg/min, no more than about 40 µg/kg/min, no more than about 39 µg/kg/min, no more than about 38 µg/kg/min, no more than about 37 µg/kg/min, no more than about 36 µg/kg/min, no more than about 35 µg/kg/min, no more than about 34 µg/kg/min, no more than about 33 µg/kg/min, no more than about 32 µg/kg/min, no more than about 31 µg/kg/min, or no more than about 30 µg/kg/min.

In some embodiments, the compound or pharmaceutical composition of the present disclosure is administered intravenously in an amount ranging from about 0.1 µg/kg/min to about 100 µg/kg/min, about 1 µg/kg/min to about 100 µg/kg/min, about 2.5 µg/kg/min to about 100 µg/kg/min, about 5 µg/kg/min to about 100 µg/kg/min, about 10 µg/kg/min to about 100 µg/kg/min, about 1.0 µg/kg/min to about 80 µg/kg/min, from about 10.0 µg/kg/min to about 70 µg/kg/min, from about 20 µg/kg/min to about 60 µg/kg/min, from about 15 µg/kg/min to about 50 µg/kg/min, from about 0.01 µg/kg/min to about 1.0 µg/kg/min, from about 0.01 µg/kg/min to about 10 µg/kg/min, from about 0.1 µg/kg/min to about 1.0 µg/kg/min, from about 0.1 µg/kg/min to about 10 µg/kg/min, from about 1.0 µg/kg/min to about 5 µg/kg/min, from about 70 µg/kg/min to about 100 µg/kg/min, or from about 80 µg/kg/min to about 90 µg/kg/min.

In particular embodiments, the compound or pharmaceutical composition of the present disclosure is administered intravenously in an amount ranging from about 10 µg/kg/min to about 50 µg/kg/min, about 20 µg/kg/min to about 40 µg/kg/min, about 25 µg/kg/min to about 35 µg/kg/min, or about 30 µg/kg/min to about 40 µg/kg/min. In particular embodiments, a compound or pharmaceutical composition of the present disclosure is administered intravenously in an amount of from, about 20 µg/kg/min to about 30 µg/kg/min.

A compound or pharmaceutical composition as disclosed herein can be administered prior to, at substantially the same time with, or after administration of an additional therapeutic agent. The administration regimen can include pretreatment and/or co-administration with the additional therapeutic agent. In such case, the compound or pharmaceutical composition and the additional therapeutic agent can be administered simultaneously, separately, or sequentially.

Examples of administration regimens include without limitation: administration of each compound, pharmaceutical composition or therapeutic agent in a sequential manner: and co-administration of each compound, pharmaceutical composition or therapeutic agent in a substantially simultaneous manner (e.g., as in a single unit dosage form) or in multiple, separate unit dosage forms for each compound, pharmaceutical composition or therapeutic agent.

It will be appreciated by those in the art that the "effective amount" or "dose" ("dose level") will depend on various factors such as the particular administration mode, administration regimen, compound, and pharmaceutical composition selected, as well as the particular condition and patient being treated. For example, the appropriate dose level can vary depending upon the activity, rate of excretion and potential for toxicity of the specific compound or pharmaceutical composition employed; the age, body weight, general health, gender and diet of the patient being treated; the frequency of administration; the other therapeutic agent(s) being co-administered; and the type and severity of the condition.

Kits Comprising the Compounds or Pharmaceutical Compositions

The disclosure provides kits comprising a compound or a pharmaceutical composition disclosed herein. In a particular embodiment, the kit comprises a compound or a pharmaceutical composition disclosed herein, each in dry form, and a pharmaceutically acceptable liquid diluent.

In particular embodiments, either a compound in dry form or a pharmaceutical composition in dry form contains about 2.0% or less water by weight, about 1.5% or less water by weight, about 1.0% or less water by weight, about 0.5% or less water by weight, about 0.3% or less water by weight, about 0.2% or less water by weight, about 0.1% or less water by weight, about 0.05% or less water by weight, about 0.03% or less water by weight, or about 0.01% or less water by weight.

Pharmaceutically acceptable liquid diluents are known in the art and include but are not limited to sterile water, saline solutions, aqueous dextrose, glycerol, glycerol solutions, and the like. Other examples of suitable liquid diluents are disclosed by Nairn, "Solutions, Emulsions, Suspensions and Extracts," pp. 721-752 in *Remington: The Science and Practice of Pharmacy*, 20th Ed. (Lippincott Williams & Wilkins, Baltimore, Md., 2000).

In one embodiment, the kit further comprises instructions for using the compound or pharmaceutical composition. The instructions can be in any appropriate form, such as written or electronic form. In another embodiment, the instructions can be written instructions. In another embodiment, the instructions are contained in an electronic storage medium (e.g., magnetic diskette or optical disk). In another embodiment, the instructions include information as to the compound or pharmaceutical composition and the manner of administering the compound or pharmaceutical composition to a patient. In another embodiment, the instructions relate to a method of use disclosed herein (e.g., treating, preventing and/or delaying onset and/or development of a condition selected from cardiovascular diseases, ischemia/reperfusion injury, pulmonary hypertension and other conditions responsive to nitroxyl therapy).

In another embodiment, the kit further comprises suitable packaging. Where the kit comprises more than one compound or pharmaceutical composition, the compounds or pharmaceutical compositions can be packaged in separate containers, or combined in one container when cross-reactivity and shelf life permit.

Should there be doubt over the agreement of a depicted chemical structure and a chemical name, the chemical name governs.

EXAMPLES

The following examples are presented for illustrative purposes and should not serve to limit the scope of the disclosed subject matter.

Synthesis of Compounds of the Disclosure

The compounds disclosed herein can be made according to the methods disclosed below or by procedures known in the art. Starting materials for the reactions can be commercially available or can be prepared by known procedures or obvious modifications thereof. For example, some of the starting materials are available from commercial suppliers such as Sigma-Aldrich (St. Louis, Mo.). Others can be prepared by procedures or obvious modifications thereof disclosed in standard reference texts such as *March's Advanced Organic Chemistry* (John Wiley and Sons) and *Larock's Comprehensive Organic Transformations* (VCH Publishers).

All starting materials were of reagent grade and used without further purification. N-hydroxy-N-(4-(acetyl-O-methoxyoxime)-3-methyl-5-oxo-1-phenyl-4,5-dihydro-1H-pyrazol-4-yl)-N-acetamide (NHPY-1), N-hydroxy-N-(4-(acetyl-O-methoxyoxime)-3-methyl-5-oxo-1-phenyl-4,5-dihydro-1H-pyrazol-4-yl)-N-methylcarbamate (NHPY-3), N-hydroxy-N-(4-(acetyl-O-methoxyoxime)-1,3-dimethyl-5-oxo-4,5-dihydro-1H-pyrazol-4-yl)-N-methylcarbamate (NHPY-4) (Nourian, S.; Zilber, Z. A.; Toscano, J. P. "Development of N-Substituted Hydroxamic Acids with Pyrazolone Leaving Groups as Nitrosocarbonyl Precursors", manuscript under review), 4-(acetyl-O-methoxyoxime)-3-methyl-1-phenyl-pyrazolone (PY-1), 3,4-dimethyl-1-phenyl-pyrazolone (PY-2), 4-(acetyl-O-methoxyoxime)-1,3-dimethylpyrazolone (PY-3) (Guthrie, D. A.; Ho, A.; Takahashi, C. G.; Collins, A.; Morris, M.; Toscano, J. P. *J. Org. Chem.* 2015, 80, 1338-1348), 4-(acetyl-O-methoxyoxime)-4-bromo-3-methyl-1-phenyl-pyrazolone, 4-bromo-3, 4-dimethyl-1-phenyl-pyrazolone, 4-(acetyl-O-methoxyoxime)-4-bromo-1,3-dimethyl-pyrazolone (Guthrie, D. A.; Kim, N. Y.; Siegler, M. A.; Moore, C. D.; Toscano, J. P. *J. Am. Chem. Soc.* 2012, 134, 1962-1965), C-methoxycarbohydroxamic acid, and tert-butylhydroxycarbamate (Defoin, A.; Fritz, H.; Schmidlin, C.; Streith, *J. Helv. Chim. Acta* 1987, 70, 554-569) were prepared according to literature procedures, Acetohydroxamic acid was purchased and used without further purification. NMR spectra were obtained on a 400 MHz FT-NMR spectrometer. All chemical shifts are reported in parts per million (ppm) relative to residual CHCl$_3$ (7.26 ppm for 1H, 77.23 ppm for $^{13}$C). High-resolution mass spectra were collected on a magnetic sector mass spectrometer working in fast atom bombardment (FAB) mode. Gas chromatography (GC) headspace analysis was performed on the instrument equipped with ECD detection and a molecular sieve packed column. Ultraviolet-Visible (UV-vis) absorption spectra were collected using a diode array spectrophotometer. For x-ray crystallography, all reflection intensities were measured at 110(2) K using a KM4/Xcalibur (detector: Sapphire 3) with enhance graphite-monochromated Mo Kα radiation (λ=0.71073 Å) under the program CrysAlisPro (Version 1.171.36.24 Agilent Technologies, 2012). The program CrysAlisPro (Version 1.171.36.24 Agilent Technologies, 2012) was used to refine the cell dimensions. Data reduction was done using the program CrysAlisPro (Version 1.171.36.24 Agilent Technologies, 2012). The structure was solved with the program SHELXS-2013 (Sheldrick, 2013) and was refined on F2 with SHELXL-2013 (Sheldrick, 2013). Analytical numeric absorption corrections based on a multifaceted crystal model were applied using CrysAlisPro (Version 1.171.36.24 Agilent Technologies, 2012). The temperature of the data collection was controlled using the system Cryojet (manufactured by Oxford Instruments). The H atoms were placed at calculated positions (unless otherwise specified) using the instructions AFIX 43 or AFIX 137 with isotropic displacement parameters having values 1.2 or 1.5 times Ueq of the attached C atoms.

The following "General Method" was employed in specific steps of the compound syntheses disclosed in the Examples, which Examples appear after the General Methods.

General Method

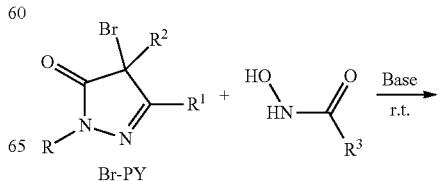

-continued

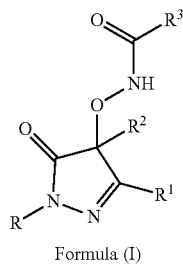

Formula (I)

Compounds of formula (I) have been synthesized by formation of the corresponding bromide (Br-PY) followed by reaction with hydroxamic acids. This General Method can be suitably modified to make additional compounds of the disclosure. Those skilled in the art will be able to recognize such modifications and to devise alternate synthetic methods based on the disclosed General Method.

Example 1: Compound 1-N-((4-(1-(methoxyimino)ethyl)-3-methyl-5-oxo-1-phenyl-4,5-dihydro-1H-pyrazol-4-yl)oxy)acetamide To a solution of hydroxamic acid (1 mmol) in dimethylformamide (3 ml) at room temperature was added sodium hydride, 60% (1.1 mmol), and the reaction stirred for one hour. This solution was added to a solution of 1 mmol of 4-(acetyl-O-methoxyoxime)-4-bromo-3-methyl-1-phenyl-pyrazolone in dimethylformamide (2 mL), and the reaction proceeded at room temperature for 3 hours. The reaction was diluted with ether (20 mL) and washed with ammonium chloride, water, and brine. The organic phase was collected, dried over magnesium sulphate ($MgSO_4$), filtered and concentrated in vacuo. Recrystallization from dichloromethane and hexane gave the product as a white solid with yields of 25%. $^1$H NMR ($CDCl_3$) δ: 8.19 (1H, s, OH), 7.92 (2H, m, arom), 7.43 (2H, m, arom), 7.24 (1H, m, atom), 3.90 (3H, s, Me), 2.37 (3H, s, Me), 2.09 (3H, s, Me), 1.98 (3H, s, Me). $^{13}$C NMR (400 MHz, $CDCl_3$) δ: 167.5, 158.1, 156.7, 150.8, 137.8, 129.1, 125.7, 119.1, 90.2, 62.5, 20.0, 16.4, 10.2. HR-MS (FAB): found m/z=319.14094 (MH$^+$); calc. for $C_{15}H_{19}O_4N_4$: 319.14063.

X-Ray Crystallographic Data: Fw=318.33, colorless block, 0.59×0.43, 0.38 mm$^3$, monoclinic, Pc (no. 9), a=14.9994(5), b=12.1027(4), c=9.3258(3) Å, β=106.778(3)°, V=1620.87(10) Å$^3$, Z=4, $D_x$=1.304 g cm$^{-3}$, μ=0.097 mm$^{-1}$, abs. corr. range: 0.961-0.973, 7785 Reflections were measured up to a resolution of (sin θ/λ)$_{max}$=0.65 Å$^{-1}$. 3537 Reflections were unique ($R_{int}$=0.0392), of which 3362 were observed [I>2σ(I)], 216 Parameters were refined using 2 restraints. R1/wR2 [I>2σ(I)]: 0.0315/0.0813. R1/wR2 [all refl.]: 0.0340/0.0829. S=1.056. Residual electron density found between −0.17 and 0.17 e Å$^{-3}$.

Example 2: Compound 2—N-((3,4-dimethyl-5-oxo-1-phenyl-4,5-dihydro-1H-pyrazol-4-yl)oxy)acetamide To a solution of hydroxamic acid (1 mmol) in dimethylformamide (3 ml) at room temperature was added sodium hydride, 60% (1.1 mmol), and the reaction stirred for one hour. This solution was added to a solution of 1 mmol of 4-bromo-3,4-dimethyl-1-phenyl-pyrazolone in dimethylformamide (2 ml), and the reaction proceeded at room temperature for 3 hours. The reaction was diluted with ether (20 mL) and washed with ammonium chloride, water, and brine. The organic phase was collected, dried over magnesium sulphate ($MgSO_4$), filtered and concentrated in vacuo. Following purification by flash chromatography (30% ethylacetate/hexane) on silica gel, gave the product as a white solid with a yield of 28%. $^1$H NMR ($CDCl_3$) δ: 9.07 (1H, s, OH), 7.89 (2H, m, arom), 7.41 (2H, m, arom), 7.24 (1H, m, arom), 2.34 (3H, s, Me), 1.92 (3H, s, Me), 1.56 (3H, s, Me). $^{13}$C NMR (100 MHz, $CDCl_3$) δ: 170.6, 161.3, 158.1, 137.5, 132.1, 129.1, 125.6, 118.4, 87.6, 20.4, 18.5, 13.2. HR-MS (FAB): found m/z=262.11949 (MH$^+$); calc. for $C_{13}H_{15}N_3O_3$: 262.11917.

Example 3: Compound 3—methyl(4-(1-(methoxyimino)ethyl)-3-methyl-5-oxo-1-phenyl-4,5-dihydro-1H-pyrazol-4-yl)oxycarbamate To a solution of hydroxamic acid (1 mmol) in acetonitrile (3 mL) at room temperature was added triethylamine (1 mmol), and the reaction stirred for one hour. This solution was added to a solution of 1 mmol of 4-(acetyl-O-methoxyoxime)-4-bromo-3-methyl-1-phenyl-pyrazolone in acetonitrile (2 mL), and the reaction proceeded at room, temperature for 3 hours. The reaction mixture was concentrated via rotary evaporation, redissolved in dichloromethane, and washed with water and brine. The organic phase was collected, dried over $MgSO_4$, filtered and concentrated in vacuo. The compound was purified by flash chromatography (20% ethylacetate/hexane) on silica gel to give the title compound as a white solid with a yield of 34%. $^1$H NMR ($CDCl_3$) δ: 7.91 (2H, m, arom), 7.50 (1H, s, OH), 7.41 (2H, m, arom), 7.20 (1H, m, arom), 3.90 (3H, s, Me), 3.77 (3H, s, Me), 2.38 (3H, s, Me), 2.08 (3H, s, Me). $^{13}$C NMR (100 MHz, $CDCl_3$) δ: 166.8, 158.8, 157.3, 151.3, 137.4, 129.2, 125.3, 118.7, 89.8, 62.8, 53.8, 14.9, 10.0. HR-MS (FAB): found m/z=335.13496 (MH$^+$); calc. for $C_{15}H_{19}N_4O_5$: 335.13554.

Example 4: Compound 4—methyl(4-(1-(methoxyimino)ethyl)-1,3-dimethyl-5-oxo-4,5-dihydro-1H-pyrazol-4-yl)oxycarbamate To a solution of hydroxamic acid (1 mmol) in acetonitrile (3 mL) at room temperature was added triethylamine (1 mmol), and the reaction stirred for one hour. This solution was added to a solution of 1 mmol of 4-(acetyl-O-methoxyoxime)-4-bromo-1,3-dimethyl-pyrazolone in acetonitrile (2 mL), and the reaction proceeded at room temperature for 3 hours. The reaction mixture was concentrated via rotary evaporation, redissolved in dichloromethane, and washed with water and brine. The organic phase was collected, dried over $MgSO_4$, filtered and concentrated in vacuo. The compound was purified by flash chromatography (20% ethylacetate/hexane) on silica gel to give the title compound as a white solid with a yield of 28%. $^1$H NMR ($CDCl_3$) δ: 7.52 (1H, s, OH), 3.89 (3H, s, Me), 3.79 (3H, s, Me), 3.28 (3H, s, Me), 2.27 (3H, s, Me), 2.03 (3H, s, Me). $^{13}$C NMR (100 MHz, $CDCl_3$) δ: 168.6, 158.3, 157.6, 151.1, 88.9, 62.5, 53.3, 31.4, 15.0, 10.3. HR-MS (FAB): found m/z=273.12013 (MH$^+$); calc. for $C_{10}H^{17}N_4O_5$: 273.11989.

Example 5: Compound 5—tert-butyl(4-(1-(methoxyimino)ethyl)-3-methyl-5-oxo-1-phenyl-4,5-dihydro-1H-pyrazol-4-yl)oxy carbamate To a solution of hydroxamic acid (1 mmol) in acetonitrile (3 mL) at room temperature was added triethylamine (1 mmol), and the reaction stirred for one hour. This solution was added to a solution of 1 mmol of 4-(acetyl-O-methoxyoxime)-4-bromo-3-methyl-1-phenyl-pyrazolone in acetonitrile (2 mL), and the reaction proceeded at room, temperature for 3 hours. The reaction mixture was concentrated via rotary evaporation, redissolved in dichloromethane, and washed with water and brine. The organic phase was collected, dried over MgSO$_4$, filtered and concentrated in vacuo. The compound was purified by flash chromatography (20% ethylacetate/hexane) on silica gel to give the title compound as a white solid with a yield 37%. $^1$H NMR (CDCl$_3$) δ: 7.93 (2H, m, arom), 7.43 (2H, m, arom), 7.31 (1H, s, OH), 7.22 (1H, m, arom), 3.91 (3H, s, Me), 2.36 (3H, s, Me), 2.06 (3H, s, Me), 1.46 (1H, s, C(Me)$_3$), $^{13}$C NMR (100 MHz, CDCl$_3$) δ: 167.3, 159.4, 156.1, 151.2, 137.8, 129.2, 125.3, 118.4, 89.8, 82.9, 62.4, 28.0, 15.1, 10.2. HR-MS (FAB): found m/z=377.18180 (MH$^+$); calc. for C$_{18}$H$_{25}$O$_5$N$_4$: 377.18250.

Example 6: Stability of Compounds of the Disclosure as Determined Via $^1$H NMR Protocol A $^1$H NMR spectroscopy protocol was used to examine the decomposition of the compounds of the disclosure and measure the relative product yields in aqueous solution (Guthrie, D. A.; Ho, A.; Takahashi, C. G.; Collins, A.; Morris, M.; Toscano, J. P. *J. Org. Chem.* 2015, 80, 1338-1348; and Guthrie, D. A.; Nourian, S.; Takahashi, C. G.; Toscano, J. P. *J. Org. Chem.* 2015, 80, 1349-1356). Table 2 shows the results of these experiments.

TABLE 2

| Compound | R | R$^2$ | R$^3$ | PY | NHPY | Carboxylic Acid |
|---|---|---|---|---|---|---|
| 1 | Ph | C(=NOMe)Me | Me | 74 | 26 | 73 |
| 2 | Ph | Me | Me | | | |
| 3 | Ph | C(=NOMe)Me | MeO | 28 | 72 | 27 |
| 4 | Me | C(=NOMe)Me | MeO | 14 | 86 | 14 |
| 5 | Ph | C(=NOMe)Me | tBuO | N.D.$^a$ | N.D.$^a$ | N.D.$^a$ |

$^a$Not Determined due to low solubility.

As shown in Table 2, corresponding pyrazolone (PY), NHBY and carboxylic acid were cleanly formed as the only observable organic products (Scheme 2). Because the corresponding NHPY compounds all have half-lives of days (Nourian, S.; Zilber, Z. A.; Toscano, J. P. "Development of A-Substituted Hydroxamic Acids with Pyrazolone Leaving Groups as Nitrosocarbonyl Precursors", manuscript under review), the relative yields of corresponding pyrazolones and carboxylic acids compared with that for the corresponding NHPYs reflect the competition between Path A and Path B for these compounds, and Path C does not contribute to the observed chemistry.

Scheme 2.

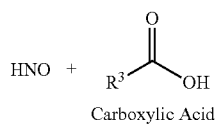

Carboxylic Acid

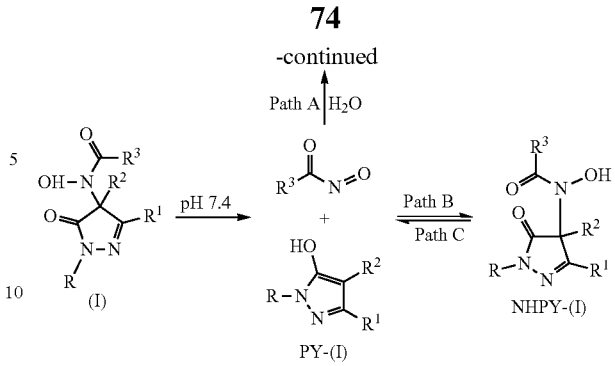

Example 7: Nitroxyl Production from Compounds of the Disclosure as Determined Via N$_2$O Quantification in the Headspace Protocol Nitrous oxide (N$_2$O) is produced via the dimerization and dehydration of HNO, and is the most common marker for nitroxyl production (Fukuto et al., *Chem. Res. Toxicol.* 18:790-801 (2005)). Nitroxyl, however, can also be partially quenched by oxygen to provide a product that does not produce N$_2$O (see Mincione et al., *J. Enzyme Inhibition* 13:267-284 (1998); and Scozzafava et al., *J. Med. Chem.* 43:3677-3687 (2000)). Using either nitrous oxide gas or Angeli's salt ("AS") as a standard, the relative amounts of N$_2$O released from compounds of the disclosure is examined via gas chromatography ("GC") headspace analysis.

A procedure for determining the relative amounts of N$_2$O released from compounds of the disclosure is as follows. GC is performed on an Agilent gas chromatograph equipped with a split injector (10:1 splitting), microelectron capture detector, and a HP-MOLSIV 30 m×0.32 mm×25 μm molecular sieve capillary column. Helium is used as the carrier (4 mL/min) gas and nitrogen is used as the make-up (20 mL/min) gas. The injector oven and the detector oven are kept at 200° C. and 325° C., respectively. All nitrous oxide analyses are performed with the column oven held at a constant temperature of 200° C.

All gas injections are made using an automated headspace analyzer. Vial pressurization is 15 psi. The analyzer's sample oven, sampling valve, and transfer line are kept at 40° C., 45° C., and 50° C., respectively. The oven stabilization, vial pressurization, loop fill, loop equilibration, and sample injection times are 1.00 min., 0.20 min., 0.20 min., 0.05 min., and 1.00 min., respectively.

All determinations use a batch of nominal 20 mL headspace vials with volumes pre-measured for sample uniformity (actual vial volume varied by ≤2.0% relative standard deviation (n=6)). The average vial volume for the batch is determined from six randomly-selected vials by calculating the weight difference between the capped and sealed empty (i.e., air-filled) vial and the capped and sealed deionized water-filled vial using the known density of deionized water, then averaging. Blanks are prepared by sealing and capping 2 vials then purging each for 20 seconds with a gentle argon stream. Nitroxyl standards are prepared by sealing and capping four vials then purging each for 1 minute with a gentle stream, from a gas cylinder, of a 3000 ppm nitroxyl standard.

"Standards" are prepared by, in duplicate, accurately weighing 10±0.5 mg of a compound of the disclosure and adding it to each 4 mL vial. Using an auto pipette, 1 mL of argon-purged anhydrous DMF (Sigma-Aldrich) is added to each 4 mL vial to form a stock solution for each sample and the vials are capped and shaken and/or sonicated to insure complete dissolution upon visual observation. Using an auto pipette, 20 mL vials are charged with 5 mL of PBS (purged for at least 30 min. with argon prior to use), purged with argon for at least 20 sec., and sealed with a rubber septum. Using a 50 µL syringe, 50 µL of the stock solution is injected into each 20 mL vial containing the PBS.

Samples are prepared as follows. In duplicate, 18±1 mg of each sample is accurately weighed into each 4 mL vial. Using an auto pipette, 1 mL of argon-purged anhydrous DMF is added to each 4 mL vial to form a sample stock solution for each sample and the vials are capped and shaken and/or sonicated to insure complete sample dissolution upon visual observation. Using an auto pipette, 20 mL vials are charged with 5 mL of PBS (purged for at least 30 min. with argon prior to use), purged with argon for at least 20 sec., and sealed with a rubber septum. The vials are equilibrated for at least 10 min. at 37° C. in a dry block heater. Thereafter, using a 50 µL syringe, 50 µL of a sample stock solution is injected into each 20 mL vial containing the PBS. The vials are then held at 37° C. in the dry block heater for a time period such that the sum of the time spent in the dry block heater plus the time spent in the automated headspace analyzer oven before sample injection equals the desired incubation time.

Another procedure for determining the relative amounts of $N_2O$ released from compounds of the disclosure is as follows. GC is performed on a Varian CP-3800 instrument equipped with a 1041 manual injector, electron capture detector, and a 25 m 5 Å molecular sieve capillary column. Grade 5.0 nitrogen is used as both the carrier (8 mL/min) and the make-up (22 mL/min) gas. The injector oven and the detector oven are kept at 200° C. and 300° C., respectively. All nitrous oxide analyses are performed with the column oven held at a constant temperature of 150° C. All gas injections are made using a 100 µL gas-tight syringe with a sample-lock. Samples are prepared in 15 ml amber headspace vials with volumes pre-measured for sample uniformity (actual vial volume ranges from 15.19 to 15.20 mL). Vials are charged with 5 ml of PBS containing diethylenetriamine pentaacetic anhydride ("DTPAN"), purged with argon, and sealed with a rubber septum. The vials are equilibrated for at least 10 minutes at 37° C. in a dry block heater. A 10 mM stock solution of AS is prepared in 10 mM sodium hydroxide, and solutions of the nitroxyl donors are prepared in either acetonitrile or methanol and used immediately after preparation. From these stock solutions, 50 µL is introduced into individual thermally-equilibrated headspace vials using a 100 µL gas-tight syringe with a sample-lock to provide final substrate concentrations of 0.1 mM. Substrates are then incubated for 90 minutes or 360 minutes. The headspace (60 µL) is then sampled and injected five successive times into the GC apparatus using the gas-tight syringe with a sample lock. This procedure is repeated for 2 or more vials per donor.

Another procedure for determining $N_2O$ released from compounds of the disclosure is as follows. A Varian CP-3800 instrument equipped with a 1041 injector, electron capture detector, and a 25 m 5 Å molecular sieve capillary column was applied for the analysis of nitrous oxide ($N_2O$). Grade 5.0 nitrogen was used as both the carrier (8 mL/min) and the make-up (22 mL/min) gas. For all measurements, the column oven temperature was kept constant at 150° C., and the injector oven and the detector oven were held at 200° C. and 300° C., respectively. A 100 µL gastight syringe with a sample-lock was used for all gas injections. Samples were prepared in 6 mL Wheaton Clr headspace vials with volumes pre-measured for sample uniformity (actual vial volume ranges from 5.8-6.3 mL). Vials were charged with 3 mL of phosphate buffer containing the metal chelator, diethylenetriaminepentaacetic acid (DTPA), and fit with rubber septa and 20 mm aluminum seals. The vials were purged with argon and equilibrated for at least 10 minutes at 37° C. in a dry block heater. A stock solution of Angeli's salt (AS) was prepared in 10 mM sodium hydroxide, and compounds of the disclosure (10 mM) were prepared in acetonitrile and used immediately after preparation. 30 µL of the stock solutions was transferred into vials using a gastight syringe, yielding final concentrations of 0.5, 0.1, and 0.02 mM. Substrates were then incubated long enough to ensure complete decomposition and equilibration of $N_2O$ with the headspace. Depending on the concentration of the compound of the disclosure, 60 or 20 µL of the headspace was sampled and injected three times using a gastight syringe with a sample lock. The $N_2O$ yield was averaged and reported relative to the AS standard. The relative amounts of $N_2O$ release for compounds of the disclosure are provided in Table 3.

TABLE 3

| | % HNO | | |
|---|---|---|---|
| Compound | 500 µM | 100 µM | 20 µM |
| 1 | 70 | 75 | 91 |
| 2 | a | a | a |
| 3 | 20 | 29 | 41 |
| 4 | 8 | 17 | 29 |
| 5 | b | 26 | 35$^c$ | a Stable.
b Not determined due to low solubility.
$^c t_{1/2}$ = 3.2 min (measured using UV-vis spectroscopy).

As expected, HNO yields from the test compounds are consistent with the corresponding yields of their pyrazolone and carboxylic acid byproducts observed under the same conditions.

As shown in Table 3, the lower concentration of test compound results in higher yield of HNO. It is believed that lower concentrations of pyrazolone byproduct following decomposition of lower concentrations of test compound disfavors NHPY formation and correspondingly increases the yield of HNO (Scheme 2). Thus, the competition between nitrosocarbonyl hydrolysis to HNO and pyrazolone trapping depends on the relative concentration of pyrazolone byproduct.

Example 8: Kinetics of Nitroxyl Production from Compounds of the Disclosure as Determined Via UV-VIS Protocol A UV-VIS protocol was used to determine the decomposition kinetics of Compounds 1-5. According to this protocol, decomposition of the test compound was monitored by UV-Vis spectroscopy to measure donor half-lives at pH 7.4 and 37° C. (Guthrie, D. A.; Kim, N. Y.; Siegler, M. A.: Moore, C. D.; Toscano, J. P. *J. Am. Chem. Soc.* 2012, 134, 1962-1965; and Guthrie, D. A.; Ho, A.; Takahashi, C. G.; Collins, A.; Morris, M.; Toscano, J. P. *J. Org. Chem.* 2015, 80, 1338-1348). The measured half-lives for compounds of the disclosure are provided in Table 4.

TABLE 4

| Compound | R | $R^2$ | $R^3$ | $t_{1/2}$ |
|---|---|---|---|---|
| 1 | Ph | C(=NOMe)Me | Me | 25 min |
| 2 | Ph | Me | Me | Stable[a] |
| 3 | Ph | C(=NOMe)Me | MeO | 0.6 |
| 4 | Me | C(=NOMe)Me | MeO | 1.2 |
| 5 | Ph | C(=NOMe)Me | tBuO | N.D.[b] |

[a]Less than 5% decomposition after 2 days.
[b]Not Determined due to low solubility.

It is believed that the first step of decomposition is deprotonation which leads to release of nitrosocarbonyl plus the corresponding pyrazolone (Scheme 2). If the barrier to dissociation from anionic OHPY is very small, observed half-lives should correlate with donor $pK_a$ and the pyrazolone leaving group (Guthrie, D. A.; Ho, A.; Takahashi, C. G.; Collins, A.; Morris, M.; Toscano, J. P. *J. Org. Chem.* 2015, 80, 1338-1348; and Guthrie, D. A.; Nourian, S.; Takahashi, C. G.; Toscano, J. P. *J. Org. Chem.* 2015, 80, 1349-1356). Consistent with the much shorter half-life for Compound 1 ($t_{1/2}$=25 min) compared with Compound 2 (stable), the pyrazolone corresponding to Compound 1 is a better leaving group than the pyrazolone corresponding to Compound 2 (Guthrie, D. A.; Ho, A.; Takahashi, C. G.; Collins, A.; Morris, M.; Toscano, J. P. *J. Org. Chem.* 2015, 80, 1338-1348). Exchanging the R group from phenyl to methyl (Compound 3 vs. Compound 4) increases the half-life by a factor of two. A comparison of the known $pK_a$'s of the related compounds, PhC(O)NHOH (8.8) and PhOC(O)NHOH (10.0) (Steinberg, G. M.; Bolger, J. *J. Org. Chem.* 1956, 21, 660-662), indicates that the $pK_a$ of Compound 1 is likely lower than that of Compound 3. Although these two donors have the same pyrazolone leaving group, the longer half-life for Compound 1 ($t_{1/2}$=25 min) compared with Compound 3 ($t_{1/2}$=0.6 mm) suggests that the barrier to dissociation may also affect the observed half-lives.

Example 9: Mechanistic Studies of Nitrosocarbonyl Production Via $^1$H NMR Spectroscopy Protocol A $^1$H NMR Spectroscopy Protocol was used to confirm the formation of nitroso carbonyls following decomposition of Compound 1. In this protocol, 0.5 mM Compound 1 was incubated in the presence of 0.5 mM 3,4-dimethyl-1-phenylpyrazolone in 0.25 M phosphate buffer with 0.2 mM DTPA at pH 7.4, 80% $H_2O$, 10% $D_2O$, and 10% DMSO-$d_6$ at 37° C. under argon. Spectra were collected at the start of the experiment and after complete decomposition. See FIG. 3.

Upon decomposition of Compound I, quantitative formation of NHPY-1 was observed. This observation is strong evidence for nitrosocarbonyl formation.

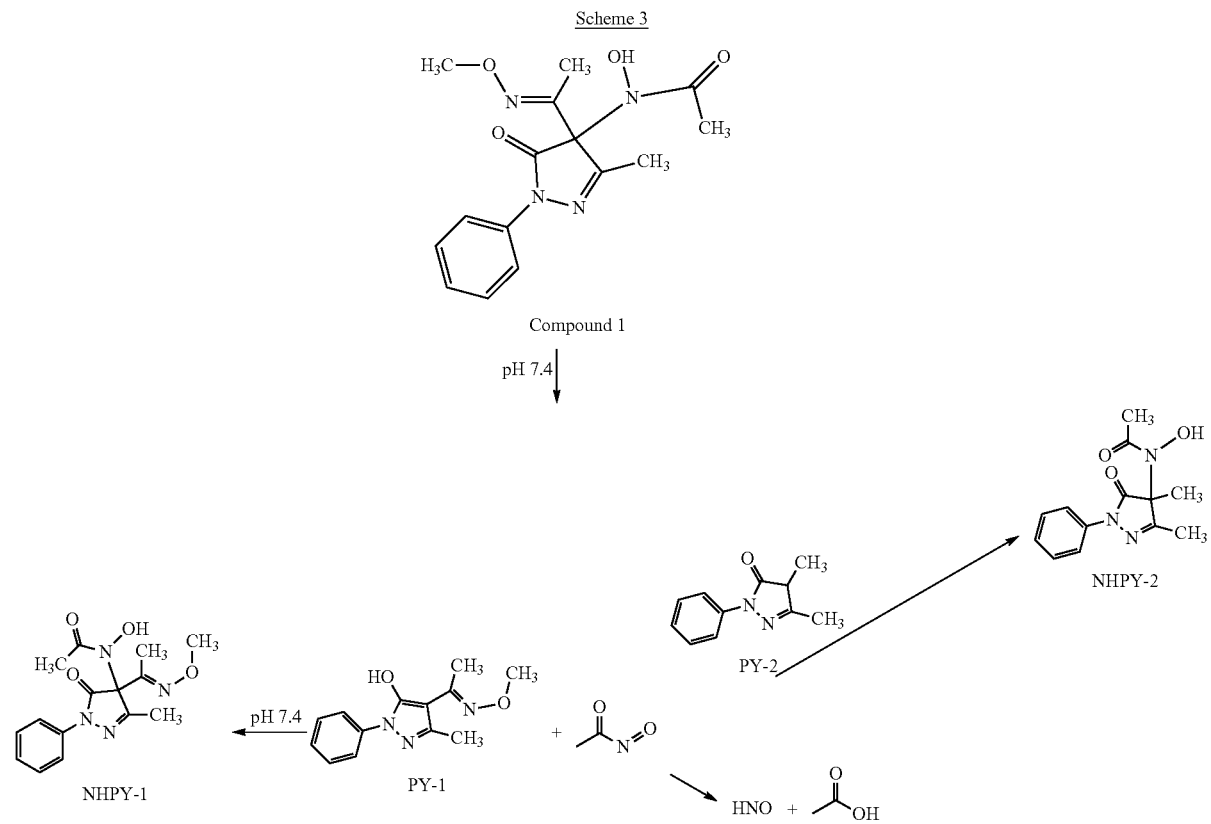

In the absence of 3,4-dimethyl-1-phenylpyrazolone (PY-2), the decomposition of Compound 1 provides N-hydroxy-N-(4-(1-(methoxyimino)ethyl)-3-methyl-5-oxo-1-phenyl-4,5-dihydro-1H-pyrazol-4-yl)acetamide (NHPY-1) (26%) (which has a half-life of 5 days), and HNO (70%) and acetate (73%) (Scheme 3 and Tables 2-4). The stability of NHPY-1, along with the observation that it is not formed in the presence of PY-2, also argues against the possibility of a direct intramolecular rearrangement from anionic Compound 1 to NHPY-1 without involvement of a nitrosocarbonyl intermediate.

Based on reactivity studies of bis-heteroatom-substituted amides (Glover, S. A. In *The Chemistry of Hydroxylamines, Oximes, and Hydroxamic Acids*, Part 2; Rappoport, Z., Liebman, J. F., Eds.; John Wiley & Sons: Chichester, West Sussex, 2009, p 839-923), the formation of NHPY-1 may be possible through the direct attack of PY-2 on the amide nitrogen of the hydroxamic acid moiety of NHPY-1 (Scheme 4). To examine this possibility, NHPY-1 was incubated with PY-2 and its stability was confirmed by $^1$H NMR spectroscopy at pH 7.4 and 10. The p$K_a$ of NHPY-1 has recently been measured to be 10.0 and its stability at or above pH 10 suggests a relatively high barrier for nitrosocarbonyl formation from this NHPY donor even when deprotonated (Nourian, S.; Zilber, Z. A.; Toscano, J. P. "Development of N-Substituted Hydroxamic Acids with Pyrazolone Leaving Groups as Nitrosocarbonyl Precursors", manuscript under review).

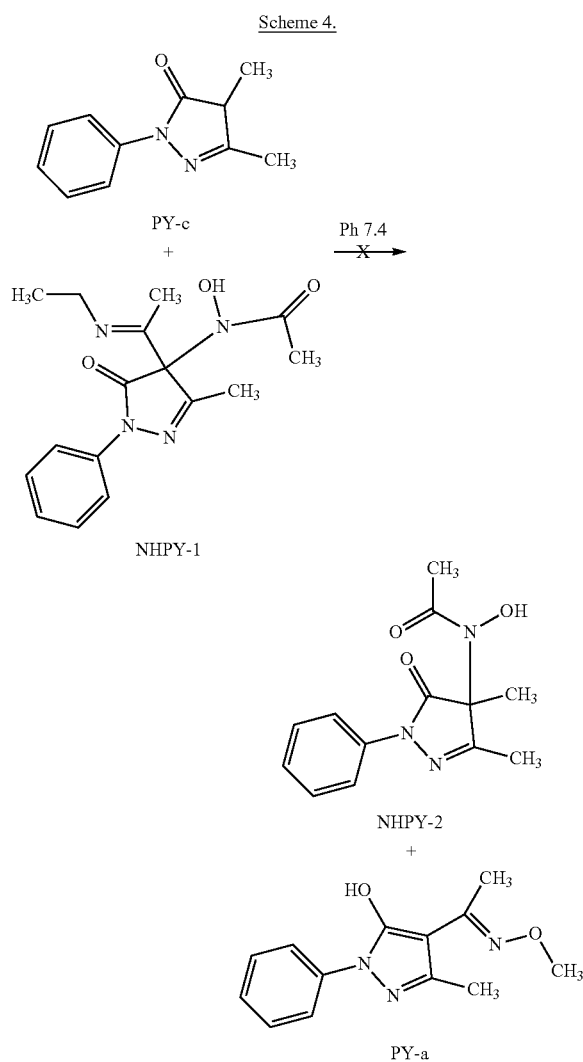

Scheme 4.

Example 10: In Vitro Plasma Stability of Compounds of the Disclosure in Plasma A procedure for determining in vitro plasma stability of compounds of the disclosure is as follows. The assay system comprises plasma from rat, dog or human (at least 3 donors, male, pooled) at pH 7.4, and (ii) an anticoagulant (sodium heparin or sodium citrate). Each test compound (5 μM) is incubated in plasma at 37° C. on a THERMOMIXER® with shaking. Three samples (n=3) are taken at each of seven sampling time points: 0, 10, 30, 60, 90, 180 and 360 minutes. The samples are immediately combined with 3 volumes (i.e., 3 times the volume of plasma) of acetonitrile containing 1% formic acid and an internal standard to terminate the reaction. AB SCIEX API 3000 LC-MS/MS analysis of the test compounds is performed without a standard curve. Plasma half-lives ($T_{1/2}$) of the test compounds are determined from graphs of the percent remaining values using the peak area response ratio.

Example 11: Solid-State Stability of Compounds of the Disclosure

A procedure for determining solid-state stability of the compounds of the disclosure is as follows. Solid, powdered samples of test compounds are sealed in double polyethylene bags and stored at 40° C., 75% relative humidity ("RH") for up to 3 months. Initially and after 1 month, 2 months, and 3 months of storage, the samples are analyzed for purity, as determined by high performance liquid chromatography ("HPLC"). Additionally, test compounds are admixed at a level of 50% by weight with one of the following excipients before stability testing: lactose, microcrystalline cellulose, or croscarmellose sodium. The resulting admixtures are also stored as described above then analyzed for purity of the test compound, as determined by HPLC. The HPLC apparatus comprises a quaternary or binary pump, an auto sampler, a thermostated column compartment, and a UV/Visible detector. The HPLC measurement conditions are as follows:

Column: Zorbax Eclipse XDB-C18, 2.1×50 mm, 3.5 μm (Agilent Technologies, Santa Clara, Calif.)
Injection Volume: 2 μL
Detection Wavelength: 220 nm
Mobile Phase A: 0.1% by volume formic acid ("FA") in water
Mobile Phase B: 0.1% by volume FA in acetonitrile
Diluent: About 0.2 mg sample/mL acetonitrile
Gradient:

| Time (min) | % A | % B |
|---|---|---|
| 0 | 99 | 1 |
| 15 | 70 | 30 |
| 20 | 99 | 1 |
| 23 | 99 | 1 |

Flow Rate: 0.8 mL/min
Column Temperature: 25° C.

Example 12: Separation of Enantiomers of Compounds of the Disclosure

The compounds of the disclosure can be optically active; thus, these compounds can exist as, inter alia, enantiomers. The enantiomers of a compounds of the disclosure can be separated by, e.g., chiral preparative supercritical fluid chromatography ("SFC") using the following procedure. A CHIRALPAK IA (250 mm×20 mm×5 μm) SFC semi-prep column (Daicel Corp., Osaka, Japan) elating with 25% methanol (plus diethylamine):75% carbon dioxide can be used. The flow rate is 50 mL/min. UV detection at 215 nm is used.

In one embodiment, a compound of the disclosure is present as a racemic mixture. In another embodiment, a compound of the disclosure is present as a substantially pure enantiomer, for example, in about 90% or greater enantiomeric excess in one embodiment, in about 92% or greater enantiomeric excess in another embodiment, in about 94% or greater enantiomeric excess in another embodiment, in about 95% or greater enantiomeric excess in another embodiment, in about 96% or greater enantiomeric excess in another embodiment, in about 97% or greater enantiomeric excess in another embodiment, in about 98% or greater enantiomeric excess in another embodiment, in about 99% or greater enantiomeric excess in another embodiment, in about 99.5% or greater enantiomeric excess in another embodiment, and in about 99.8% or greater enantiomeric excess in another embodiment.

Example 13: Pharmacodynamic Activity of Compounds of the Disclosure in Dogs

The effect of compounds of the disclosure on blood pressure in freely moving telemetered normal beagle dogs (n=3) after single oral doses is evaluated. The animals are surgically implanted with a pressure transducer equipped telemetry transmitter. The transmitter assembly is secured internally and a fluid-filled catheter is placed into the abdominal aorta to allow for collection of cardiovascular data. To evaluate cardiovascular effects, 3 dogs are given single oral doses of a test compound (100% PEG300 in gelatin capsules) at a concentration of 100 mg/mL and at doses of 30 mg/kg. Systemic blood pressure and heart rate are evaluated continuously for 2 hr before and for 24 hr after dosing. To compare the pharmacodynamic activity for all tested compounds, the mean systolic blood pressure (SBP) decrease during the first 2 hr post-dose is determined relative to the baseline SBP (30-120 min pre-dose).

While the invention has been disclosed in some detail by way of illustration and example for purposes of clarity of understanding, it is apparent to those in the art that various changes may be made and equivalents may be substituted without departing from the true spirit and scope of the invention. Therefore, the description and examples should not be construed as limiting the scope of the invention.

All references, publications, patents, and patent applications disclosed herein are hereby incorporated by reference in their entirety.

The invention claimed is:

1. A compound of formula (I), formula (II) or formula (III):

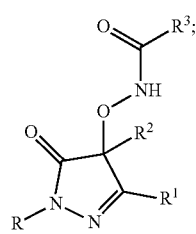

(I)

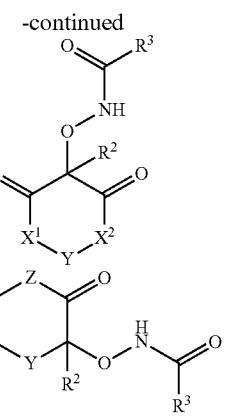

-continued or a pharmaceutically acceptable salt thereof, wherein:
R and $R^1$ are independently selected from the group consisting of hydrogen, (C1-C6)alkyl, $(C_1-C_4)$haloalkyl, $(C_1-C_4)$perhaloalkyl, $(C_6-C_{10})$aryl, $(C_1-C_6)$heteroalkyl, $(C_5-C_7)$heterocycloalkyl, (5- or 6-membered) heteroaryl, phenylsulfanyl, phenylsulfonyl, phenylsulfinyl and $(C_3-C_6)$cycloalkyl;
$R^2$ is selected from the group consisting of hydrogen, $(C_1-C_6)$alkyl, $-C(=O)R^4$, $-C(=S)R^4$, $C(=NR^4)R^5$, $-C(=NOR^4)R^5$, (5- or 6-membered)heteroaryl and $(C_6-C_{10})$aryl;
$R^3$ is selected from the group consisting of hydrogen, $(C_1-C_6)$alkyl, $(C_6-C_{10})$aryl, $-NR^6R^7$, and $-OR^8$; and
$R^4$, $R^5$, $R^6$, $R^7$, and $R^8$ are each independently selected from the group consisting of hydrogen, $(C_1-C_6)$alkyl, phenyl and benzyl;
wherein said alkyl, aryl, phenyl, benzyl, heteroalkyl, heterocycloalkyl and heteroaryl are unsubstituted or substituted with 1, 2, 3, 4 or 5 substituent(s) selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$ perhaloalkoxy, $-C(=O)OH$, $-C(=O)O(C_1-C_6)$alkyl, $-C(=O)NR^4R^5$, $-C(=O)-(C_5-C_7)$ heterocycloalkyl, $(C_5-C_7)$heterocycloalkyl, $(C_1-C_6)$ alkylsulfanyl, $(C_1-C_4)$haloalkylsulfanyl, $(C_1-C_4)$ perhaloalkylsulfanyl, $(C_1-C_6)$alkylsulfinyl, $(C_1-C_6)$ alkylsulfonyl, $(C_3-C_6)$cycloalkylsulfonyl, $(C_1-C_4)$ haloalkylsulfinyl, $(C_1-C_4)$haloalkylsulfonyl, $(C_1-C_4)$ perhaloalkylsulfinyl, $(C_1-C_4)$perhaloalkylsulfonyl, $-S(O)_2-NH_2$, $-S(O)_2-NR^6R^7$, $-S(O)_2$-phenyl, $-S(O)_2-(C_5-C_7)$heterocycloalkyl, $-S(=O)(=NR^8)$ $(C_1-C_6)$alkyl, $-NR^4R^5$, N—$(C_1-C_6)$alkylaminosulfonyl, and N,N-di$(C_1-C_6)$alkylaminosulfonyl.

2. The compound of claim 1, wherein R is selected from the group consisting of hydrogen, $(C_1-C_6)$alkyl, $(C_6-C_{10})$ aryl and (5- or 6-membered)heteroaryl, wherein said alkyl, heteroaryl and aryl are unsubstituted or substituted with 1, 2 or 3 substituent(s).

3. The compound of claim 1, wherein $R^1$ is selected from the group consisting of $(C_1-C_6)$alkyl, $(C_1-C_4)$perhaloalkyl, $(C_1-C_6)$alkoxy, $(C_6-C_{10})$aryl, (5- or 6-membered)heteroaryl, phenylsulfanyl, phenylsulfonyl, phenylsulfinyl and $(C_3-C_6)$ cycloalkyl, wherein said alkyl, perhaloalkyl, alkoxy, aryl, heteroaryl, phenylsulfanyl, phenylsulfonyl, phenylsulfinyl and cycloalkyl are unsubstituted or substituted with 1, 2 or 3 substituent(s).

4. The compound of claim 1, wherein $R^2$ is selected from the group consisting of $(C_1-C_6)$alkyl, $-C(=O)R^4$, $-C(=S)R^4$, $C(=NR^4)R^5$, $-C(=NOR^4)R^5$, (5- or 6-membered)heteroaryl and $(C_6-C_{10})$aryl, wherein said aryl is unsubstituted or substituted with 1, 2 or 3 substituent(s).

5. The compound of claim 1, wherein $R^3$ is selected from the group consisting of $(C_1-C_6)$alkyl, phenyl, —$NR^6R^7$, and $(C_1-C_6)$alkoxy, wherein $R^6$ and $R^7$ are independently selected from hydrogen and $(C_1-C_6)$alkyl.

6. The compound of claim 1, wherein the compound of formula (I) is:

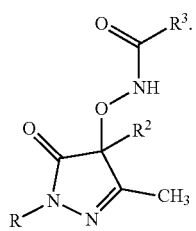

(I')

7. The compound of claim 1, wherein the compound of formula (I) is selected from the group consisting of:

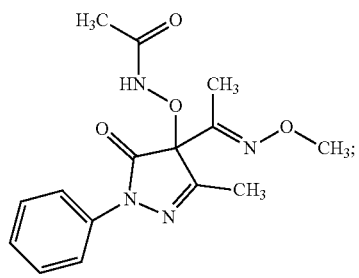

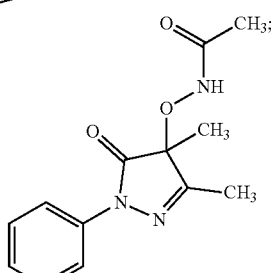

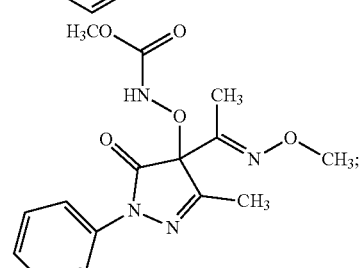

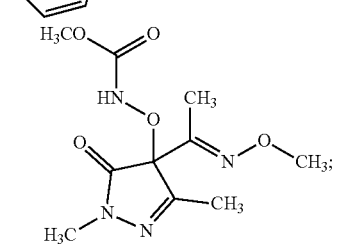

-continued

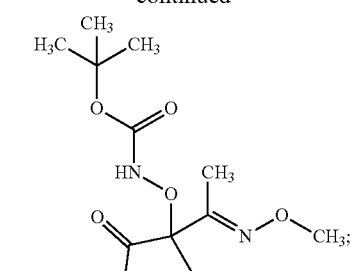

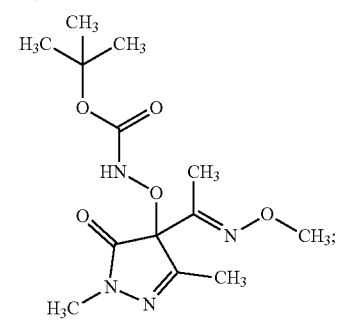

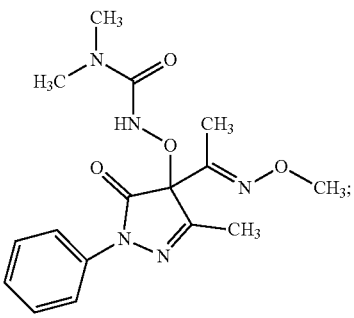

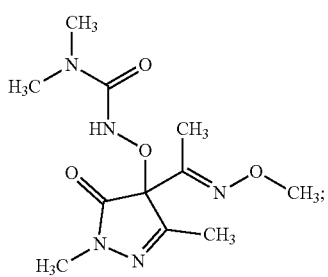

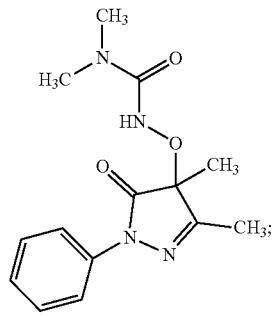

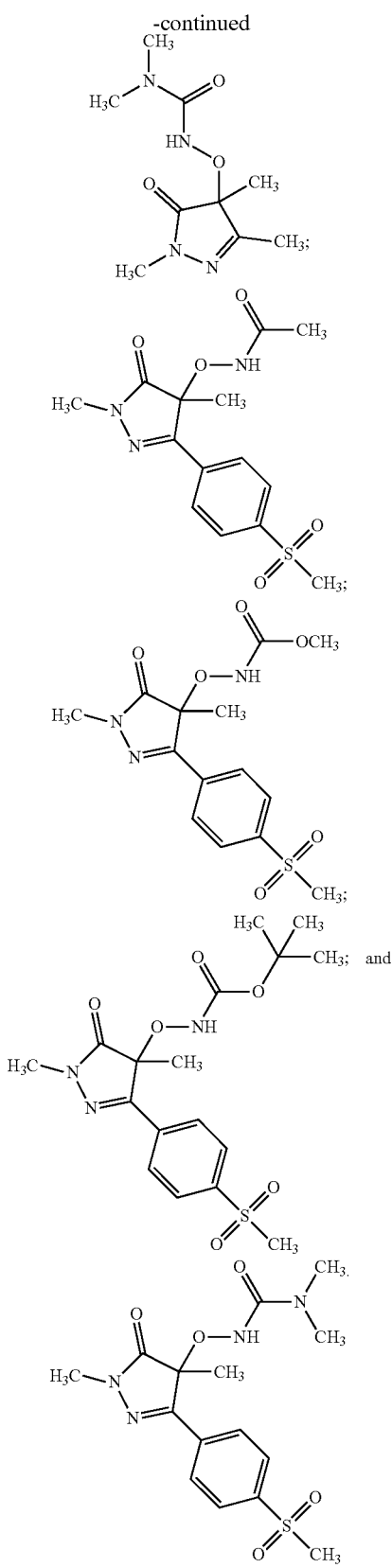

8. A pharmaceutical composition comprising a compound of claim 1, and a pharmaceutically acceptable excipient.

9. A method of treating a cardiovascular disease responsive to nitroxyl therapy, the method comprising administering an effective amount of the compound of claim 1 to a patient in need thereof.

10. A kit for treating a disease or condition responsive to nitroxyl therapy comprising a compound of claim 1; and instructions for use of the kit.

11. The compound of claim 1, wherein R is selected from the group consisting of hydrogen, $(C_1-C_6)$alkyl, (5- or 6-membered)heteroaryl or phenyl, wherein said alkyl, heteroaryl and phenyl are unsubstituted or substituted with 1, 2 or 3 substituent(s).

12. The compound of claim 1, wherein R is selected from the group consisting of hydrogen, methyl and phenyl.

13. The compound of claim 1, wherein R is methyl or phenyl.

14. The compound of claim 1, wherein $R^1$ is selected from the group consisting of $(C_1-C_6)$alkyl, $(C_1-C_4)$perhaloalkyl, $(C_1-C_6)$alkoxy, phenyl, (5- or 6-membered)heteroaryl, phenylsulfanyl, phenylsulfonyl, phenylsulfinyl and $(C_3-C_6)$cycloalkyl, wherein said alkyl, perhaloalkyl, alkoxy, phenyl, heteroaryl, phenylsulfanyl, phenylsulfonyl, phenylsulfinyl and cycloalkyl are unsubstituted or substituted with 1, 2 or 3 substituent(s).

15. The compound of claim 1, wherein $R^1$ is methyl or phenyl, wherein said phenyl is unsubstituted or substituted with 1, 2 or 3 substituent(s).

16. The compound of claim 1, wherein $R^2$ is selected from the group consisting of $(C_1-C_6)$alkyl, —C(=NOR$^4$)R$^5$, (5- or 6-membered)heteroaryl and phenyl, wherein said alkyl, heteroaryl and phenyl are unsubstituted or substituted with 1, 2 or 3 substituent(s).

17. The compound of claim 1, wherein $R^2$ is methyl, —C(=NOR$^4$)R$^5$, or phenyl; and $R^4$ and $R^5$ are independently selected from $(C_1-C_6)$alkyl.

18. The compound of claim 1, wherein $R^2$ is methyl or —C(=NOR$^4$)R$^5$; and $R^4$ and $R^5$ are each methyl.

19. The compound of claim 1, wherein $R^3$ is $(C_1-C_6)$alkyl, —NR$^6$R$^7$ or $(C_1-C_6)$alkoxy.

20. The compound of claim 1, wherein the compound of formula (I) is:

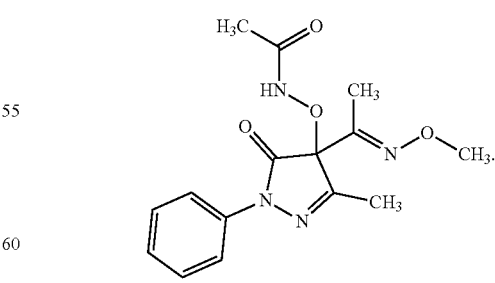

* * * * *

UNITED STATES PATENT AND TRADEMARK OFFICE
CERTIFICATE OF CORRECTION

| | | |
|---|---|---|
| PATENT NO. | : 10,913,728 B2 | Page 1 of 1 |
| APPLICATION NO. | : 16/321378 | |
| DATED | : February 9, 2021 | |
| INVENTOR(S) | : John P. Toscano et al. | |

It is certified that error appears in the above-identified patent and that said Letters Patent is hereby corrected as shown below:

In the Claims

Claim 1, at Column 81, Line 53 through Column 82, Line 17:
"A compound of formula (I), formula (II) or formula (III):

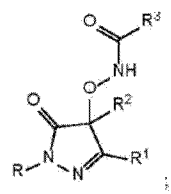

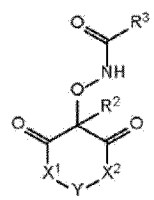

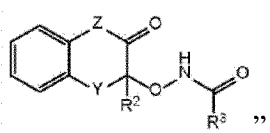
";

Should be:
-- A compound of formula (I):

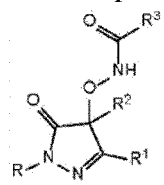

(I); --.

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*